US012390542B2

(12) United States Patent
Gerber et al.

(10) Patent No.: US 12,390,542 B2
(45) Date of Patent: Aug. 19, 2025

(54) ON-DEMAND AGENT DISPENSING DEVICES AND RELATED METHODS

(71) Applicant: ROXILLA LLC, New York, NY (US)

(72) Inventors: Danielle Evin Gerber, New York, NY (US); Rock Positano, New York, NY (US); Robert White, Bloomingdale, NJ (US)

(73) Assignee: Roxilla LLC, New York, NY (US)

( * ) Notice: Subject to any disclaimer, the term of this patent is extended or adjusted under 35 U.S.C. 154(b) by 0 days.

(21) Appl. No.: 18/061,784

(22) Filed: Dec. 5, 2022

(65) Prior Publication Data

US 2023/0123500 A1     Apr. 20, 2023

Related U.S. Application Data

(63) Continuation-in-part of application No. PCT/US2021/036212, filed on Jun. 7, 2021.
(Continued)

(51) Int. Cl.
*A61L 2/00*  (2006.01)
*A47K 5/12*  (2006.01)
(Continued)

(52) U.S. Cl.
CPC .......... *A61L 2/0088* (2013.01); *A47K 5/1201* (2013.01); *A61L 2/18* (2013.01);
(Continued)

(58) Field of Classification Search
CPC . A61L 2/0088; A61L 2/18; A61L 2/26; A61L 2101/34; A61L 2101/38; A61L 2202/16; A47K 5/1201
See application file for complete search history.

(56) References Cited

U.S. PATENT DOCUMENTS

| 4,638,043 A * | 1/1987 | Szycher .................. A61L 15/26 522/6 |
| 4,832,942 A * | 5/1989 | Crace ..................... B32B 27/065 428/305.5 |
| 5,310,559 A * | 5/1994 | Shah ..................... A61K 9/7084 424/424 |

(Continued)

FOREIGN PATENT DOCUMENTS

WO    2021248127    12/2021

OTHER PUBLICATIONS

International Search Report and Written Opinion of the International Searching Authority for PCT/US2021/036212, Sep. 9, 2021, 10 pages.

*Primary Examiner* — Bob Zadeh
(74) *Attorney, Agent, or Firm* — Heslin Rothenberg Farley & Mesiti P.C.

(57) ABSTRACT

The present disclosure provides on-demand agent dispensing patches, kits and related methods. A flexible patch is configured to provide on-demand dispensing of the agent via compression of the patch. The patch comprises: an adhesive layer to removably couple the patch to a surface; at least one reservoir layer overlying the adhesive layer configured to absorb and retain the agent therein; at least one dispenser layer overlying the at least one reservoir layer comprising a plurality of solid portions and an array of a plurality of openings configured to inhibit evaporation of the agent and control a flow of the agent therefrom upon the compression of the patch; and at least one backer layer between the adhesive layer and the at least one reservoir layer being substantially impervious to the agent. The at least one reservoir layer may be void of the agent, which may be provided in a container.

34 Claims, 37 Drawing Sheets

Related U.S. Application Data

(60) Provisional application No. 63/418,041, filed on Oct. 21, 2022, provisional application No. 63/035,006, filed on Jun. 5, 2020.

(51) Int. Cl.
  *A61L 2/18* (2006.01)
  *A61L 2/26* (2006.01)
  *A61L 101/34* (2006.01)
  *A61L 101/38* (2006.01)

(52) U.S. Cl.
  CPC ............. *A61L 2/26* (2013.01); *A61L 2101/34* (2020.08); *A61L 2101/38* (2020.08); *A61L 2202/16* (2013.01)

(56) References Cited

U.S. PATENT DOCUMENTS

| | | | | |
|---|---|---|---|---|
| 5,653,699 | A * | 8/1997 | Reed | A61F 13/023 |
| | | | | 604/369 |
| 2006/0222693 | A1 * | 10/2006 | Silguero | A61K 9/7084 |
| | | | | 424/449 |
| 2007/0049894 | A1 | 3/2007 | Fitts, Jr. | |
| 2007/0264316 | A1 * | 11/2007 | Adachi | A61K 9/703 |
| | | | | 424/448 |
| 2011/0111000 | A1 | 5/2011 | Russell | |
| 2011/0293681 | A1 | 12/2011 | Berlin | |
| 2015/0117932 | A1 | 4/2015 | Russell et al. | |
| 2015/0118283 | A1 | 4/2015 | Von Blücher | |
| 2019/0029971 | A1 * | 1/2019 | Lee | A61K 47/10 |
| 2023/0123500 | A1 * | 4/2023 | Gerber | A61L 2/18 |
| | | | | 222/105 |

* cited by examiner

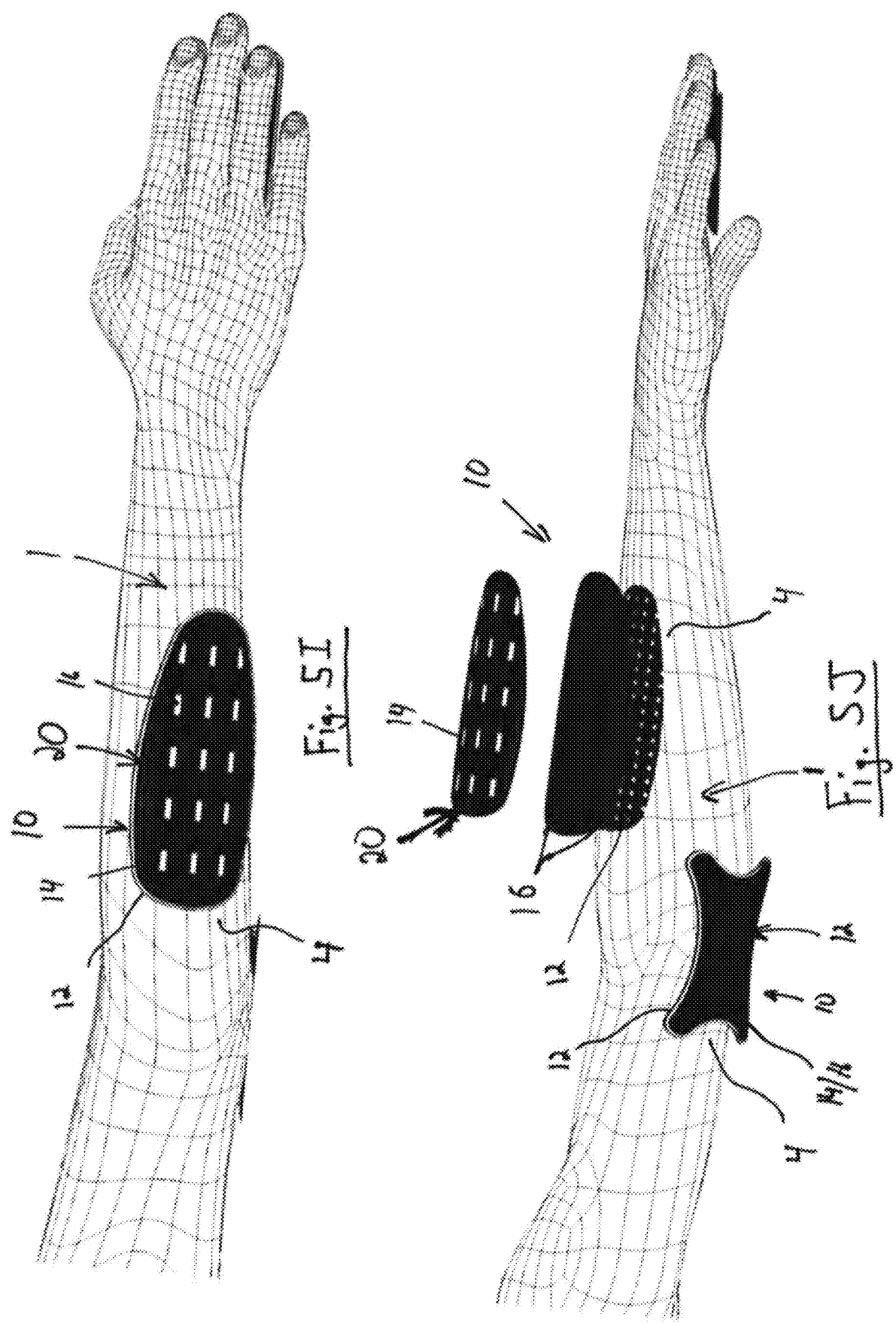

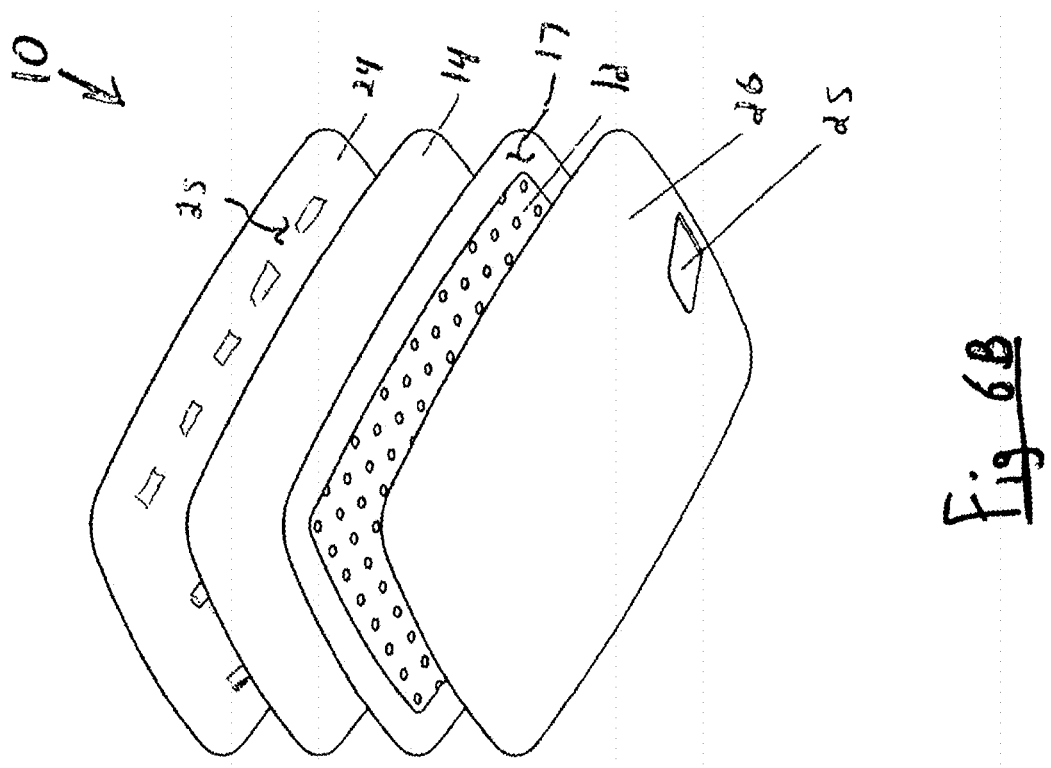

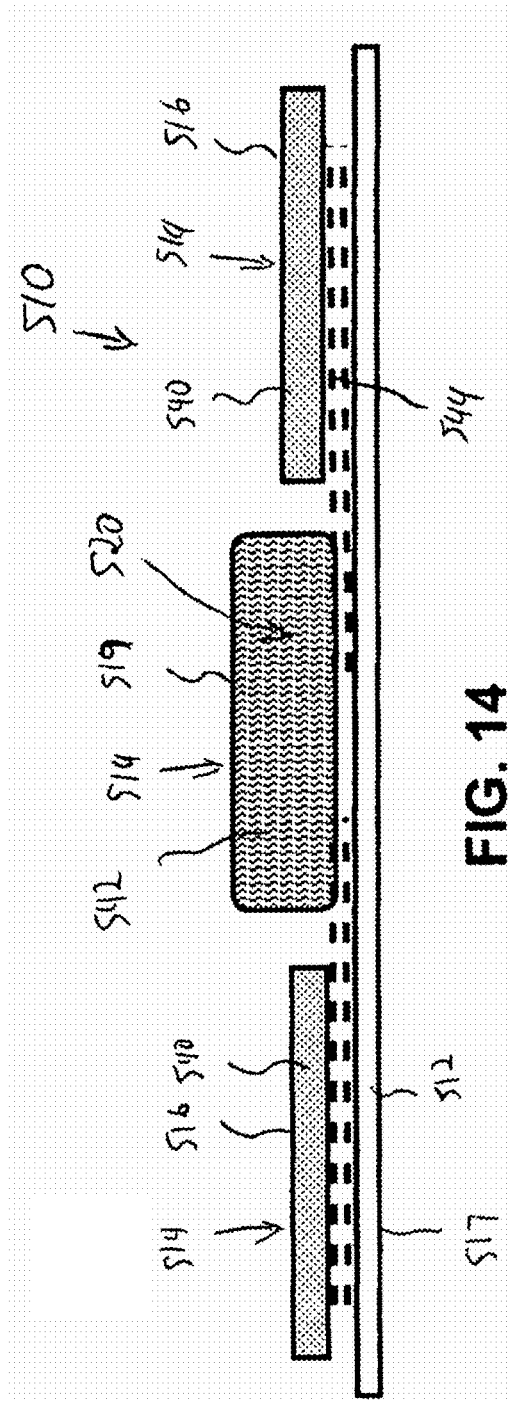
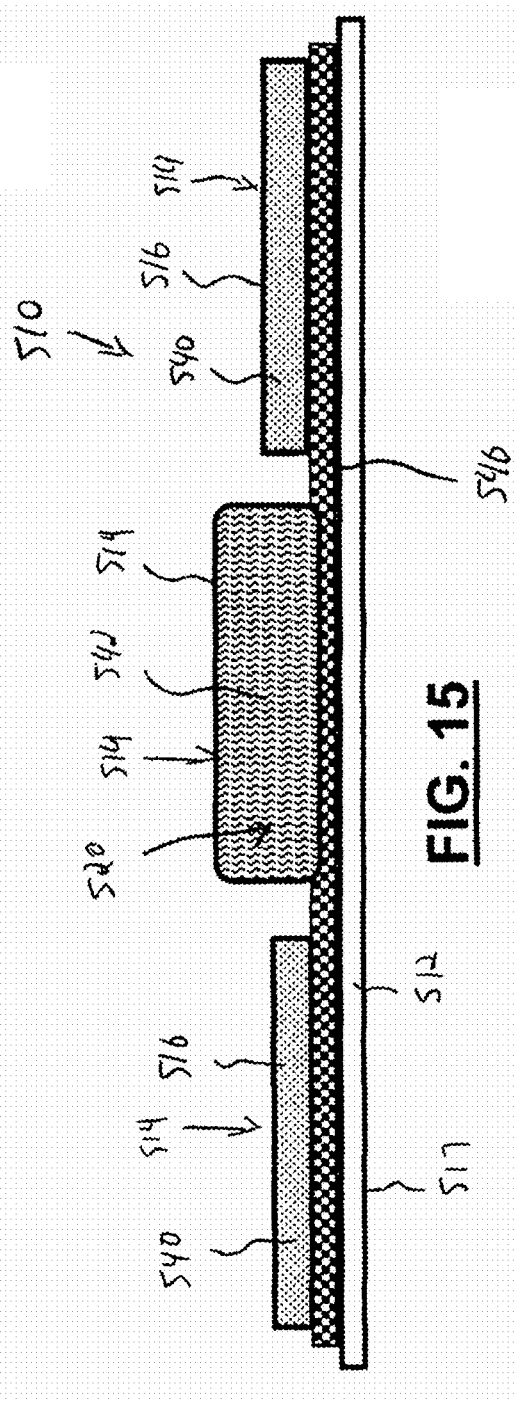

ON-DEMAND AGENT DISPENSING DEVICES AND RELATED METHODS

CROSS-REFERENCE TO RELATED APPLICATION

This application is a by-pass continuation-in-part of PCT International Application No. PCT/US2021/036212, filed Jun. 7, 2021, and entitled On-Demand Agent Dispensing Devices and Related Methods, which claims priority benefit under 35 U.S.C. § 119(e) of U.S. Provisional Patent Application No. 63/035,006, filed Jun. 5, 2020, and entitled On-Demand Agent Dispensing Devices and Related Methods, and also claims priority benefit under 35 U.S.C. § 119(e) of U.S. Provisional Patent Application No. 63/418,041, filed Oct. 21, 2022, and entitled Agent Dispensing Devices, Kits and Related Methods, which are incorporated herein by reference in their entireties.

FIELD OF THE DISCLOSURE

The present disclosure relates generally to on-demand agent (e.g., disinfectant) dispensing devices, kits and related methods. More specifically, the present disclosure relates to agent (e.g., disinfectant) dispensing adhesive patches that are configured to be removably affixed to a user or surface, and provide on-demand dispensing of an agent over an extended period of time.

BACKGROUND

There is substantial evidence that pathogens (i.e., disease-causing microorganisms, such as various viruses, bacteria, fungus, and parasites) can be transmitted from a first person to a second person via the first person physically touching the second person (e.g., via a handshake, hug, kiss, etc.) or the first person physically touching or otherwise infecting (e.g., via one or more respiratory function, a pet, etc.) a communal object (e.g., a surface, object, knob, button, handle, hand rail, key, screen, money, card, etc.) that is subsequently physically touched by the second person. Most commonly, pathogens are passed between people via physical touch through their hands—a pathogen becomes present one the first person's hand, and is transferred to the second person's hand via physical contact with the first person's hand or with an object that that first person's hand previously contacted or that the first person infected via one or more respiratory functions (e.g., breathing, coughing, sneezing, talking, etc.) or by a third party (e.g., via another person, a pet, etc.). Thus, not only can a person become infected by a pathogen by touching their eyes, nose or mouth with their hand (or with an object that that they touched with their hand), they can pass a pathogen to one or more other people by touching a communal object.

Because many infectious pathogens (such as viruses, for example the common cold) are contracted and spread to others via physical touching primarily by the hands, conventional medical wisdom teaches that the best way to prevent contraction and transmission of most pathogens (and resulting infections) is by thoroughly and frequently disinfecting/sanitizing/sterilizing one's hands throughout the day by washing their hands with soap and water. In addition to and/or in place of washing one's hands, a topical disinfecting/sanitizing/sterilizing agent such as, for example, a denatured alcohol, an anti-bacterial hand gel, or an anti-bacterial hand lotion to further protect the hands may be utilized.

Although these measures will help to control the spread of many pathogens residing on the skin, they are ineffective if not performed routinely and methodically. Unfortunately, many individuals do not have immediate access to facilities to adequately wash their hands with soap and water, and/or to a topical disinfectant. For example, many liquid and/or gel topical disinfectants are packaged in a bottle configured with a spray or squeeze dispenser. These bottled disinfectants requires the bottle to be carried by an individual, taken out when disinfectant is needed, and manually opened and applied to their hand(s). As such, they are often not utilized as often as they should and/or would be compared to if they were easily available on-demand. As another example, sanitizing wipes or towelettes that contained a liquid topical disinfectant are sometimes utilized, but include the same disadvantages as bottled disinfectants.

Hand sanitizer stations which contain a relatively larger reservoir of a topical disinfectant are also commonplace. Such stations are typically only found in high population spaces, areas where pathogens are more commonly found and/or areas where vulnerable people are located. Because of their scarcity, sanitizer stations thereby fail to protect users from the constant barrage of surfaces and 3rd party individuals comes into contact with on a daily basis.

It is further noted that other liquid and/or gelatinous agents and materials that people wish to receive periodic doses of (or periodically dispense) suffer from the same deficiencies noted above with respect to disinfectant/sanitizer.

It is thereby an object of the on-demand disinfectant dispensing devices and related disinfecting methods provided herein to addresses one or more of the aforementioned problems of the prior art. The on-demand agent dispensing devices, kits and related methods disclosed herein solve the above noted deficiencies of current agent dispensing devices and related methods by, inter alia, providing a removably affixable device/patch that provides on-demand access (via dispensing doses or amounts thereof) of a liquid and/or gelatinous agent (e.g., a disinfectant) to a user over an extended period of time.

SUMMARY

On-demand agent (e.g., disinfectant) dispensing devices (and disinfecting methods utilizing such devices) that can be removably affixed to a user or surface that provide quick and easy access to the agent over an extended period of time are disclosed herein. The present disclosure provides such devices and kits, and related methods, for dispensing the agent onto a user's body (e.g., the skin of a user's hand) via an adhesive patch. In embodiments wherein the agent is a sanitizer/disinfectant liquid or gel, the devices, kits and methods provide for manual dispensing of the sanitizer/disinfectant to a user (e.g., a user hand), and potential transfer of the sanitizer/disinfectant to another portion of the user, another person or an inanimate object. Such on-demand disinfectant dispensing devices, kits and methods are thereby able to provide an on-demand sanitizer/disinfectant to one or more people and/or surfaces.

The on-demand agent dispensing devices and kits provide simple, cost effective solutions to selectively provide access to, and dispensing of, a liquid or gelatinous agent, such as but not limited to alcohol-based sanitizer/disinfectant liquids or gels.

The devices are self-contained, are void of containers that need to be carried and opened, retain the agent within the device (i.e., a no spill solution), and do not necessitate pouring or spraying for dispensing of the agent. In some embodiments, the on-demand agent dispensing devices and kits may be configured to with an adhesive patch that is configured to be removably affixed to a user, such as to the user's skin or the user's clothing (or any other inanimate object carried or worn by the user). In some embodiments, the on-demand agent dispensing patches are wearable, and may be configured to be removably affixed to an active point/portion of contact of the user that would benefit from having the agent at that location, such as sanitizer/disinfectant on the inside of a user's hand (e.g., on the palm and/or fingers). In some embodiments, the on-demand agent dispensing wearable device may be configured to be removably affixed to a passive portion of the user's skin (or an object worn/carried by the user) (or on an inanimate object remote from the user) that is spaced from the point/portion of contact of the user, to allow for selective application of the agent on the portion of contact of the user from the device. For example, a passive on-demand disinfectant dispensing wearable patch device may be configured to be removably affixed to the back of a user's hand (or a user's forearm) or on/in clothing worn by the user, and the user may wipe their finger(s)/hand on/over the device to apply the disinfectant thereto (and thereby disinfect their finger(s)/hand). In such a passive disinfecting embodiment, the on-demand disinfectant dispensing wearable device provides quick and discrete on-demand access to a sanitizer/disinfectant where swiping/contacting the device disinfects a person's point/portion of contact (e.g., their hand(s) or other skin surface).

The on-demand agent dispensing device embodiments may be configured to be applied to an active or passive surface portion of a user (or an object) to disinfect it, and, potentially, passes it on to a third party that subsequently touches the surface portion (i.e., pays it forward). In this way, the on-demand disinfectant dispensing devices can provide a level of disinfecting of safety to the user, with the additional benefit of protecting others that may touch a common surface/object. Communal touchpoints can thus be sanitized and provide an integral part to the health and wellbeing of a community as a whole.

The on-demand agent dispensing devices of the present disclosure are configured as an on-demand long lasting liquid/gelatinous agent supply and dispensing patch. The on-demand agent supply and dispensing patch includes an adhesive layer or portion that is configured to removably attach to a user or an inanimate object. The on-demand agent supply and dispensing patch also includes at least one reservoir layer that is configured to absorb and retain the liquid/gelatinous agent therein, and at least one metered/controlled release or dispensing layer that overlies at least a portion of the at least one reservoir layer. The at least one metered/controlled release layer is configured to control the release (e.g., volume dispensed and pressure needed to dispense) of the agent at/to an outer surface of the patch (and thereby to a user) from the at least one reservoir layer, and mitigate/inhibit evaporation of the liquid/gelatinous agent in the at least one reservoir layer. In some embodiments, the on-demand agent supply and dispensing patch may include at least one backer layer positioned between the adhesive layer and the at least one reservoir layer that is impervious to the liquid/gelatinous agent such that the liquid/gelatinous agent is prevented from interacting with the adhesive of the adhesive layer, and is thereby retained above the at least one backer layer. In some embodiments, the at least one reservoir layer, the at least one metered/controlled dispensing layer and the at least one backer layer are heat welded or sealed together about the periphery of the patch, and form a peripheral barrier or border about an interior area or portion of the patch that substantially retains the agent within the at least one reservoir layer in the interior area of the patch until it is selectively dispended by a user via pressure applied to the outer surface of the patch such that the at least one reservoir layer is compressed (in a thickness direction thereof).

In one aspect, the present disclosure provides an on-demand liquid or gelatinous agent dispensing kit, comprising: a container containing a volume of a liquid or gelatinous agent; and a flexible patch configured to contain, and provide on-demand dispensing of, the agent via compression of the patch in a thickness direction thereof. The patch comprises: an adhesive layer configured to removably couple the patch to a surface, the adhesive layer defining an inner face of the patch; at least one reservoir layer that is configured to absorb and retain the agent therein, the at least one reservoir layer overlying the adhesive layer in the thickness direction; at least one dispenser layer overlying the at least one reservoir layer in thickness direction comprising a plurality of solid portions and an array of a plurality of openings extending through a thickness thereof, the at least one dispenser layer configured to inhibit evaporation of the agent, and control a flow of the agent from the at least one reservoir layer upon the compression of the patch in the thickness direction, when the agent is contained within the at least one reservoir layer; and at least one backer layer positioned between the adhesive layer and the at least one reservoir layer in the thickness direction, the at least one backer layer being substantially impervious to the agent. The solid portions of the at least one dispenser layer and portions of the at least one reservoir layer underlying the plurality of openings of the at least one dispenser layer define outer face of the patch. The at least one reservoir layer is void of the agent absorbed therein.

In some embodiments, the adhesive is a biocompatible adhesive. In some embodiments, the patch further comprises an inner protective film layer extending over and removably coupled to the adhesive layer. In some embodiments, the patch further comprises an outer protective film layer extending over and removably coupled to the outer face of the patch. In some embodiments, the patch further comprises a mechanical connector configured to removably attach the patch to an object.

In some embodiments, the agent is a disinfectant. In some such embodiments, the disinfectant is a biocompatible disinfectant. In some embodiments, the disinfectant comprises ethyl, isopropyl, ethanol (ethyl alcohol), triclosan, triclocarban, benzalkonium chloride, benzethonium chloride or a combination thereof. In some embodiments, the disinfectant comprises ethanol (ethyl alcohol). In some embodiments, the disinfectant comprises a dynamic viscosity within the range of about 4 (Pa·s)(m2/s) and about 15 (Pa·s)(m2/s) at 20 degrees Celsius.

In some embodiments, the agent comprises a medicant or vitamin. In some embodiments, the agent comprises an insecticide. In some embodiments, the agent comprises a fragrance. In some embodiments, the agent comprises a food product. In some embodiments, the agent comprises a cleaning product. In some embodiments, the agent comprises a paint. In some embodiments, the agent comprises an oil.

In some embodiments, the at least one backer layer is substantially impervious to the agent and to air. In some embodiments, the at least one backer layer comprises a solid sheet of material. In some embodiments, the at least one backer layer comprises a polymer layer. In some embodiments, the at least one backer layer comprises at least one polyethylene layer, polypropylene layer, styrene layer, polyetheretherketone layer, acrylic layer, polyvinyl chloride layer, polyurethane layer, Teflon (Polytetrafluoroethylene) layer, syrlyn layer or a combination thereof.

In some embodiments, the at least one dispenser layer comprises a sheet of material that is impervious to the agent. In some embodiments, the at least one dispenser layer comprises a sheet of material that is impervious to air. In some embodiments, the at least one dispenser layer comprises a polymer layer. In some embodiments, the at least one dispenser layer comprises at least one polyethylene layer, polypropylene layer, styrene layer, polyetheretherketone layer, acrylic layer, polyvinyl chloride layer, polyurethane layer, Teflon (Polytetrafluoroethylene) layer, syrlyn layer or a combination thereof. In some embodiments, the solid portions of the at least one dispenser layer comprise within the range of about 10% and about 65% of the total area of the outer face. In some embodiments, the plurality of openings of the at least one dispenser layer comprise an average total area within the range of about 50 mm$^2$ and about 300 mm$^2$ at the outer face. In some embodiments, each of the plurality of openings of the at least one dispenser layer comprise a total area within the range of about 0.05 mm$^2$ and about 0.3 mm$^2$ at the outer face.

In some embodiments, the at least one reservoir layer comprises one or more layers of a fabric, Gore-Tex, gauze, an absorbing gel, a polymer, paper, a foam or a combination thereof. In some embodiments, the at least one reservoir layer comprises one or more layers of polymer fibers, cotton fibers, silicone fibers, hydrogel or a combination thereof. In some embodiments, the at least one reservoir layer comprises a fabric layer of non-woven polymer fibers. In some embodiments, the at least one reservoir layer comprises a layer of non-woven polyethylene and/or polypropylene fibers. In some embodiments, the at least one reservoir layer comprises a natural or synthetic non-woven fabric layer. In some embodiments, the at least one reservoir layer is configured to absorb and retain within the range of about 2 grams and about 50 grams of the agent. In some embodiments, the at least one reservoir layer comprises a detached agent capacity within the range of about 1,000 g/mm$^2$ and about 2,500 g/mm$^2$. In some embodiments, the at least one reservoir layer comprises an agent absorbency rate of at least 5 g/sec for at least the first 5 seconds of water contact. In some embodiments, when the agent is contained within the at least one reservoir layer, the patch is configured such that a compressive force acting in the thickness direction and applied to the outer surface thereof of at least 1 gram/mm$^2$ causes the agent to flow through the plurality of apertures and onto the outer face and/or an object at the outer face.

In some embodiments, the, when the agent is contained within the at least one reservoir layer, the patch is configured such that no more than 5 grams of the agent evaporates over 1.5 hours in an ambient environment of non-moving air at 20 degrees Celsius.

In some embodiments, the patch comprises a total thickness within the range of about 0.05 mm and about 3 mm. In some embodiments, an inner portion of the patch defines a first maximum thickness, and a peripheral edge portion of the patch extending about the inner portion and defining an outer extent of the patch defines a second thickness that is less than the first thickness. In some embodiments, a peripheral edge portion of the patch defining an outer extent of the patch comprises the at least one reservoir layer, the at least one dispenser layer and the at least one backer layer being bonded together. In some embodiments, the at least one reservoir layer, the at least one dispenser layer and the at least one backer layer are heat, radio-frequency or ultrasonic welded together at the peripheral edge portion of the patch.

In some embodiments, the adhesive comprises a biocompatible adhesive. In some embodiments, the adhesive layer on the outer side of the front face comprises an acrylic-based pressure-sensitive adhesive. In some embodiments, the adhesive layer comprises an adhesive and scrim layer construct.

In some embodiments, the container is separate and distinct from the flexible patch. In some embodiments, the container is integrated within, or coupled to, the flexible patch. In some embodiments, the volume of the agent is contained within a manually breakable shell or envelope. In some embodiments, the shell or envelope is contained within the flexible patch, or positioned adjacent to the at least one dispenser layer of the flexible patch.

In another aspect, the present disclosure provides an on-demand agent dispensing pocket device. The device comprises: a flexible agent-impervious pocket comprising a front face, a back face, a bottom portion, a top portion, lateral side portions and an interior cavity between inner sides of the front and back faces, wherein the interior cavity is closed at the bottom and lateral side portions and open or openable at the top portion, and wherein the impervious pocket is impervious to a liquid or gelatinous agent; and at least one reservoir dispenser layer positioned within the interior cavity of the pocket that is configured to absorb and retain a liquid or gelatinous agent therein, and control a flow of the agent from the at least one reservoir layer upon compression of the at least one reservoir layer when the agent is retained therein.

In some embodiments, the device further comprises an attachment mechanism on the outer side of the back face that is configured to couple the device to an object. In some embodiments, the attachment mechanism is configured to removably couple the device to an object. In some embodiments, the attachment mechanism comprises a clip or flap member that extends from the back face.

In some embodiments, the attachment mechanism comprises an adhesive layer overlying at least a portion of the outer side of the back face configured to removably couple the device to a surface. In some embodiments, the adhesive layer comprises a biocompatible adhesive. In some embodiments, the adhesive layer comprises an acrylic-based pressure-sensitive adhesive. In some embodiments, the adhesive layer comprises an adhesive and scrim layer construct that is coupled to the outer side of the back face via the adhesive. In some embodiments, the device further comprises a removable back liner layer extending over the adhesive layer to temporarily cover the adhesive layer.

In some embodiments, the device further comprises an attachment mechanism on the outer side of the front face that is configured to couple the device to an object. In some embodiments, the attachment mechanism on the outer side of the front face is configured to removably couple the device to an object. In some embodiments, the attachment mechanism on the outer side of the front face comprises a clip or flap member that extends from the back face.

In some embodiments, the attachment mechanism on the outer side of the front face comprises an adhesive layer overlying at least a portion of the outer side configured to removably couple the device to a surface. In some embodiments, the adhesive layer on the outer side of the front face comprises a biocompatible adhesive. In some embodiments, the adhesive layer on the outer side of the front face comprises an acrylic-based pressure-sensitive adhesive. In some embodiments, the adhesive layer on the outer side of the front face comprises an adhesive and scrim layer construct that is coupled to the outer side of the front face via the adhesive. In some embodiments, the device further comprises a removable front liner layer extending over the adhesive layer to temporarily cover the adhesive layer on the outer side of the front face.

In some embodiments, the at least one reservoir layer contains a volume of the agent absorbed and retained therein. In some embodiments, the at least one reservoir layer is void of the agent, and wherein the device further comprises container of the agent for selectively applying the agent to an inner side of the at least one reservoir layer. In some embodiments, when the agent is contained within the at least one reservoir layer, the device is configured such that no more than 5 grams of the agent evaporates over 1.5 hours in an ambient environment of non-moving air at 20 degrees Celsius.

In some embodiments, the agent comprises a sanitizing disinfectant. In some embodiments, the disinfectant is a biocompatible disinfectant. In some embodiments, the disinfectant comprises ethyl, isopropyl, ethanol (ethyl alcohol), triclosan, triclocarban, benzalkonium chloride, benzethonium chloride or a combination thereof. In some embodiments, the disinfectant comprises ethanol (ethyl alcohol).

In some embodiments, the agent comprises a medicant or vitamin. In some embodiments, the agent comprises an insecticide. In some embodiments, the agent comprises a fragrance. In some embodiments, the agent comprises a food product. In some embodiments, the agent comprises a cleaning product. In some embodiments, the agent comprises a paint. In some embodiments, the agent comprises an oil. In some embodiments, the agent comprises a dynamic viscosity within the range of about 4 (Pa·s)(m2/s) and about 15 (Pa·s)(m2/s) at 20 degrees Celsius.

In some embodiments, the least one reservoir dispenser layer comprises at least one dispenser layer comprising a plurality of solid portions and an array of a plurality of openings extending through a thickness thereof, the at least one dispenser layer configured to inhibit evaporation of the agent, and control a flow of the agent from the least one reservoir dispenser layer upon the compression of the least one reservoir dispenser layer in a thickness direction when the agent is contained within the least one reservoir dispenser layer.

In some embodiments, the at least one dispenser layer defines an inner most surface of the least one reservoir dispenser layer and is exposed to the internal cavity. In some embodiments, the at least one dispenser layer comprises a sheet of material that is impervious to the agent. In some embodiments, the at least one dispenser layer comprises a sheet of material that is impervious to air. In some embodiments, the at least one dispenser layer comprises a polymer layer. In some embodiments, the at least one dispenser layer comprises at least one polyethylene layer, polypropylene layer, styrene layer, polyetheretherketone layer, acrylic layer, polyvinyl chloride layer, polyurethane layer, Teflon (Polytetrafluoroethylene) layer, syrlyn layer or a combination thereof. In some embodiments, the solid portions of the at least one dispenser layer comprise within the range of about 10% and about 65% of the total area of the outer face. In some embodiments, the plurality of openings of the at least one dispenser layer comprise an average total area within the range of about 50 mm$^2$ and about 300 mm$^2$ at the outer face. In some embodiments, each of the plurality of openings of the at least one dispenser layer comprise a total area within the range of about 0.05 mm$^2$ and about 0.3 mm$^2$ at the outer face.

In some embodiments, the least one reservoir dispenser layer comprises at least one reservoir layer that is configured to absorb and retain the agent therein. In some embodiments, the at least one reservoir layer underlies the at least one dispenser layer.

In some embodiments, the at least one reservoir layer comprises one or more layers of a fabric, Gore-Tex, gauze, an absorbing gel, a polymer, paper, a foam or a combination thereof. In some embodiments, the at least one reservoir layer comprises one or more layers of polymer fibers, cotton fibers, silicone fibers, hydrogel or a combination thereof. In some embodiments, the at least one reservoir layer comprises a fabric layer of non-woven polymer fibers. In some embodiments, the at least one reservoir layer comprises a layer of non-woven polyethylene and/or polypropylene fibers. In some embodiments, the at least one reservoir layer comprises a natural or synthetic non-woven fabric layer.

In some embodiments, the at least one reservoir layer is configured to absorb and retain within the range of about 2 grams and about 50 grams of the agent. In some embodiments, the at least one reservoir layer comprises a detached agent capacity within the range of about 1,000 g/mm$^2$ and about 2,500 g/mm$^2$. In some embodiments, the at least one reservoir layer comprises an agent absorbency rate of at least 5 g/sec for at least the first 5 seconds of water contact. In some embodiments, the at least one reservoir dispenser layer is configured such that a compressive force acting in the thickness direction and applied to an exposed inner surface thereof of at least 1 gram/mm$^2$ causes the agent to flow therefrom and onto the exposed inner surface.

In some embodiments, the least one reservoir dispenser layer comprises at least one backer layer underlying at least one reservoir layer, the at least one backer layer being substantially impervious to the agent. In some embodiments, the at least one backer layer is substantially impervious to the agent and to air. In some embodiments, the at least one backer layer comprises a solid sheet of material. In some embodiments, the at least one backer layer comprises a polymer layer. In some embodiments, the at least one backer layer comprises at least one polyethylene layer, polypropylene layer, styrene layer, polyetheretherketone layer, acrylic layer, polyvinyl chloride layer, polyurethane layer, Teflon (Polytetrafluoroethylene) layer, syrlyn layer or a combination thereof.

In some embodiments, the front face and/or the back face of the pocket is substantially impervious to the agent. In some embodiments, the front face and/or the back face of the pocket is substantially impervious to the agent and to air. In some embodiments, the front face and/or the back face of the pocket comprises a solid sheet of material. In some embodiments, the front face and/or the back face of the pocket comprises a polymer layer. In some embodiments, the front face and/or the back face of the pocket comprises at least one polyethylene layer, polypropylene layer, styrene layer, polyetheretherketone layer, acrylic layer, polyvinyl chloride layer, polyurethane layer, Teflon (Polytetrafluoroethylene) layer, syrlyn layer or a combination thereof.

In some embodiments, the at least one reservoir dispenser layer comprises a total thickness within the range of about 0.05 mm and about 3 mm. In some embodiments, an inner portion of the at least one reservoir dispenser layer defines a first maximum thickness, and a peripheral edge portion of the at least one reservoir dispenser layer extending about the inner portion and defining an outer extent of the at least one reservoir dispenser layer defines a second thickness that is less than the first thickness.

In some embodiments, the at least one reservoir dispenser layer comprises at least one dispenser layer and at least one reservoir layer bonded together. In some embodiments, the at least one dispenser layer overlies the at least one reservoir layer, and the at least one reservoir layer is bonded to the inner face or outer face. In some embodiments, the at least one reservoir layer, the at least one dispenser layer and the inner face or outer face are heat, radio-frequency or ultrasonic welded together at the peripheral edge portion of the patch. In some embodiments, the at least one reservoir dispenser layer comprises a plurality of sublayers coupled together.

In some embodiments, further comprising a volume of the agent. In some embodiments, the volume of the agent is absorbed within the at least one reservoir dispenser layer. In some embodiments, the volume of the agent is contained within a manually breakable shell or envelope. In some embodiments, the shell or envelope is contained within, or positioned to, the at least one reservoir dispenser layer. In some embodiments, the device is configured as an on-demand agent dispensing pocket patch.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits and advantages described herein.

These and other objects, features and advantages of this disclosure will become apparent from the following detailed description of the various aspects of the disclosure taken in conjunction with the accompanying drawings.

In another aspect, the present disclosure provides a dispensing device comprising: an attachment portion comprising an attachment surface that is configured to removably affix the device to an object; and a reservoir and dispenser portion coupled to and overlying at least a portion of the attachment portion, the reservoir and dispenser portion containing a volume of an agent and configured to control a dispense rate of the agent to a user at an exposed outer dispenser surface portion thereof when the user touches the outer surface portion.

In some embodiments, the attachment portion is configured to directly removably attach to skin of a user. In some embodiments, the attachment portion comprises a biocompatible adhesive layer that forms the attachment surface. In some embodiments, the biocompatible adhesive comprises a biocompatible pressure sensitive adhesive. In some embodiments, the attachment portion further comprises a removably protective film extending over the biocompatible adhesive.

In some embodiments, the attachment portion is configured to removably attach to an inanimate object. In some embodiments, the attachment portion comprises an adhesive and/or at least mechanical connector configured to removably attach to the inanimate object and that forms the attachment surface.

In some embodiments, the attachment portion comprises a carrier layer. In some embodiments, the carrier layer comprises at least one layer comprises of a fabric, plastic or latex, and wherein the attachment surface is formed by an attachment mechanism coupled to the carrier layer. In some embodiments, the carrier layer comprises a water absorbable and/or air permeable fabric layer. In some embodiments, the fabric layer comprises a woven nylon layer, a woven polyester layer, Gore-Tex layer or a combination thereof.

In some embodiments, the attachment portion and the reservoir and dispenser portion are flexible. In some embodiments, the reservoir and dispenser portion comprises a single layer. In some embodiments, the reservoir and dispenser portion comprises at least one reservoir layer or portion that contains the volume of the agent and at least one dispenser layer or portion that forms the outer dispenser surface portion, the at least one reservoir layer or portion and the at least one dispenser layer or portion being separate and distinct from each other. In some embodiments, the reservoir and dispenser portion comprises a waterproof layer.

In some embodiments, the volume of the agent is absorbed into the reservoir and dispenser portion. In some embodiments, the reservoir and dispenser portion defines at least one inner cavity that contains the volume of the agent. In some embodiments, the volume of the agent comprises a plurality of distinct agent portions distributed within the reservoir and dispenser portion. In some embodiments, the plurality of distinct agent portions comprise capsulated agent portions.

In some embodiments, the reservoir and dispenser portion comprises one or more layers of a fabric, Gore-Tex, gauze, absorbing gel, plastic, paper, foam or a combination thereof. In some embodiments, the reservoir and dispenser portion comprises one or more fabric layers formed of cotton, nylon, polyester or a combination thereof.

In some embodiments, the reservoir and dispenser portion comprises a plurality of selectively removably attached stacked layers each with an upper surface that forms the outer dispenser surface portion when positioned as the uppermost layer. In some embodiments, a pore/perforation size, pore/perforation arrangement, density, thickness, and capillary action of the reservoir and dispenser portion is configured to control the amount of the agent that travels through the reservoir and dispenser portion and to outer dispenser surface portion.

In some embodiments, the agent is a liquid and/or gel. In some embodiments, the agent is solid.

In some embodiments, the agent is a disinfectant. In some embodiments, the disinfectant is a biocompatible disinfectant. In some embodiments, the disinfectant comprises ethyl, isopropyl, ethanol (ethyl alcohol), triclosan, triclocarban, benzalkonium chloride, benzethonium chloride or a combination thereof. In some embodiments, the disinfectant comprises ethanol (ethyl alcohol). In some embodiments, the agent comprises an essential oil. In some embodiments, the agent comprises a medicant or vitamin. In some embodiments, the agent comprises an insecticide. In some embodiments, the agent comprises a fragrance. In some embodiments, the agent comprises a food product. In some embodiments, the agent comprises a cleaning product. In some embodiments, the agent comprises a paint.

In some embodiments, the device further comprises a cover layer overlying the outer dispenser surface portion and removably attached thereto. In some embodiments, an outer dispenser surface portion of the cover layer comprises a visual and/or tactile indication and/or is configured to display a visual indication. In some embodiments, the device further comprises a backer layer overlying the attachment portion and removably attached thereto. In some embodiments, the outer dispenser surface portion of the cover layer comprises at least one of a visible light reflective material or an illumination device thereon.

In some embodiments, the reservoir and dispenser portion is configured to change color between at least two differing total volumes of the agent contained therein. In some embodiments, the reservoir and dispenser portion comprises a plurality of removably coupled overlying reservoir and dispenser layers that each contain a volume of the agent, and wherein the upper most reservoir and dispenser layer forms the outer dispenser surface portion. In some embodiments, the reservoir and dispenser portion comprises at least one reservoir area and at least one dispensing area that is spaced from the at least one reservoir area, and wherein the at least one dispensing area forms the outer dispenser surface portion. In some embodiments, the at least one reservoir area comprises a compressible internal cavity that contains the volume of the agent and at least one channel that defines a pathway for the flow of the agent from the internal cavity to the at least one dispensing area.

In some embodiments, the device is elongated and rolled upon itself into a spiral form.

In some embodiments, the device comprises a pocket with an internal cavity, and the reservoir and dispenser portion is positioned within the internal cavity of the pocket. In some embodiments, the attachment portion comprises a backside of the internal cavity of the pocket.

In another aspect, the present disclosure provides a method of disinfecting a surface. The method comprises obtaining any of the devices discussed, wherein the agent of the device comprises a topical disinfectant; removably affixing the attachment portion of the device to an object; and transferring a portion of the disinfectant from the device via the outer dispenser surface portion to the surface.

In some embodiments, the transferring the portion of the disinfectant from the device to the surface comprises engaging the outer dispenser surface portion and the surface. In some embodiments, the transferring the portion of the disinfectant from the device to the surface comprises manually touching the outer dispenser surface portion to dispense the portion of the disinfectant, and manually transferring at least some of the dispensed portion of the disinfectant to the surface.

In another aspect, the present disclosure provides a disinfectant construct comprising a flexible and porous polymer member comprising internal voids in communication with an outer dispenser surface portion, and a disinfectant contained within the internal voids of the member.

In some embodiments, the disinfectant is naturally drawn to the outer dispenser surface portion from within the internal voids due to capillary action. In some embodiments, the polymer member comprises silicone, polyurethane, hydrogel or a combination thereof. In some embodiments, the disinfectant is a liquid and/or gel biocompatible disinfectant.

In some embodiments, the member is thin and elongated. In some embodiments, the member is arranged in a rolled arrangement.

In some embodiments, the construct further comprises an adhesive or attachment mechanism coupled to a backside of the member. In some embodiments, the adhesive or attachment mechanism is configured affix the member to an outer surface of an object.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits and advantages described herein.

These and other objects, features and advantages of this disclosure will become apparent from the following detailed description of the various aspects of the disclosure taken in conjunction with the accompanying drawings.

BRIEF DESCRIPTION OF THE DRAWINGS

These and other features, aspects, and advantages of the present disclosure will become better understood when the following detailed description is read with reference to the accompanying drawings. It should be understood that at least some of the drawings are not necessarily to scale (but at least some of the drawings may be drawn to scale). In certain figures, details that are not necessary for an understanding of the disclosure or that render other details difficult to perceive may have been omitted. It should be understood, of course, that the disclosure is not necessarily limited to the particular embodiments illustrated in the figures. Like reference numerals are utilized throughout the figures to represent like aspects illustrated in the drawings, wherein:

FIGS. 5A-5M illustrates varying views of an on-demand disinfectant dispensing device according to FIG. 1 removably affixed to active skin areas of a user according to one embodiment of the present disclosure.

FIGS. 6A and 6B illustrate perspective top and bottom views, respectively, a side cross-sectional view of the on-demand disinfectant dispensing device of FIG. 1 including seal and backing layers according to one embodiment of the present disclosure.

FIG. 14 illustrates a side cross-sectional view of the on-demand disinfectant dispensing device of FIG. 13 extending through a defined disinfectant flowpath according to one embodiment of the present disclosure.

FIG. 15 illustrates a side cross-sectional view of the on-demand disinfectant dispensing device of FIG. 13 offset from the at least one defined disinfectant flowpath according to one embodiment of the present disclosure.

DETAILED DESCRIPTION OF THE DRAWINGS

Figure 1:
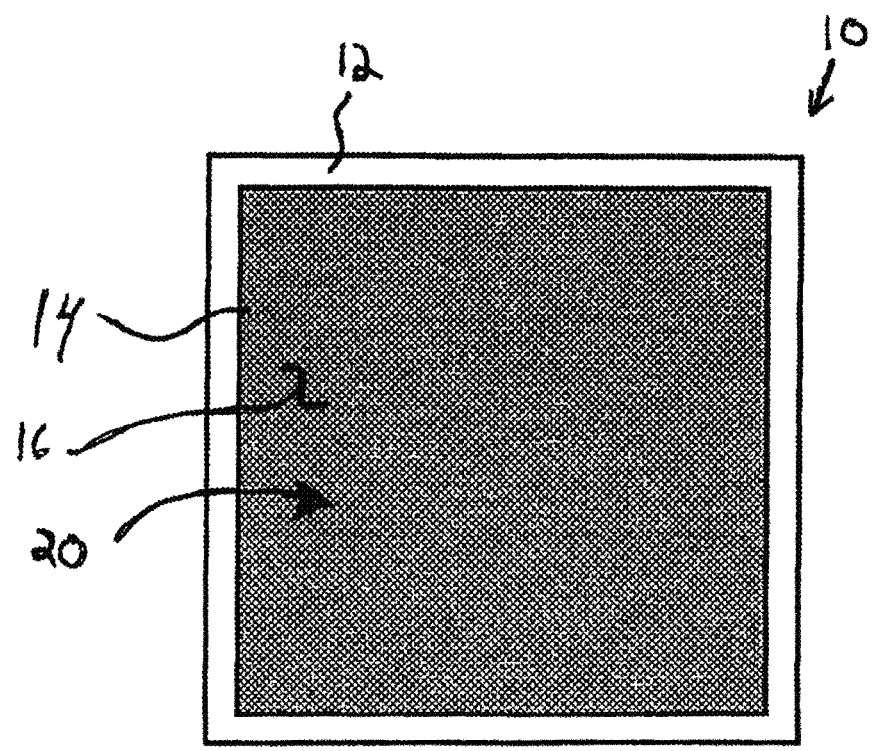
FIG. 1 illustrates a top view of an on-demand disinfectant dispensing device according to one embodiment of the present disclosure.

Aspects of the present disclosure and certain examples, features, advantages, and details thereof, are explained more fully below with reference to the non-limiting examples illustrated in the accompanying drawings. Descriptions of well-known components, aspects, materials, chemicals, fabrication mechanisms, processing techniques, uses, etc., are omitted so as not to unnecessarily obscure the relevant details. It should be understood, however, that the detailed description and the specific examples, while indicating aspects of the disclosure, are given by way of illustration only, and are not by way of limitation. Various substitutions, modifications, additions, and/or arrangements, within the spirit and/or scope of the underlying inventive concepts will be apparent to those skilled in the art from this disclosure.

Approximating language, as used herein throughout disclosure, may be applied to modify any quantitative representation that could permissibly vary without resulting in a change in the basic function to which it is related. Accordingly, a value modified by a term or terms, such as "terms "substantially", "approximately", "about", "relatively," or other such similar terms is not limited to the precise value specified, and is used to describe and account for small fluctuations, such as due to variations in processing, from a reference or parameter. Such small fluctuations include a zero fluctuation from the reference or parameter as well. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%. In some instances, the approximating language may correspond to the precision of an instrument for measuring the value.

Terminology used herein is for the purpose of describing particular examples only and is not intended to be limiting. As used herein, the singular forms "a", "an" and "the" are intended to include the plural forms as well, unless the context clearly indicates otherwise. Furthermore, references to "one example" are not intended to be interpreted as excluding the existence of additional examples that also incorporate the recited features. Moreover, unless explicitly stated to the contrary, the terms "comprising" (and any form of "comprise," such as "comprises" and "comprising"), "have" (and any form of "have," such as "has" and "having"), "include" (and any form of "include," such as "includes" and "including"), and "contain" (and any form of "contain," such as "contains" and "containing") are used as open-ended linking verbs. As a result, any examples that "comprises," "has," "includes" or "contains" one or more step or element possesses such one or more step or element, but is not limited to possessing only such one or more step or element. As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable or suitable. For example, in some circumstances, an event or capacity can be expected, while in other circumstances the event or capacity cannot occur—this distinction is captured by the terms "may" and "may be."

As used herein and unless otherwise indicated, the term "entirety" (and any other form of "entire") means at least a substantial portion, such as at least 95% or at least 99%. The term "entirety" (and any other form of "entire"), as used herein, is thereby not limited to 100%, unless otherwise indicated.

The terms "disinfecting," "sanitizing" and "sterilizing" (and the equivalents thereof) are used synonymously herein to refer to the action of trappings, removing, killing, or inhibiting the growth and/or reproduction of a pathogen (i.e., an infectious disease-causing microorganism, such as various viruses, bacteria, fungus, and parasites). Similarly, the terms "disinfectant," "sanitizer," "sterilizer," "antimicrobial" and "antiseptic" (and the equivalents thereof) are used synonymously herein to refer to a substance that disinfects (i.e., that traps, removes, kills, or inhibits the growth and/or reproduction of a pathogen). The term "topical" is used herein to refer to a disinfectant that disinfects pathogens located on (the outside of) one's skin or the outer/exterior surface of an inanimate object).

The terms "affix," "connect" "contact," "coupled" and/or the like are broadly defined herein to encompass a variety of divergent arrangements and assembly techniques. These arrangements and techniques include, but are not limited to (1) the direct joining of one component and another component with no intervening components therebetween (i.e., the components are in direct physical contact); and (2) the joining of one component and another component with one or more components therebetween, provided that the one component being "affixed to," "connected to," "contacting" or 'coupled to" the other component is somehow in operative communication with the other component (notwithstanding the presence of one or more additional components therebetween). It is to be understood that some components that are in direct physical contact with one another may or may not be in fluid contact with one another. Moreover, two components that are fluidly/fluidically connected, fluidly/fluidically coupled or in fluid/fluidic communication may or may not be in direct physical contact, and one or more other components may be positioned therebetween.

The present disclosure provides for on-demand disinfectant dispensing devices, and disinfecting methods utilizing such devices, that can be removably affixed to an object (such as a user or a surface of an inanimate object) that provide easy, available access to a supply of a disinfectant over an extended period of time. The on-demand disinfectant dispensing devices thereby provide for disinfection of a user's body (e.g., the skin of a user's hand), as well as potential transfer of the disinfectant to, and thereby disinfection of, the skin of at least one other person and/or a surface of an inanimate object via touching thereof by the user after use/application of the disinfectant. The efficient (e.g., one step) on-demand disinfectant dispensing devices and methods are thereby able to efficiently provide an on-demand disinfectant (e.g., via single step, for example) to one or more people and/or surfaces.

The on-demand disinfectant dispensing devices provide a simple, cost effective way to reduce the spread of pathogens/infectious disease. The devices are self-contained, are void of bottles that need to be carried and opened, include a no spill solution, and do not necessitate pouring or spraying for use. As noted above, the on-demand disinfectant dispensing devices may be configured to be removably affixed to a user, such as to the user's skin or the user's clothing (or any other inanimate object carried or worn by the user). In such a configuration, the on-demand disinfectant dispensing device provides a no fuss anti-bacterial action wearable device. The on-demand disinfectant dispensing wearable devices may be configured to be removably affixed to an active point/portion of contact of the user that would benefit from being disinfected, such as on the inside of a user's hand (e.g., on the palm and/or fingers), to target one or more locations on one's body for an added level of protection and peace of mind. In this way, the active on-demand disinfectant dispensing wearable device can be applied over the active portion of the user (e.g., a user's elbow, palm, finger, etc.) and replace the portion with a disinfectant dispensing surface and thereby a disinfected/sterile surface.

In some other embodiments, the on-demand disinfectant dispensing wearable device may be configured to be removably affixed to a passive portion of the user's skin (or an object worn/carried by the user) (or on an inanimate object remote from the user) that is spaced from the point/portion of contact of the user, to allow for selective application of the disinfectant on the portion of contact of the user by passing the portion of contact of the user on/over the device. For example, a passive on-demand disinfectant dispensing wearable device may be removably affixed to the back of a user's hand or forearm, or on their clothing, and the user may wipe their finger(s)/hand on/over the exposed dispensing surface of the device to apply the disinfectant thereto (and thereby disinfect their finger(s)/hand). In such a passive disinfecting embodiment, the on-demand disinfectant dispensing wearable device provides quick and discrete on-demand access to a disinfectant where swiping/contacting the device disinfects a person's point/portion of contact (e.g., their hand(s) or other skin surface).

The on-demand disinfectant dispensing devices disclosed herein can thereby be applied to an active or passive surface portion of a user (or an object) to disinfect it, and, potentially, pass it on to a third party that subsequently touches the surface portion (i.e., pays it forward). In this way, the on-demand disinfectant dispensing devices can provide a level of disinfecting of safety to a user, with the additional benefit of protecting others that may touch the user or even a common surface/object. Communal touchpoints can thus be sanitized and provide an integral part to the health and wellbeing of a community as a whole via the disclosed on-demand disinfectant dispensing devices.

As shown in FIGS. 1-6, in some embodiments a disinfectant dispensing device 10 according to the present disclosure includes an attachment portion 12 and a disinfectant reservoir and dispenser portion 16

The attachment portion 12 may comprise an attachment surface 17 that is configured to affix/couple the device 10 to an object (removably or fixedly) (e.g., a user skin or a surface of an inanimate object, as described above and further below). The disinfectant reservoir and dispenser portion 14 is coupled to and overlies at least a portion of the attachment portion, as shown in FIGS. 1-6. As also shown in FIGS. 1-6, the disinfectant reservoir and dispenser portion 14 contains a volume of disinfectant 20. The disinfectant reservoir and dispenser portion 14 is configured to control a dispense rate (i.e., time release) of the volume of topical disinfectant 20 to a user at an exposed outer dispensing surface portion 16 thereof when a user touches the outer dispensing surface portion 16. In some embodiments, the disinfectant reservoir and dispenser portion 14 may be refillable.

The device 10 (e.g., the attachment portion 12 and the disinfectant reservoir and dispenser portion 14) may be of any size and any shape. In some embodiments, the device may be relatively flat or thin in a thickness direction (e.g., comprise a patch, sheet or like arrangement). In some embodiments, the size and/or shape of the device 10 may correspond to a particular surface/object to which is can be removably coupled to. In this way, the device 10 may be configured to a particular usage (e.g., shaped and sized to removably attach to a particular object or body portion of a user). The device 10 (e.g., the attachment portion 12 and the disinfectant reservoir and dispenser portion 14) may be relatively flexible, such as easily manually flexible.

Figure 2:
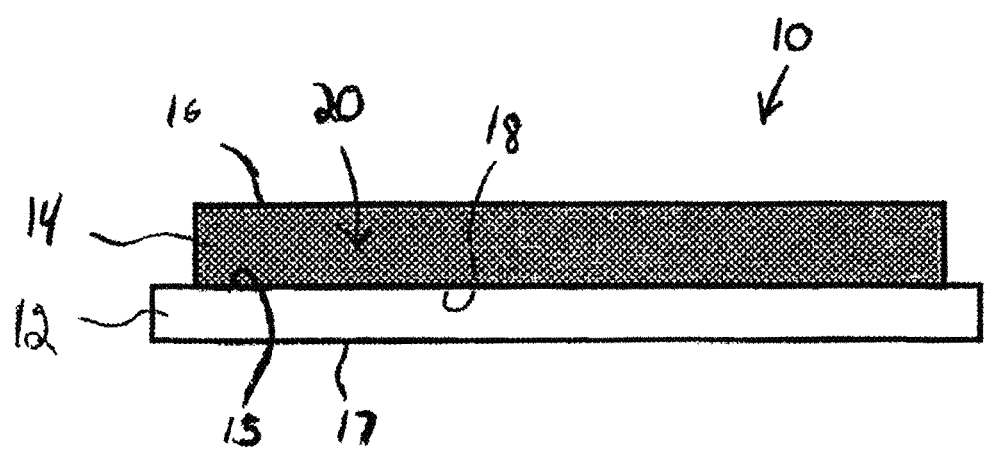
FIG. 2 illustrates a side cross-sectional view of the on-demand disinfectant dispensing device of FIG. 1 according to one embodiment of the present disclosure.

As shown in FIGS. 2 and 6, the attachment portion 12 may define the backside or underside of the device 10, and include a backside attachment surface 17 that is configured to abut or overly another surface when the device 10 is coupled thereto. In some embodiments, the attachment portion 12 may include an adhesive on (or that forms) the attachment surface 17 that is configured to removably couple the device 10 to a surface. In some other embodiments (not shown), the attachment portion 12 may include a mechanical mechanism to removably attach the device to a surface. For example, the attachment portion 12 may include and/or comprise a strap, hook-and-loop (or hook-and-hook) fastener, snap fastener, button, strap, elastic, suction cup/member, zipper, threaded post/aperture, magnet or any other fastener mechanism that is configured to removably couple the device 10 to another surface/object. It is noted that the particular design and configuration can of the attachment portion 12 can take on any form with respect to a particular surface/object sufficient to removable couple the device 10 to the surface/object.

In some embodiments, the attachment portion 12 may include an adhesive on (or that forms) the attachment surface 17 that is configured to removably couple the device 10 to an inanimate object and/or skin of a user. In some such embodiments, the adhesive may comprise a pressure sensitive adhesive (PSA). In some such embodiments, the attachment portion 12 may be configured to directly removably attach to skin of a user via a biocompatible (and/or medical grade) adhesive, such as a biocompatible PSA, and/or an alcohol resistant adhesive. In some embodiments, the adhesive of the attachment portion 12 may comprise an acrylic adhesive, an epoxy adhesive, a styrene block co-polymer adhesive or a combination thereof. In some such embodiments, the adhesive of the attachment portion 12 may comprise an acrylate, such as methacrylates, epoxy diacrylates (i.e., a vinyl resin) or a combination thereof. In some such embodiments, the adhesive of the attachment portion 12 may comprise spirit gum (mastic), matte spirit gum, liquid latex, thickened latex, flexible collodion or a combination thereof. In some such embodiments, the adhesive may comprise a biodegradable, natural and/or organic adhesive. In some embodiments, the tack, adhesion, shear strength and breathability of the adhesive may be configured such that the device 10 is biocompatible with respect to a user's skin.

Figure 6A:
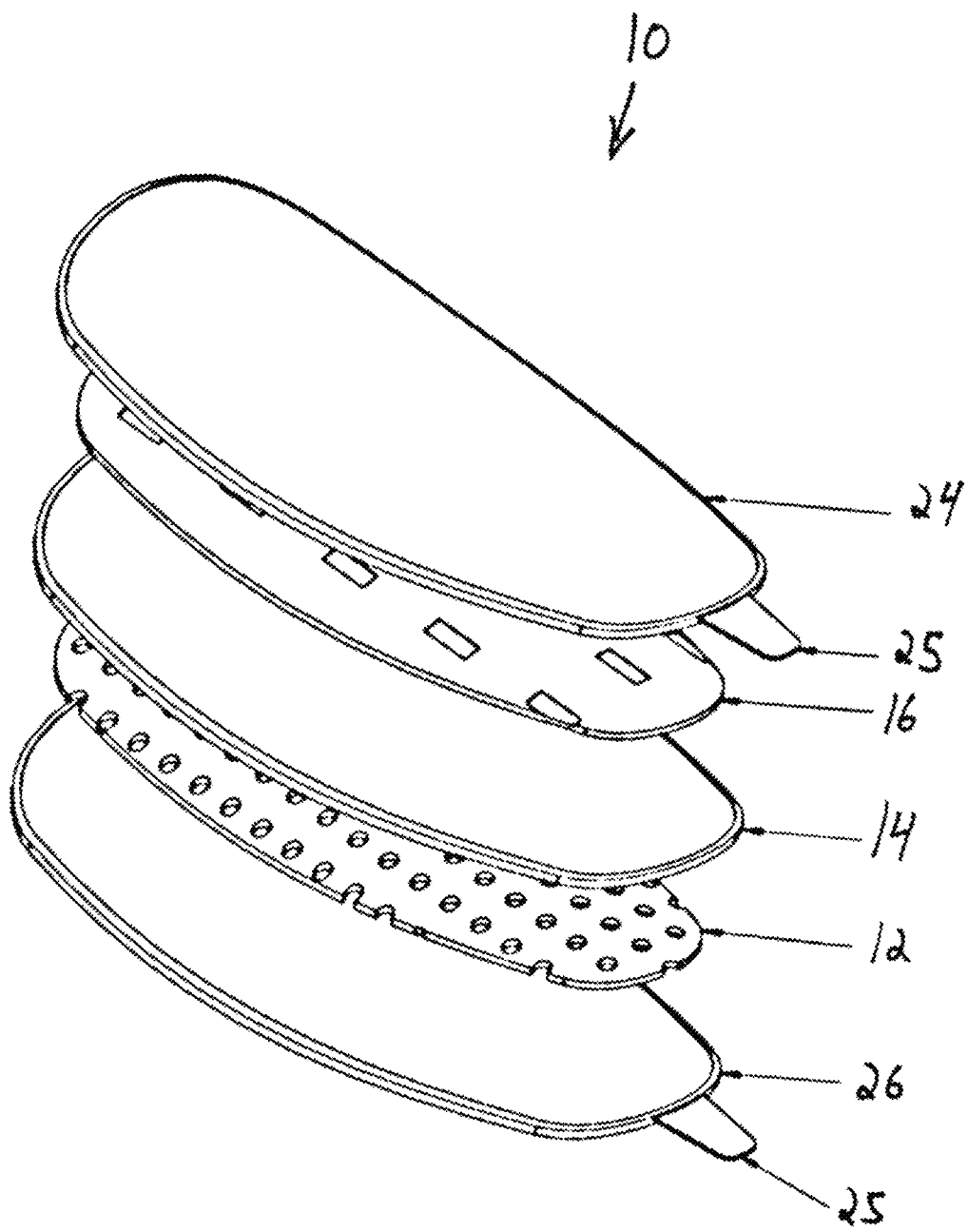

As shown in FIGS. 6A and 6B, in some embodiments, the attachment portion 12 of the device 10 may comprise an adhesive and a removable attachment protective film 26 extending over the attachment surface 17 of the adhesive. The attachment protective film 26 may be configured to cover and protect the adhesive prior to use (or when otherwise not in use). The attachment protective film 26 may thereby be configured to be removable from the adhesive (e.g., peeled off) such that the adhesive remains coupled to the device 10 and is effective in coupling the device 10 to a surface. In some embodiments, the attachment protective film 26 may comprise a plastic/polymer, coated paper, metallic/metalized layer (e.g., a foil layer or aluminized material layer) or a combination thereof. As also shown in FIGS. 6A and 6B, in some embodiment the protective film 26 may include a tab 25 to aide in manually removing (e.g., peeling) the protective film 26 from the attachment surface 17.

In some embodiments, the attachment portion 12 may include at least one carrier or support layer. The carrier layer may support the attachment mechanism (e.g., an adhesive and/or mechanical fastener) (i.e., the attachment mechanism may be coupled to bottom side of the carrier layer). Further, the disinfectant reservoir and dispenser portion 14 may be coupled to and overly (e.g., directly overly) the top side of the carrier layer. In some embodiments, the carrier layer comprises at least one layer of a fabric (woven or nonwoven), plastic or latex. For example, the carrier layer may comprise a breathable fabric, such as a woven (or nonwoven) nylon, polyester or Gore-Tex layer. The carrier layer may be flexible, and may comprise a water absorbable and/or air permeable fabric layer (particularly in embodiments of the device 10 for use directly on the skin of a user, as described further below).

As also shown in FIGS. 6A and 6B, the disinfectant reservoir and dispenser portion 14 of the device 10 may include a dispenser protective film 24 extending over the dispensing surface portion 16. The dispenser protective film 24 may be configured to cover and protect the dispensing surface portion 16, and thereby the volume of disinfectant 20 contained within the disinfectant reservoir and dispenser portion 14, prior to use (or when otherwise not in use). For example, the dispenser protective film 24 may be effective in preventing (or at least substantially inhibiting) evaporation and/or leakage of the disinfectant 20 from the disinfectant reservoir and dispenser portion 14 via the dispensing surface portion 16. The dispenser protective film 24 may thereby be configured to be removable from the dispensing surface portion 16 (e.g., peeled off) such that the disinfectant 20 is able to be dispensed/flow through the dispensing surface portion 16. In some embodiments, the dispenser protective film 24 may comprise a plastic/polymer or metallic/metalized layer (and potentially an adhesive). Removal of the dispenser protective film 24 may thereby activate the device 10/disinfectant reservoir and dispenser portion 14 for use (e.g., begin or initiate wicking and/or capillary action of the disinfectant 20 and/or evaporation of the disinfectant 20 at the exposed dispensing surface portion 16).

In some embodiments, the outer surface of the cover or protective film 24 may include a visual and/or tactile indication (not shown), or be configured such that a visual and/or tactile indication can be drawn or otherwise formed thereon. For example, the outer surface of the protective film 24 may include a logo, name, trademark or other visual indication that may enhance the aesthetic look and/or feel of the device 10. As another example, the outer surface of the cover or protective film 24 may be configured as a paper, chalkboard or whiteboard type configuration to allow for personalization of the device 10. In some embodiments, the outer surface of the cover or protective film 24 comprises at least one of a visible light reflective material and an illumination device thereon. As also shown in FIGS. 6A and 6B, in some embodiment the protective film 24 may include a tab 25 to aide in manually removing (e.g., peeling) the protective film 24 from the dispensing surface portion 16.

The disinfectant reservoir and dispenser portion 14 may comprise one or more layers and/or more materials. In some embodiments, as shown in FIGS. 1 and 2, the disinfectant reservoir and dispenser portion 14 may comprise a single later comprised of one or more materials. In some other embodiments, as discussed further below, the disinfectant reservoir and dispenser portion 14 may comprise one or more disinfectant reservoir layers (or portions) and one or more dispenser layers (or portions) that are separate and distinct from the one or more disinfectant reservoir layers (or portions).

The disinfectant reservoir and dispenser portion 14 is configured to contain the volume of disinfectant 20. For example, the disinfectant 20 may be absorbed into the disinfectant reservoir and dispenser portion 14 (e.g., the disinfectant reservoir and dispenser portion 14 may comprise an absorbent pad, layer or portion). As another example, the disinfectant reservoir and dispenser portion 14 may form at least one cavity, opening or cell that contains the disinfectant 20. The disinfectant reservoir and dispenser portion 14 is also configured to dispense the disinfectant 20 at the dispensing surface portion 16 to a user who touches, such as wipes across, the dispensing surface portion 16. At least a portion of the disinfectant reservoir and dispenser portion 14 thereby automatically controls the speed and duration of the release/flow of the disinfectant at/to the outer dispensing surface portion 16 (and thereby to a user on an on-demand basis). For example, the disinfectant reservoir and dispenser portion 14 may be configured to draw or otherwise provide a portion of the volume of disinfectant 20 at or to the dispensing surface portion 16 such that when a user touches or wipes the dispensing surface portion 16, some of the disinfectant 20 transfers to the user.

In some embodiments, the reservoir and dispensing functions or processes of the reservoir and dispensing functions or processes may be accomplished by a common layer or portion of the disinfectant reservoir and dispenser portion 14 may be accomplished by a common layer or portion of the disinfectant reservoir and dispenser portion 14. In some other embodiments, the reservoir and dispensing functions or processes of the reservoir and dispensing functions or processes may be accomplished by a common layer or portion of the disinfectant reservoir and dispenser portion 14 may be accomplished by differing layers or portions of the disinfectant reservoir and dispenser portion 14. In some embodiments, the disinfectant reservoir and dispenser portion 14 may comprise at least one layer or portion formed of a (woven or non-woven) cloth or fabric (e.g., a cotton, nylon, polyester or the like layer/portion), Gore-Tex, gauze, absorbing gel (e.g., a hydrogel), flashspun high-density polyethylene (e g, Tyvek), porous/filter paper, plastic film, foam, hydrocolloid, alginate, polysaccharide pastes, granules and/or beads, or a combination thereof. For example, is some embodiments the reservoir and dispenser portion 14 may comprise one or more layers of cotton, polyester, silicone, polyurethane, polyamide, polyethylene, hydrogel or a combination thereof. In some such embodiments, the reservoir and dispenser portion 14 may include a cotton fabric layer or portion, a nylon fabric layer or portion, a polyester fabric layer or portion, a flashspun high-density polyethylene fiber layer or portion, a hydrogel layer or portion, a flexible polyamide net coated with silicone layer or portion, a hydrogel layer or portion formed of hydrophilic polymers, or a combination thereof.

At least the dispensing portion of the disinfectant reservoir and dispenser portion 14 may be configured to control the amount and/or rate at which the disinfectant 20 moves or is drawn therethrough (e.g., via capillary action) and to the dispensing surface portion 16. The disinfectant reservoir and dispenser portion 14 is thereby configured to meter/control the release or dispensing of the disinfectant 20 to/from/at the dispensing surface portion 16. For example, at least one of the pore/perforation size, pore/perforation size count/number, density, thickness, and capillary action of the disinfectant reservoir and dispenser portion 14 may be configured to control the amount and/or rate at which the disinfectant 20 moves or is drawn to and through the dispensing surface portion. The disinfectant reservoir and dispenser portion 14 may be configured such that a particular dosage of the disinfectant 20 flows through the disinfectant reservoir and dispenser portion 14 and the dispensing surface portion 16 when a certain pressure (e.g., a certain magnitude, area, direction, etc.) is applied thereto by a user such that the particular dosage of the disinfectant 20 is transferred to the user thereby.

In some embodiments, the device 10, including the disinfectant reservoir and dispenser portion 14 (including the dispensing surface portion 16) and the disinfectant 20, is configured such that the disinfectant 20 is available/dispensable at the dispensing surface portion 16 via touching or swiping of the dispensing surface portion 16 by a user for at least 2 hours, at least 3 hours, at least 4 hours, at least 5 hour or at least 6 hours after the dispensing surface portion 16 is initially exposed.

The volume of disinfectant 20 may be any biocompatible disinfectant (i.e., safe and effective for use with humans, such as on human skin), such as any topical disinfectant effective in killing and/or preventing reproduction of disease causing pathogens (such as viruses and bacteria, for example) when the disinfectant 20 and the pathogens physically interact. The disinfectant 20 may be effective on disinfecting a person's skin and in addition to the surface of an inanimate object (such as a surface comprising plastic, metal, glass, paper, cardboard, etc.). For example, the disinfectant 20 may comprise an alcohol sanitizer and/or an non-alcohol sanitizer. In some embodiments, the disinfectant 20 comprises ethyl, isopropyl, ethanol (ethyl alcohol), triclosan, triclocarban, benzalkonium chloride, benzethonium chloride or a combination thereof. In some embodiments, the disinfectant 20 comprises 1,2-hexanediol, ammonium bicarbonate, ammonium carbonate, benzalkonium chloride, benzalkonium chloride, chlorine dioxide, citric acid, dodecylbenzenesulfonic acid, ethanol, ethyl, glutaraldehyde, glycolic acid, hydrochloric acid, hypochlorous acid, isopropyl, isopropanol, lactic acid, L-lactic acid, octanoic acid, peroxyacetic acid, peroxyoctanoic acid, phenolic, potassium peroxymonosulfate, quaternary ammonium, silver, silver ion, sodium carbonate, sodium carbonate peroxyhydrate, sodium chloride, sodium chlorite, sodium dichloroisocyanurate, sodium dichloroisocyanurate dihydrate, sodium dichloro-S-triazinetrione, sodium hypochlorite, thymol, triethylene glycol, triclosan, triclocarban, alcohol (e.g., at least 60% by volume), aloe gel, vinegar, an essential oil, aromatherapy compound, or a combination thereof, In some embodiments, the disinfectant 20 may comprise at least one essential oil, such as geranium, lavender, sweet marjoram, neroli, palmarosa, peppermint, petitgrain, rose, tea tree, thyme, linalool oil or a combination thereof. In some embodiments, the disinfectant 20 may be in liquid or gel form. In some embodiments, the disinfectant 20 may comprise a solution and/or a suspension, and may include at least solid disinfectants.

It is also specifically disclosed herein that although embodiments of the on-demand dispensing devices (and related methods) of the present disclosure are described with respect to containing and dispensing a disinfectant (i.e., on-demand disinfectant dispensing devices), the devices may equally be employed to dispense any other solid, liquid or gel agent. For example, the devices may contain and be configured to dispense any pleasant or foul odorous and/or tasteful material (e.g., perfume, attractant/dettractant-repellant (e.g., bug or insect repellant, etc.). As another example, the devices may contain and be configured to dispense a skin lotion (e.g., moisturizer, sunscreen, etc.), antiperspirant/deodorant, medication/medicine, lubricant, friction-enhancing material (e.g., a sticky or gritty material), any other biocompatible material, biohazard material or a combination thereof. In some such embodiments, the medication/medicine may be a medicant, a vitamin (vitamin C, B12, etc.) or supplement (e.g., caffeine, nicotine, etc.), a cannabinoid (e.g., cannabidiol (CBD)), delta-9-tetrahydrocannabinol (THC) or a food product (e.g., sugar, candy, etc.). As a further example, the devices may contain and be configured to dispense a paint. As another example, the devices may contain and be configured to dispense a cleaning product. As another example, the devices may contain and be configured to dispense a food product or foodstuff.

Figure 3:
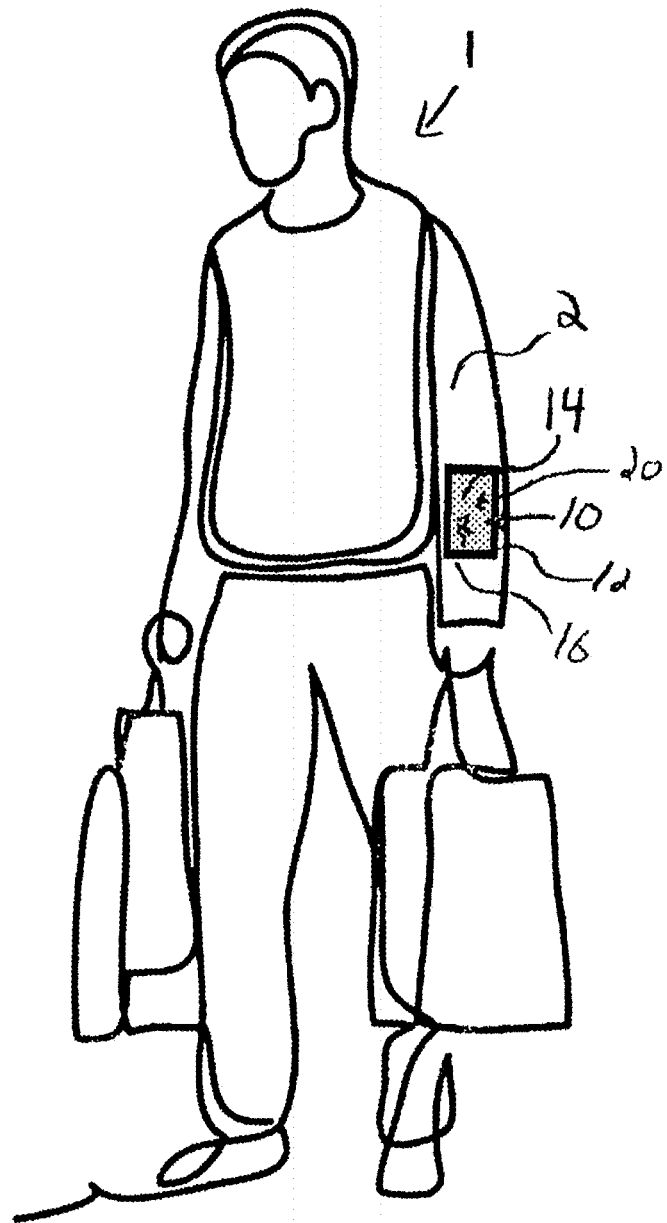
FIG. 3 illustrates a front view of the on-demand disinfectant dispensing device of FIG. 1 removably affixed to an inanimate object worn by a user according to one embodiment of the present disclosure.
Figure 4:
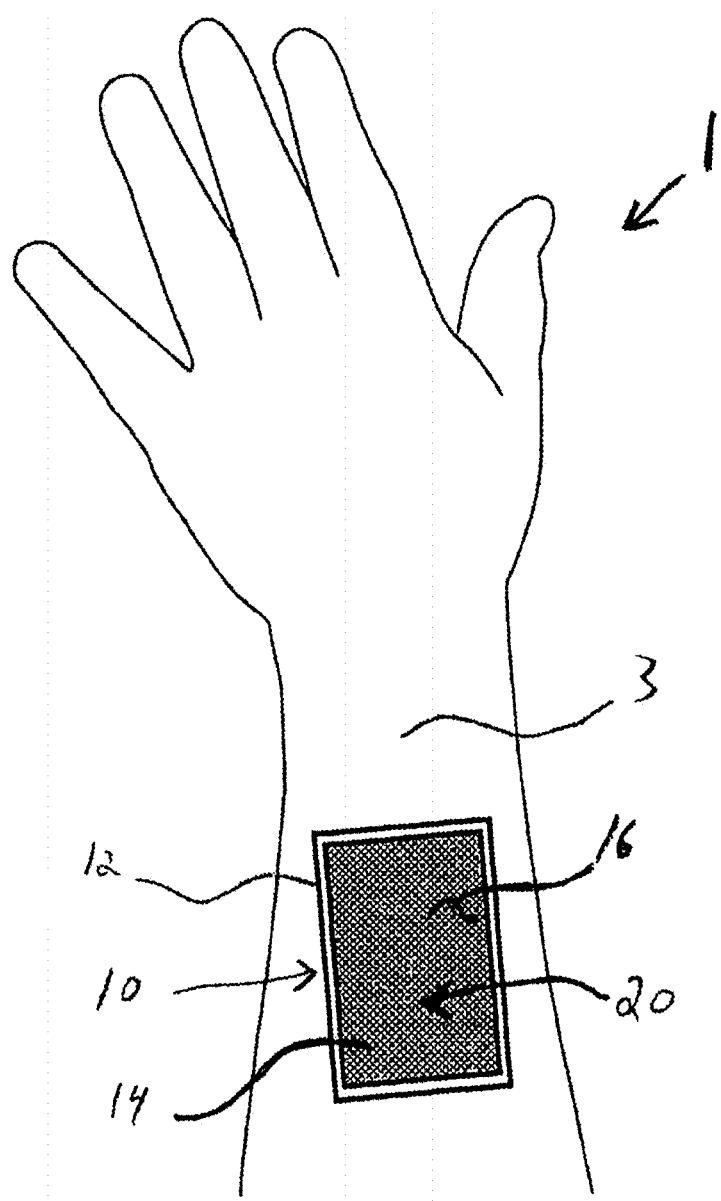
FIG. 4 illustrates a top view of the on-demand disinfectant dispensing device of FIG. 1 removably affixed to a passive skin area of a user according to one embodiment of the present disclosure.

As shown in FIG. 3, in some embodiments, the attachment portion 12 (and potentially the reservoir and dispenser portion 14) may be configured such that the device 10 is worn by a user 1 on a passive piece of clothing (e.g., hat, shirt, coat, pant, belt, shoe, scarf, glove, sock, etc.) or another inanimate object 2 (sweatband, kinesiology/muscle tape, heat/cool pads, helmet, protective pad/brace/splint/cast, headphones, luggage, personal accessories, luggage, wallet, hand bag/purse, athletic equipment, etc.) that is configured to couple to (i.e., be worn or carried by) the user 1. The device 10 may thereby be removably coupled to a passive portion of the user 1 that is spaced from the point/portion of contact of the user 1 that the user wishes to apply the disinfectant 20 to via touching of the dispensing surface portion 16. As noted above, the attachment portion 12 may include and adhesive or mechanical connection mechanism that is configured to attach to a specific or general surface, such as to the clothing 2 or another inanimate object on/coupled to the user 1 as shown in FIG. 3. In use, the user 1 can thereby removably couple the device 10 to their clothing 2 or another inanimate object on/coupled to the user 1 on a passive portion of the user 1 (such as but not limited to over the user's 1 forearm, upper arm, chest, waist or thigh), and touch or wipe the dispensing surface portion 16 with one or more of their hands when the user 1 desires to disinfect their one or more of their hands (or another body portion or inanimate object touched by the user's 1 one or more hand). When the user 1 desires, the device 10 can be removed from the clothing 2 or another inanimate object on/coupled to the user 1 (preferably without damaging the surface outer surface thereof)

As also discussed above and shown in FIG. 4, in some embodiments, the attachment portion 12 (and potentially the reservoir and dispenser portion 14) may be configured such that the device 10 is worn by a user 1 directly on a passive portion of their skin 3. The attachment portion 12 may thereby be configured to be biocompatible with a person's passive skin 3, and the device 10 may be breathable or otherwise resistant to causing the user to sweat beneath the device 12. For example, the device 10 may be configured to have an "invisible" feel when attached to a user's skin 3. The device 10 may thereby be removably coupled to a passive portion of the skin 3 of the user 1 that is spaced from the active portion or point/portion of contact of the user 1 that the user wishes to apply the disinfectant 20 to via touching of the dispensing surface portion 16. In use, the user 1 can thereby removably couple the device 10 directly to their skin 3 on a passive portion of the user 1 (such as but not limited to over the back of the user's hand, forearm, upper arm or thigh), and touch or wipe the dispensing surface portion 16 with one or more of their hands when the user 1 desires to disinfect their one or more of their hands (or another body portion or inanimate object touched by the user's 1 one or more hand). When the user 1 desires, the device 10 can be removed from the skin 3 of the user 1 (preferably without hurting, irritating or otherwise damaging the skin 3).

As shown in FIGS. 5A-5M, in some embodiments, the attachment portion 12 (and potentially the reservoir and dispenser portion 14) may be configured such that the device 10 is worn by a user 1 directly on their active skin 4 or another area/surface of the user 1 to cover/replace the portion (at least partially) by the dispensing surface portion 16. As noted above, the "active" portion 4 of the user 1 may comprise an area that touches/makes contact with at least one other portion of the user 1, another person or an inanimate communal object that will/could be touched by another person to prevent the transmission/passing of a pathogen from the active skin portion/area 4 of the user 1 to the other portion(s) of the user 1 (e.g., the user's 1 eyes, nose or mouth), directly the another person, or indirectly to another person through the communal inanimate object. The attachment portion 12 may thereby be configured to be biocompatible with a person's active skin area 4, and the device 10 may be breathable or otherwise resistant to causing the user to sweat beneath the device 12. The device 10 may be removably coupled to an active skin portion 4 of the user 1 which the user wishes to apply the disinfectant 20 with. In use, the user 1 can thereby removably couple the device 10 directly to an active skin portion 4 of the user 1 (such as but not limited to over the palm and/or finger(s) of the user 1), and the user 1 can touch or wipe the dispensing surface portion 16 as desired to dispense the disinfectant 20. When the user 1 desires, the device 10 can be removed from the active skin portion/area 4 of the user 1 (preferably without hurting, irritating or otherwise damaging the active skin portion/area 4).

Figure 5A:
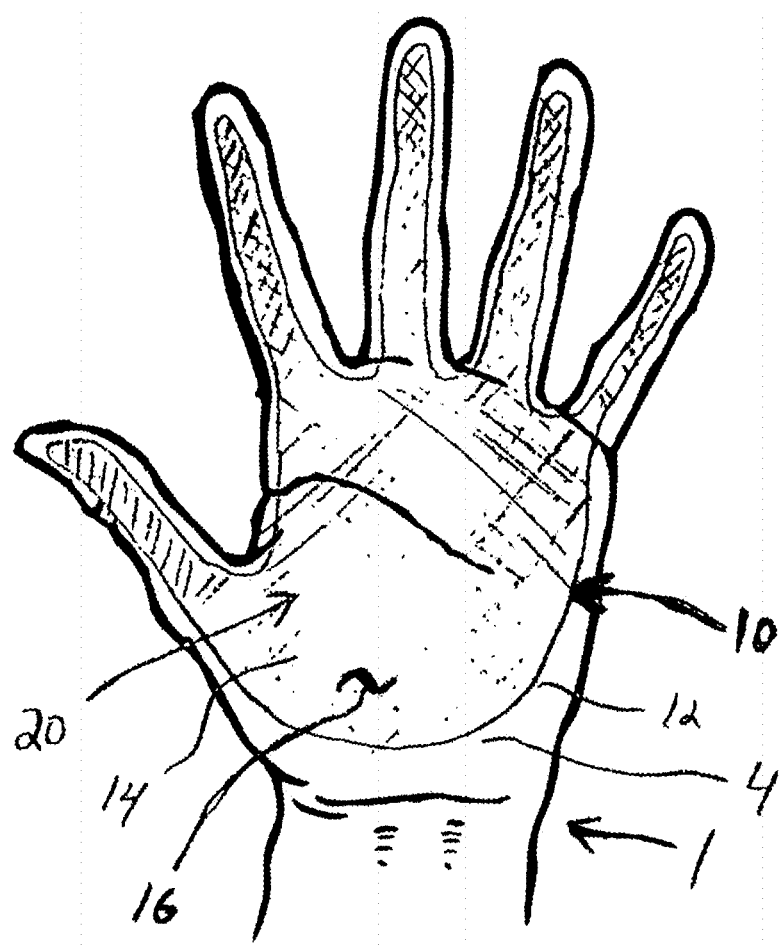
Figure 5B:
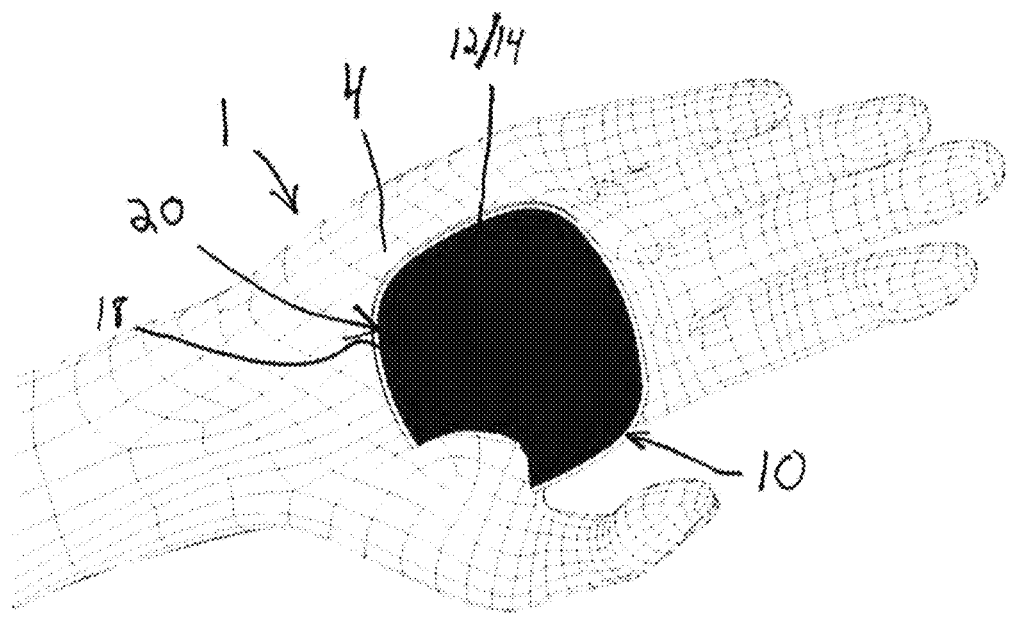
Figure 5C:
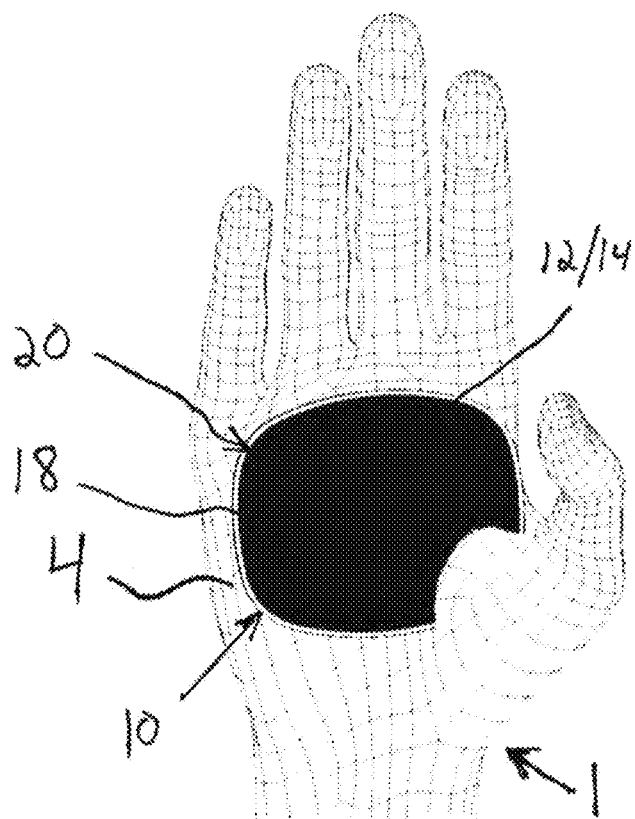
Figure 5D:
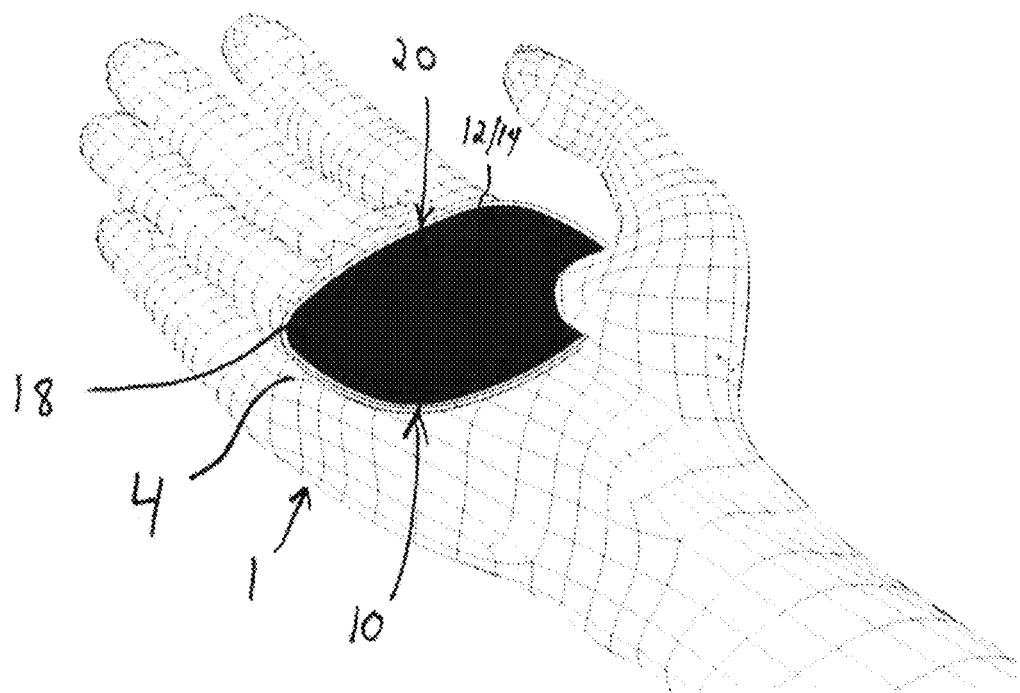
Figure 5E:
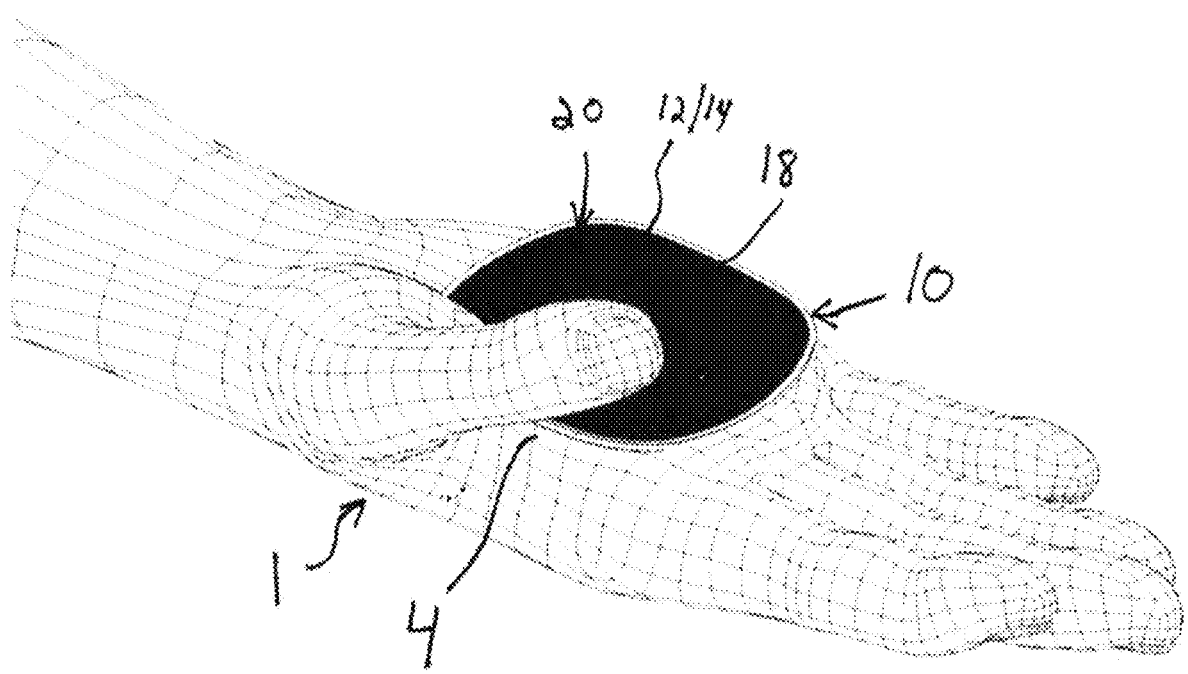
Figure 5F:
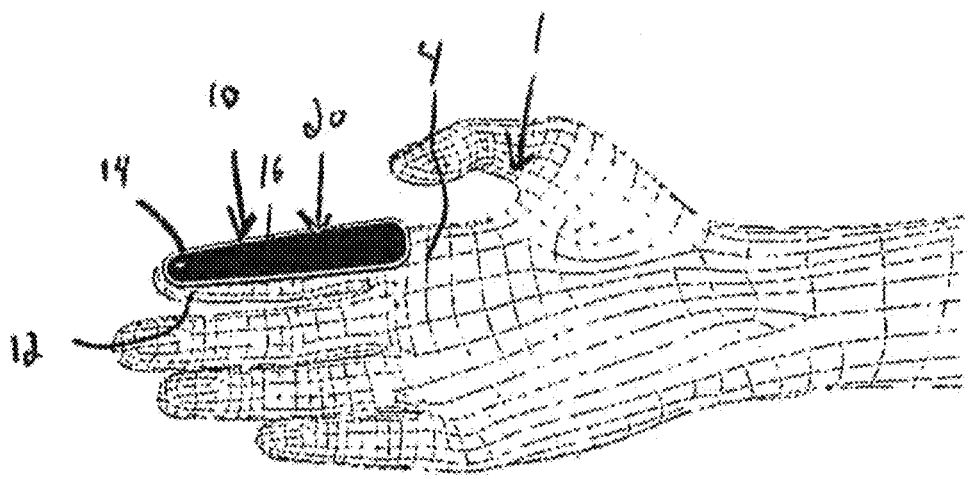
Figure 5G:
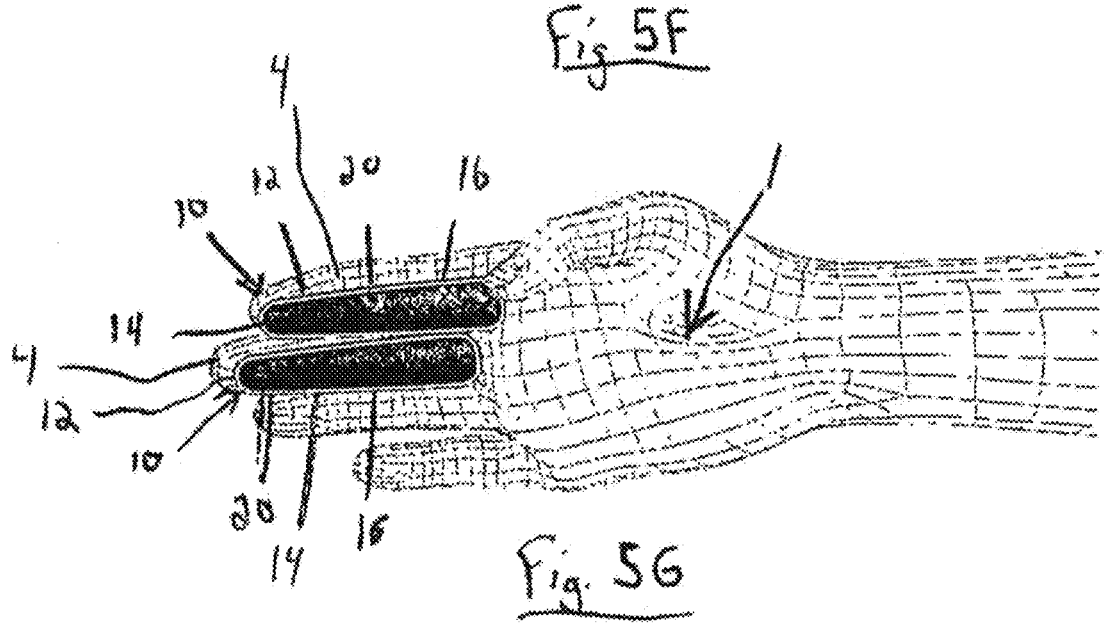
Figure 5H:
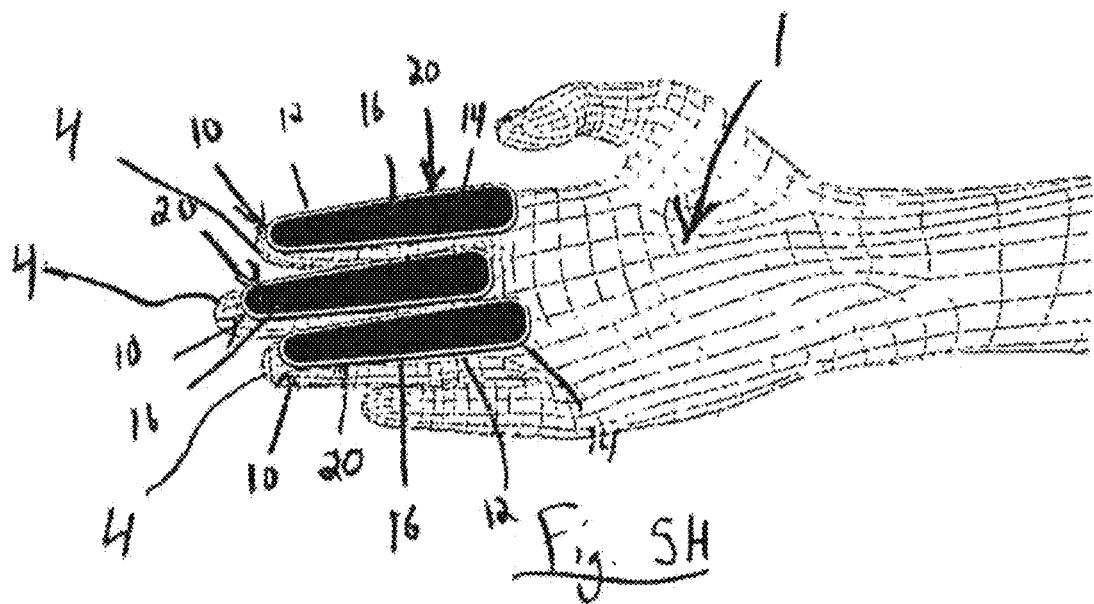
Figure 5K:
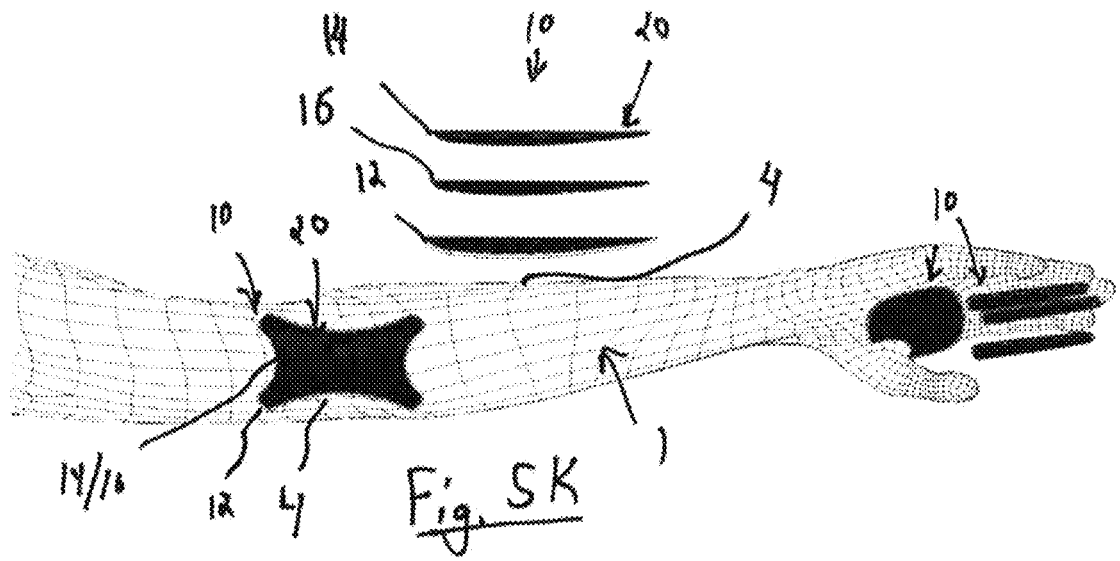
Figure 5L:
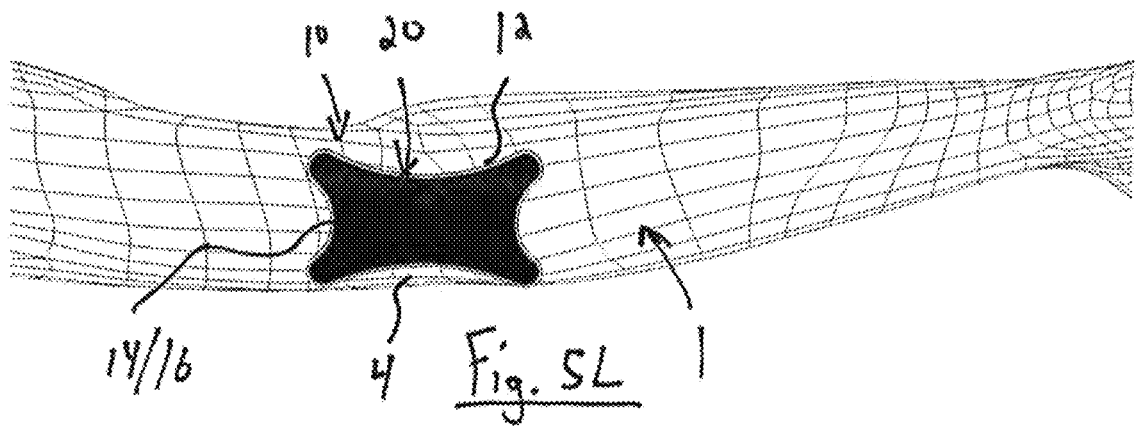
Figure 5M:
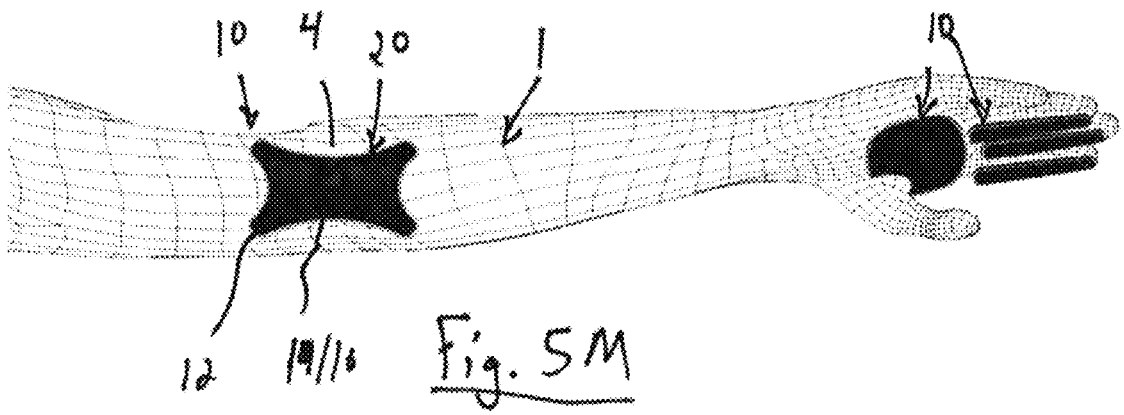

As shown in FIG. 5A, in some exemplary embodiments, the device 10 may be configured (e.g., shaped and sized) to removably couple to and extend over (e.g., cover) the palm and at least a portion of at least one finger 4 of a hand of a user 1. As another example, in some embodiments the device 10 may be configured (e.g., shaped and sized) to removably couple to and extend over (e.g., cover) just a portion of the palm 4 of a hand of a user 1, as shown in FIGS. 5B-5E. In some other exemplary embodiments, the device 10 may be configured (e.g., shaped and sized) to removably couple to and extend over (e.g., cover) at least a portion of an interior side of a finger 4 of a hand of a user 1, as shown in FIGS. 5F-5H. As another example, as shown in FIGS. 5I-5K, in some embodiments the device 10 may be configured (e.g., shaped and sized) to removably couple to and extend over (e.g., cover) just a portion of the forearm 4 of an arm of a user 1. In some other exemplary embodiments, the device 10 may be configured (e.g., shaped and sized) to removably couple to and extend over (e.g., cover) at least a portion of an elbow 4 of an arm of a user 1, as shown in FIGS. 5F-5H.

The device 10 may thus be configured (e.g., shaped and sized) to removably couple to and extend over an area of a user 1 that is likely to contact another individual or a surface that may be contacted by another individual so as to dispense a liquid or gel agent 20, such as but not limited to a disinfectant, thereon/thereto. The device 10 may act as a barrier between the user 1 and the other individual or surface, and also act to carry forward the liquid or gel agent 20 to the other individual or surface.

In yet another embodiment, the device 10, such as at least the attachment portion 12, may be configured to attach to an inanimate object (not shown) that is not worn or carried by a user 1. For example, the attachment portion 12 may be configured to removably (or fixedly) attach to a handle, knob, switch, arm rest, seat, steering wheel, transmission/shift lever, athletic equipment, medical equipment, office equipment, culinary equipment, military/defense equipment, packaging (e.g., a shipping or product packaging), furniture, pet product, or any other item or surface that is communal (i.e., likely to be touched by more than one person) or that is positioned within/near a communal space area, surface or item.

It is specifically noted that embodiments of the device 10 disclosed herein may be configured to attach/couple (removably or fixedly) to any surface of any object (living or inanimate). Embodiments of the device 10 may be used on any surface to provide on-demand access to the disinfectant 20 contained therein for any purpose (such as to provide to directly provide the disinfectant 20 to a surface/portion or indirectly provide the disinfectant 20 to a surface/portion).

Figure 7:
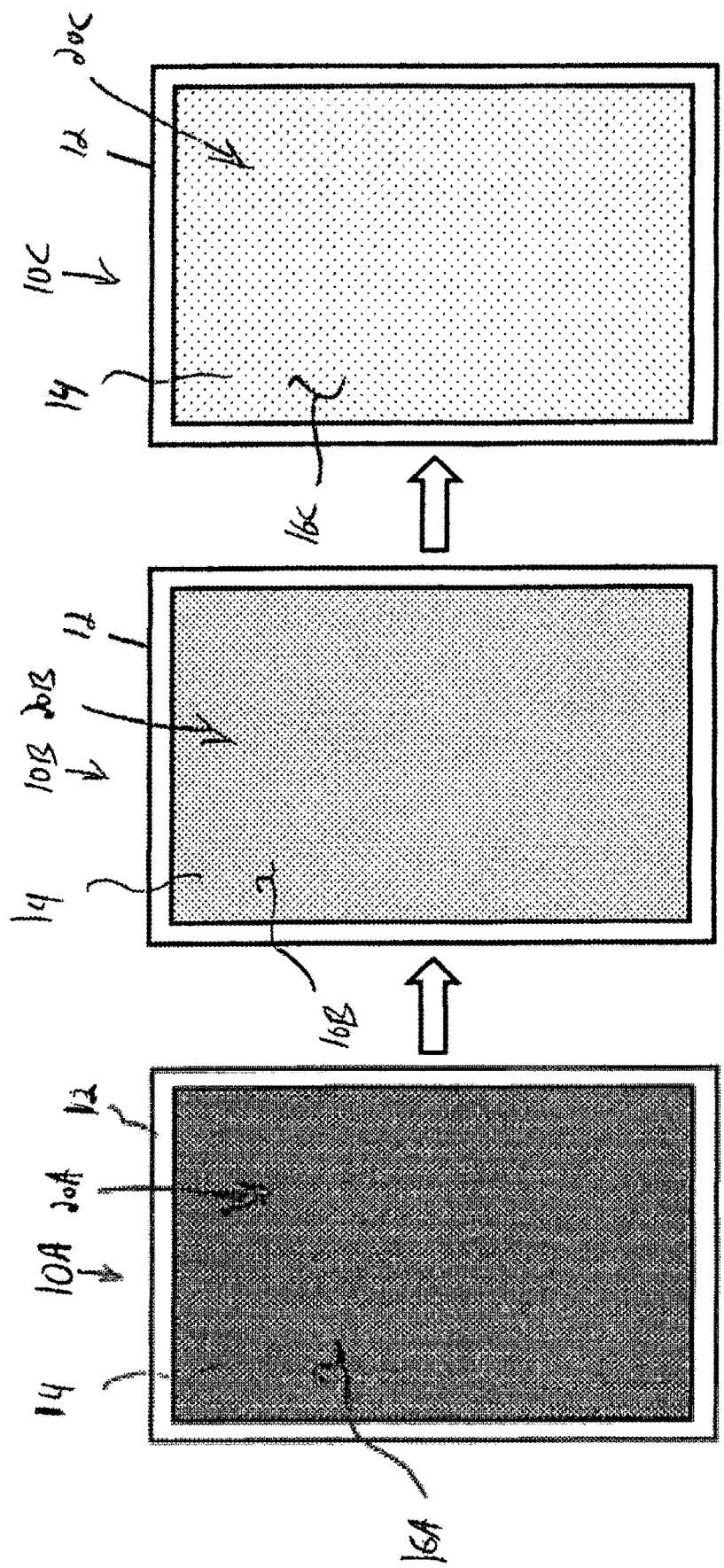
FIG. 7 illustrates a top view of the on-demand disinfectant dispensing device of FIG. 1 as the volume or availability of disinfectant therein lowers over a period of time according to one embodiment of the present disclosure.

In some embodiments, as shown in FIG. 7, the device 10 may be configured such that the appearance of a portion of the device 10, such as the dispensing surface portion 16, changes as the volume of disinfectant 20 within the reservoir and dispenser portion 14. In this way, the device 10 may automatically visually and/or tactically indicate the particular volume of the disinfectant 20 within the reservoir and dispenser portion 14, and thereby available to the user via the dispensing surface portion 16, at any particular time. In this way and as shown in FIG. 7, as a device 10A containing a first "full" volume of the disinfectant 20A transitions to a device 10B containing a second "medium" volume of the disinfectant 20B, the color of at least a portion of the dispensing surface portion 16 (for example) may change. Similarly, as also shown in FIG. 7, as the device 10B containing the second "medium" volume of the disinfectant 20B transitions to a device IOC containing a third "low" volume of the disinfectant 20B (or no available disinfectant 20), the color of at least a portion of the dispensing surface portion 16 (for example) may change again. It is noted that the device 10 may be configured to variably change colors as the volume of the disinfectant 20 changes, or may only change colors once when the level of disinfectant 20 is at least substantially depleted and/or the level available to a user is inadequate to disinfect (for example). For example, the reservoir and dispenser portion 14 and/or the disinfectant 20 may be configured to change color with changes in the temperature, pH and/or dryness/wetness (e.g., liquid vs. solid form) thereof. As the volume of the disinfectant 20 within the reservoir and dispenser portion 14 decreases (such as from being dispensed via the dispensing surface portion 16, to a user and/or evaporating (or otherwise changing states), the temperature, pH and/or dryness/wetness (e.g., liquid/solid state) of the reservoir and dispenser portion 14 and/or the disinfectant 20 may change and cause a color change, such as with respect to a material/component/chemical/additive of or within the reservoir and dispenser portion 14 and/or the disinfectant 20. In some embodiment, the reservoir and dispenser portion 14 and/or the disinfectant 20 may be configured to change color with time, independently of the actual volume of the disinfectant 20. For example, the reservoir and dispenser portion 14 and/or the disinfectant 20 may include a pigment, ink dye or the like that degrades or absorbs over time such that the color thereof changes over time. In this way, the color of the device 10 can indicate to a user how long the device 10 has been in use, and thereby an indication of the potential state of the volume of the disinfectant 20 (e.g., the disinfectant 20 may evaporate over time).

As another example, the device 10 may be configured such that the size, shape, surface texture and/or other physical dimension/aspect of the device 10 changes as the volume of the disinfectant 20 within the reservoir and dispenser portion 14 decreases to provide a tactile indication of the level thereof. For example, the dispensing surface portion 16 may include raised bumps or the like that flatten/shorten as the volume of the disinfectant 20 within the reservoir and dispenser portion 14 decreases.

As noted above, the reservoir and dispenser portion of the on-demand dispensing devices of the present disclosure may include one or more layers or portions. For example, as discussed above with respect to the reservoir and dispenser portion 14, the exemplary device 10 may include a dual/integral reservoir and dispenser layer or portion 14 that is configured as a reservoir that contains/holds the volume of the disinfectant 20 and a dispenser that forms the dispensing surface portion 16 and controls the amount of disinfectant 20 that flows/is present at the dispensing surface portion 16 and is transferred to a user when the user contacts/wipes the dispensing surface portion 16.

Figure 8:
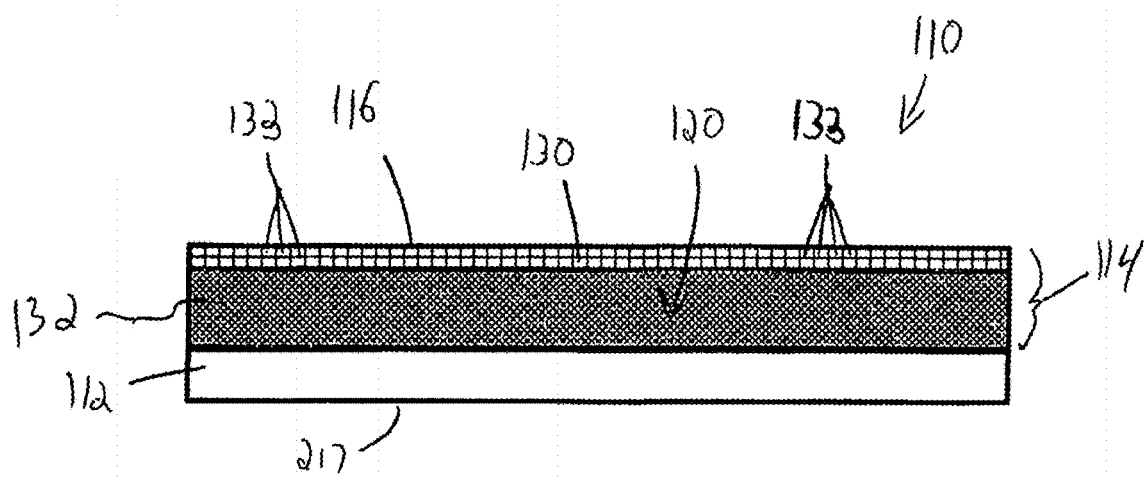
FIG. 8 illustrates a side cross-sectional view of an on-demand disinfectant dispensing device with a disinfectant release top layer according to one embodiment of the present disclosure.

An exemplary on-demand dispensing device 110 that includes separate and distinct reservoir and dispenser layers/portions is shown in FIG. 8. The device 110 of FIG. 8 is substantially similar to the device 10 described above with respect to FIG. 1-7, and therefore like reference numerals preceded with "1" are used to indicate like components, aspects, functions, processes or functions, and the description above directed to thereto equally applies, and is not repeated for brevity and clarity purposes.

As shown in FIG. 8, the device 110 includes a dispenser/dispensing portion or layer 130 overlying at least a portion of a reservoir layer or portion 132. The reservoir layer or portion 132 is configured to contain the volume of disinfectant 120 therein. For example, as discussed above, the disinfectant 120 may be absorbed within the reservoir layer or portion 132 and/or the reservoir layer or portion 132 may form a pocket or cavity that contains the disinfectant 120. The dispenser portion or layer 130 may be configured to control the release rate of the disinfectant 120 to/onto the dispensing surface portion 116, and thereby to/onto the user, when the user contacts or wipes the dispensing surface portion 116. For example, as shown in FIG. 8, the dispenser portion or layer 130 may comprise pores, apertures, channels, cracks, valves, openings, pathways or other flowpaths 132 for the disinfectant 120 to flow or translate from the reservoir layer or portion 132, through the dispenser portion or layer 130, and to the dispensing surface portion 116. The cross-sectional size, length/thickness, density, and/or total number, for example, of flowpaths 132 may be configured to allow/promote wicking/capillary action of the disinfectant 120 from the reservoir layer or portion 132 to/onto the dispensing surface portion 116 at a particular rate and, thereby, the release/dispense rate of the disinfectant 120 at the dispensing surface portion 116. The dispenser portion or layer 130 is thereby configured to allow/promote movement of the disinfectant 120 therethrough (e.g., via capillary action) at a controlled rate to the dispensing surface portion 116 to keep it loaded/activated with the disinfectant 120.

Figure 9:
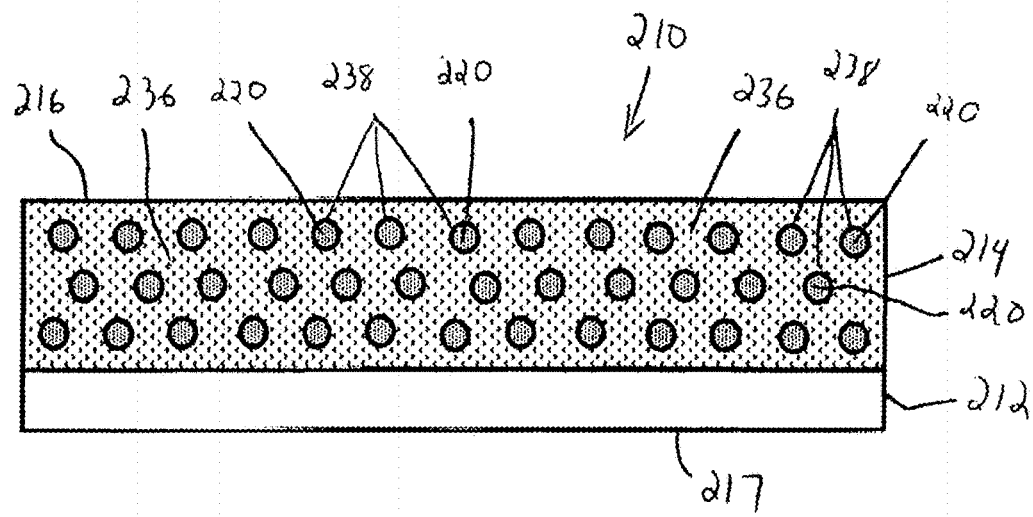
FIG. 9 illustrates a side cross-sectional view of an on-demand disinfectant dispensing device with embedded discrete disinfectant volumes according to one embodiment of the present disclosure.
Figure 10:
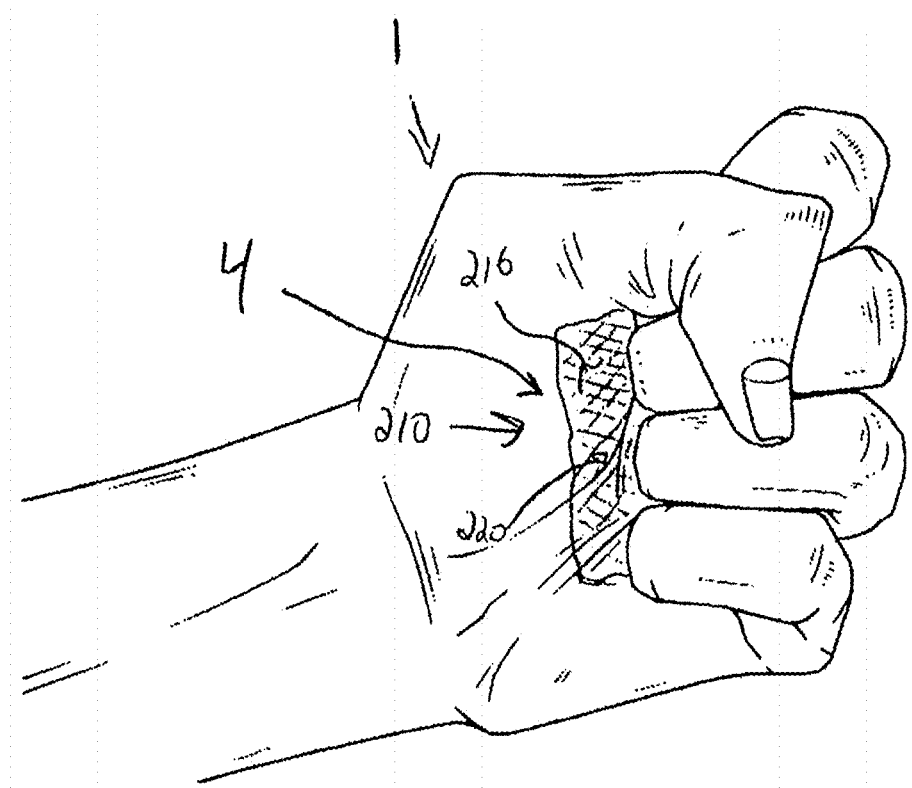
FIG. 10 illustrates a perspective view of the on-demand disinfectant dispensing device of FIG. 9 affixed to a user's hand and the user causing some of the embedded discrete disinfectant volumes to be dispensed according to one embodiment of the present disclosure.

Another exemplary embodiment of an on-demand dispensing device 210 according to the present disclosure is shown in FIGS. 9 and 10. The device 210 of FIGS. 9 and 10 is substantially similar to the device 10 of FIG. 1-7 and the device 110 of FIG. 8, and therefore like reference numerals preceded with "2" are used to indicate like components, aspects, functions, processes or functions, and the description above directed to thereto equally applies, and is not repeated for brevity and clarity purposes.

As shown in FIG. 9, the device 210 includes a reservoir and dispenser portion 214 that includes a plurality of discrete solid, gel and/or encapsulated portions 238 that each comprise the disinfectant 220. The discrete portions 238 are embedded or distributed within an inner portion 236 of the reservoir and dispenser portion 214 below the dispensing surface portion 216. The discrete portions 238 are configured to selectively release at least some of the disinfectant 220 to allow the disinfectant 220 to travel to the dispensing surface portion 216. For example, the discrete portions 238 may be configured to release disinfectant 220 upon the application of a particular pressure and/or temperature threshold. As shown in FIGS. 9 and 10, the device 210 may be attached to a user or surface 4, and the release mechanism may be applied to the device 210 to release the disinfectant 220 and, thereby, force or allow the disinfectant 220 to travel to the dispensing surface portion 216 (and thereby to a user therefrom).

As shown in FIG. 10, in one example the discrete portions 238 may comprise encapsulated portions 238 that rupture and release the disinfectant 220 upon the application of pressure thereto. In such an embodiments, the device 210 may be coupled to a user's inner hand/palm 4, for example, and the user can make a first to squeeze and "crush" the encapsulated portions 238 to release the disinfectant 220. However, it is noted the device 210 may be configured and/or used with a myriad of differing applications and/or release mechanisms to release the disinfectant 220 from the discrete portions 238.

Figure 11:
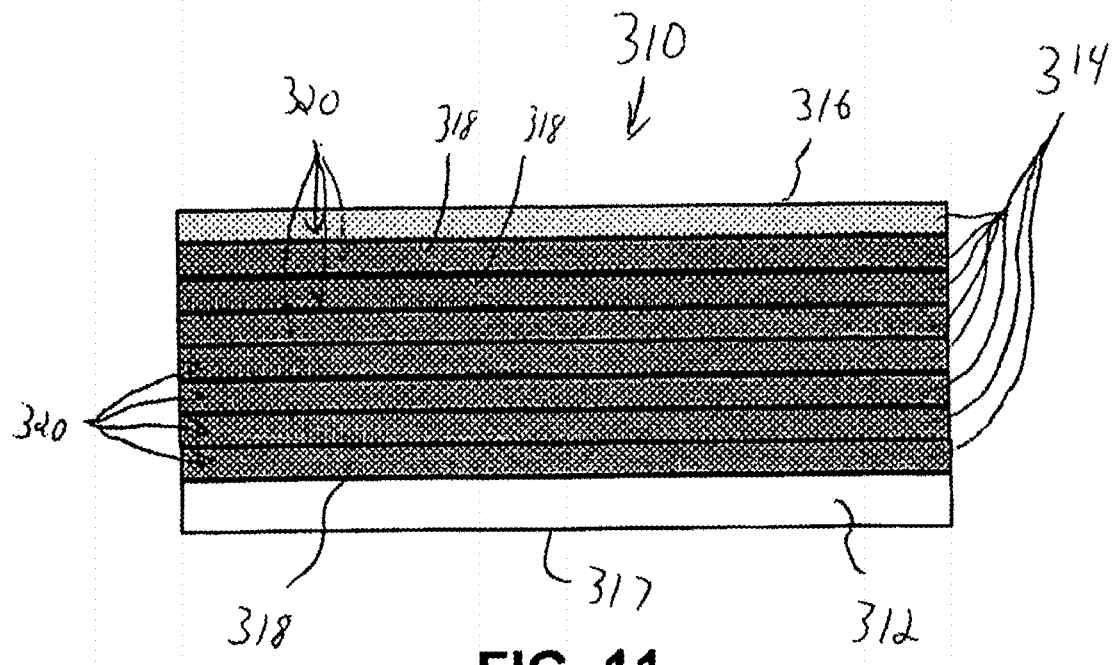
FIG. 11 illustrates a side cross-sectional view of an on-demand disinfectant dispensing device with a plurality of removable disinfectant reservoir and dispensing layers according to one embodiment of the present disclosure.

Another exemplary embodiment of an on-demand dispensing device 310 according to the present disclosure is shown in FIG. 11. The device 310 of FIG. 11 is substantially similar to the device 10 of FIG. 1-7, the device 110 of FIG. 8 and the device 210 of FIGS. 9 and 10, and therefore like reference numerals preceded with "3" are used to indicate like components, aspects, functions, processes or functions, and the description above directed to thereto equally applies, and is not repeated for brevity and clarity purposes.

As shown in FIG. 11, the device 310 includes a plurality of stacked or overlying reservoir and dispenser portions/layers 314. The reservoir and dispenser portions/layers 314 each include a back side surface 318 that overlies and is removably coupled/attached to the top side of an immediately underlying reservoir and dispenser portions/layers 314 (or the attachment layer or portion 312). As noted above, the reservoir and dispenser portions/layers 314 may be comprise of one or more portions, layer and/or materials.

The top side surface of the upper most reservoir and dispenser portions/layers 314 of the device 310 comprises or forms the dispensing surface portion 316, as shown in FIG. 11. The reservoir and dispenser portions/layers 314 may be removably coupled to each other via any adhesive or mechanical connection (such as a hook and loop fastener) that is configured such that an uppermost exposed reservoir and dispenser portions/layers 314 can be manually removed from the device 310 (e.g., manually peeled off the device 310) to expose the immediately underlying reservoir and dispenser portions/layers 314 when the volume of disinfectant 320 in the uppermost exposed reservoir and dispenser portions/layers 314 is depleted/dried.

Figure 12:
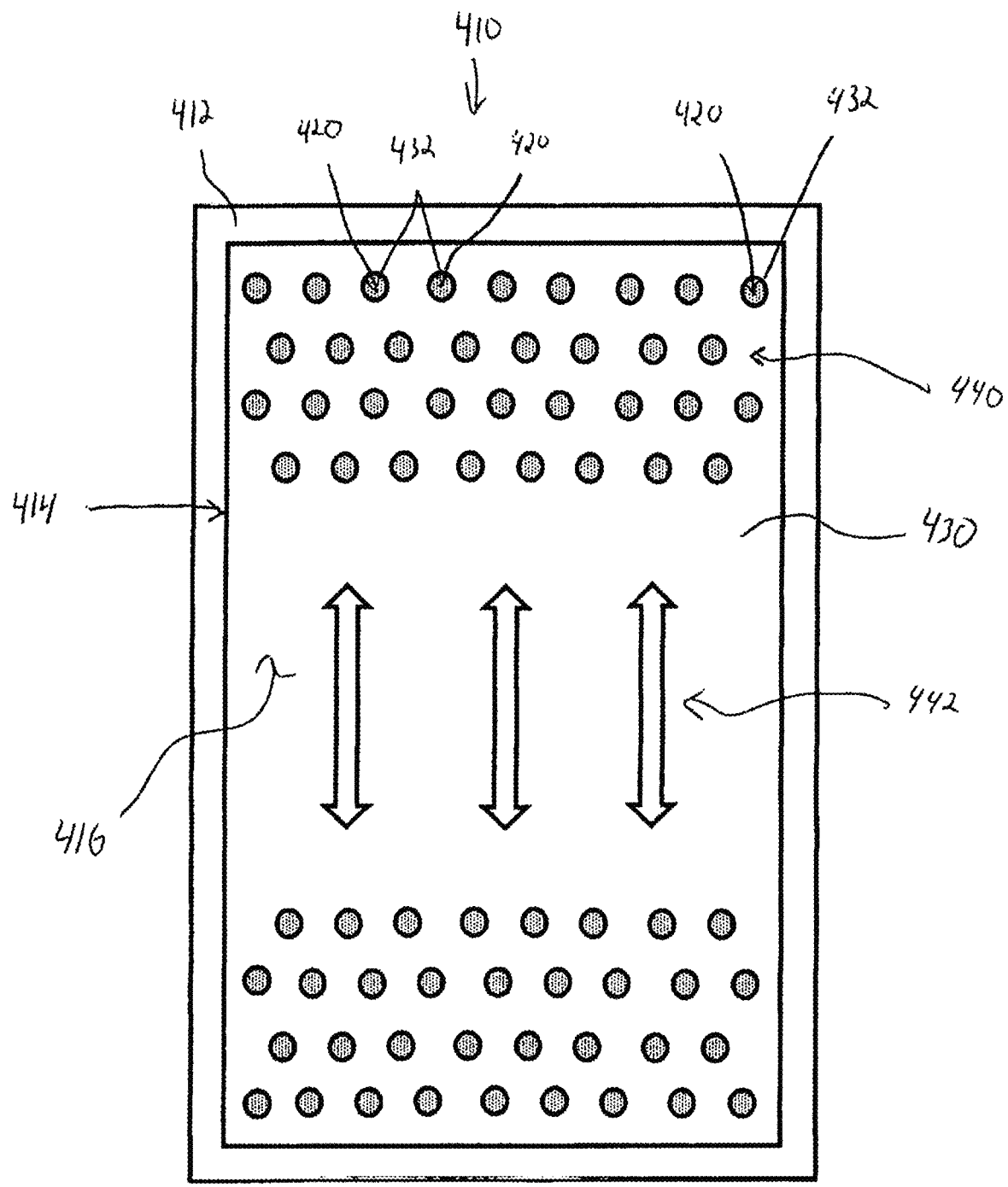
FIG. 12 illustrates a top view of an on-demand disinfectant dispensing device with a disinfectant reservoir area and at least one disinfectant dispensing area according to one embodiment of the present disclosure.

Another exemplary embodiment of an on-demand dispensing device 410 according to the present disclosure is shown in FIG. 12. The device 410 of FIG. 12 is substantially similar to the device 10 of FIG. 1-7, the device 110 of FIG. 8, the device 210 of FIGS. 9 and 10 and the device 310 of FIG. 11, and therefore like reference numerals preceded with "4" are used to indicate like components, aspects, functions, processes or functions, and the description above directed to thereto equally applies, and is not repeated for brevity and clarity purposes.

As shown in FIG. 12, the on-demand disinfectant dispensing device 410 comprises at least one reservoir area 442 and at least one dispensing area 440. The reservoir area 442 comprises an area of the reservoir and dispenser portion/layer 414 that comprises the volume of the disinfectant 420, and the dispensing area 440 comprises an area of the reservoir and dispenser portion/layer 414 that is configured to control the release of the volume of the disinfectant 420 and comprises the dispensing surface portion 416 where the disinfectant 420 is ultimately released. For example, as shown in FIG. 12, the dispensing area 440 may comprise a plurality of holes, pores or other passages 432 that are spaced from, but in communication with, the reservoir area 442.

The device 410 is configured that the application of pressure on the reservoir area 442 forces disinfectant 420 from the reservoir area 442 and to and through the dispensing area 440 to the dispensing surface portion 416. For example, as shown in FIG. 12, the device 410 may be configured such that pressure applied on the reservoir area 442 along one or more particular directions may act to force the disinfectant 420 through the dispenser portion/layer 414 and to and through the apertures/passageways 432 of the dispensing area 440. In this way, the device 410 may be configured to release/dispense the disinfectant 420 based on a the application of pressure (e.g., hand or finger swipe) on and/or along the dispensing area 440 to dispense the disinfectant 420 through the dispenser portion/layer 414 and to and through the apertures/passageways 432 of the dispensing area 440. The trajectory/directional application of pressure/force on the reservoir area 442 toward the dispensing area 440 may be more effective in dispensing the disinfectant 420 or required to dispense the disinfectant 420.

Figure 13:
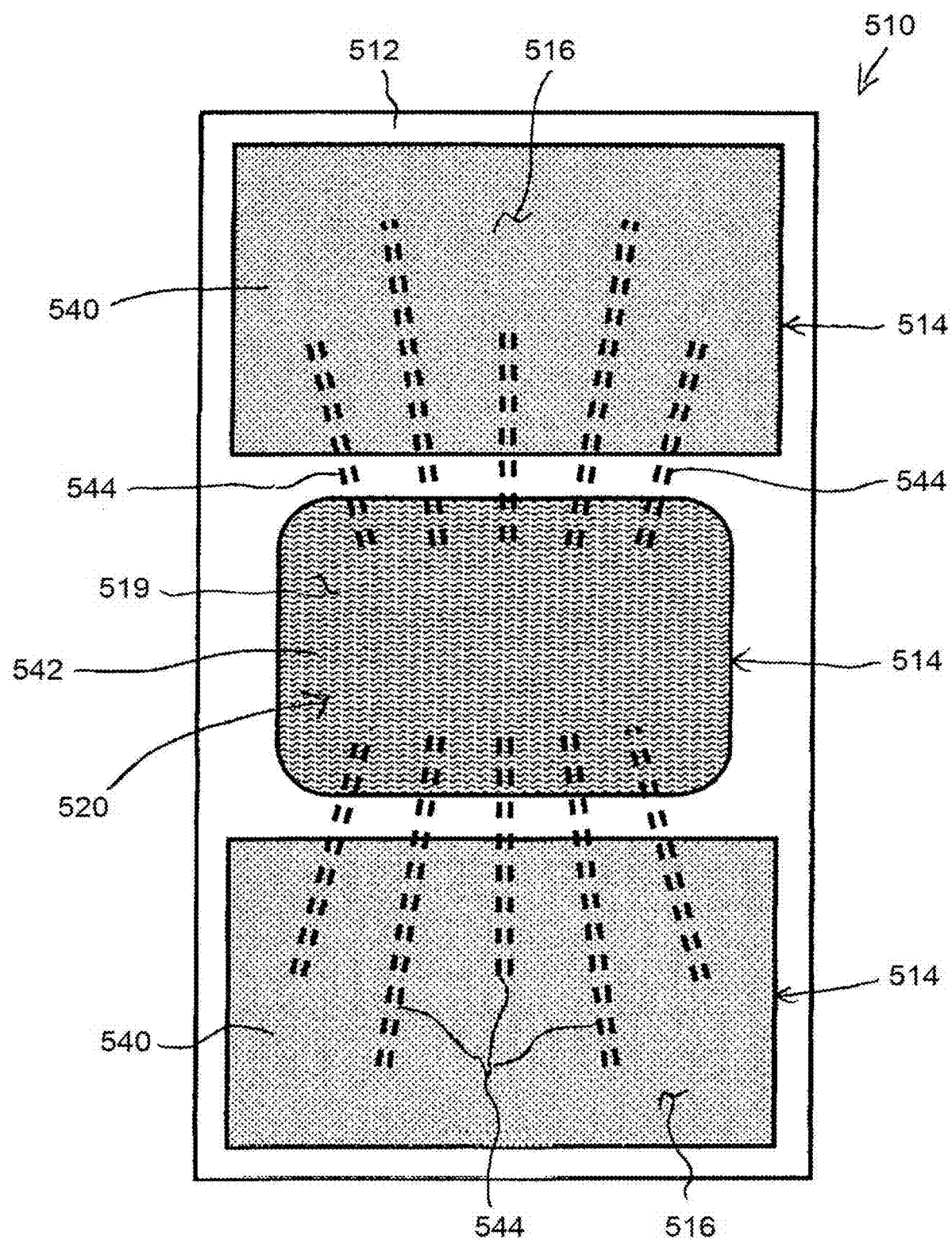
FIG. 13 illustrates a top view of an on-demand disinfectant dispensing device with a disinfectant reservoir and pump area, at least one disinfectant dispensing area and at least one defined flowpath for the flow of disinfectant from the disinfectant reservoir and pump area to the at least one disinfectant dispensing area according to one embodiment of the present disclosure.

Another exemplary embodiment of an on-demand dispensing device 510 according to the present disclosure is shown in FIGS. 13-15. The device 510 of FIGS. 13-15 is substantially similar to the device 10 of FIG. 1-7, the device 110 of FIG. 8, the device 210 of FIGS. 9 and 10, the device 310 of FIG. 11 and the device 410 of FIG. 12, and therefore like reference numerals preceded with "5" are used to indicate like components, aspects, functions, processes or functions, and the description above directed to thereto equally applies, and is not repeated for brevity and clarity purposes.

As shown in FIGS. 13-15, the on-demand disinfectant dispensing device 510 comprises at least one reservoir and pump area 542, at least one dispensing area 540 and at least one defined flowpath/channel 544 for the flow of the disinfectant 520 from the reservoir and pump area 542 to the dispensing area 542. The reservoir and pump area 542 may comprise a volume of the disinfectant 520 contained within a defined flexible internal cavity, opening or pouch that it is fluid communication with at least one defined flowpath/channel 544, as shown in FIGS. 13-15. The reservoir and pump area 542 may form a raised area that is visually and/or tactically identifiable by a user. The flexible internal cavity of the reservoir and pump area 542 may be substantially sealed but for the at least one defined flowpath/channel 544 such that compression of the reservoir and pump area 542 forces the disinfectant 520 out from the cavity and into and through the at least one defined flowpath/channel 544. As shown in FIG. 14, the area surrounding the reservoir and pump area 542, or at least positioned between the reservoir and pump area 542 and the reservoir and pump area 542 may be sealed off or blocked by a sealing portion 546. As shown in FIG. 15, the at least one defined flowpath/channel 544 may extend through the sealing portion 546 and is configured to contain and direct a flow of the disinfectant 520 from the of the flexible internal cavity of the reservoir and pump area 542 to the dispensing area 542.

The dispensing area 540 may be configured to hold/contain a volume of the disinfectant 520 delivered from the reservoir and pump area 542 via the at least one flowpath/channel 544 and, ultimately, control the release/dispensing of the disinfectant 520 at the dispensing surface portion 516, as discussed above. The reservoir and pump area 542 may thereby serve as an on-demand supply of the disinfectant 520 for the dispensing area 540 as the disinfectant 520 therein/thereof becomes depleted. In use, a user can apply pressure to the outside or top side 519 of the reservoir and pump area 542 to compress/pressurize the internal cavity thereof, and thereby force a portion of the volume of the disinfectant 520 from the internal cavity, into and through the at least one defined flowpath/channel 544, and to the dispensing area 542. In some embodiments, the dispensing area 542 is configured to control the rate of release of the disinfectant 520 from the dispensing surface portion 516. In some embodiments, the application of pressure on the reservoir and pump area 542 may force the disinfectant 520 through the dispensing area 542 and release disinfectant 520 from the dispensing surface portion 516.

Figure 16:
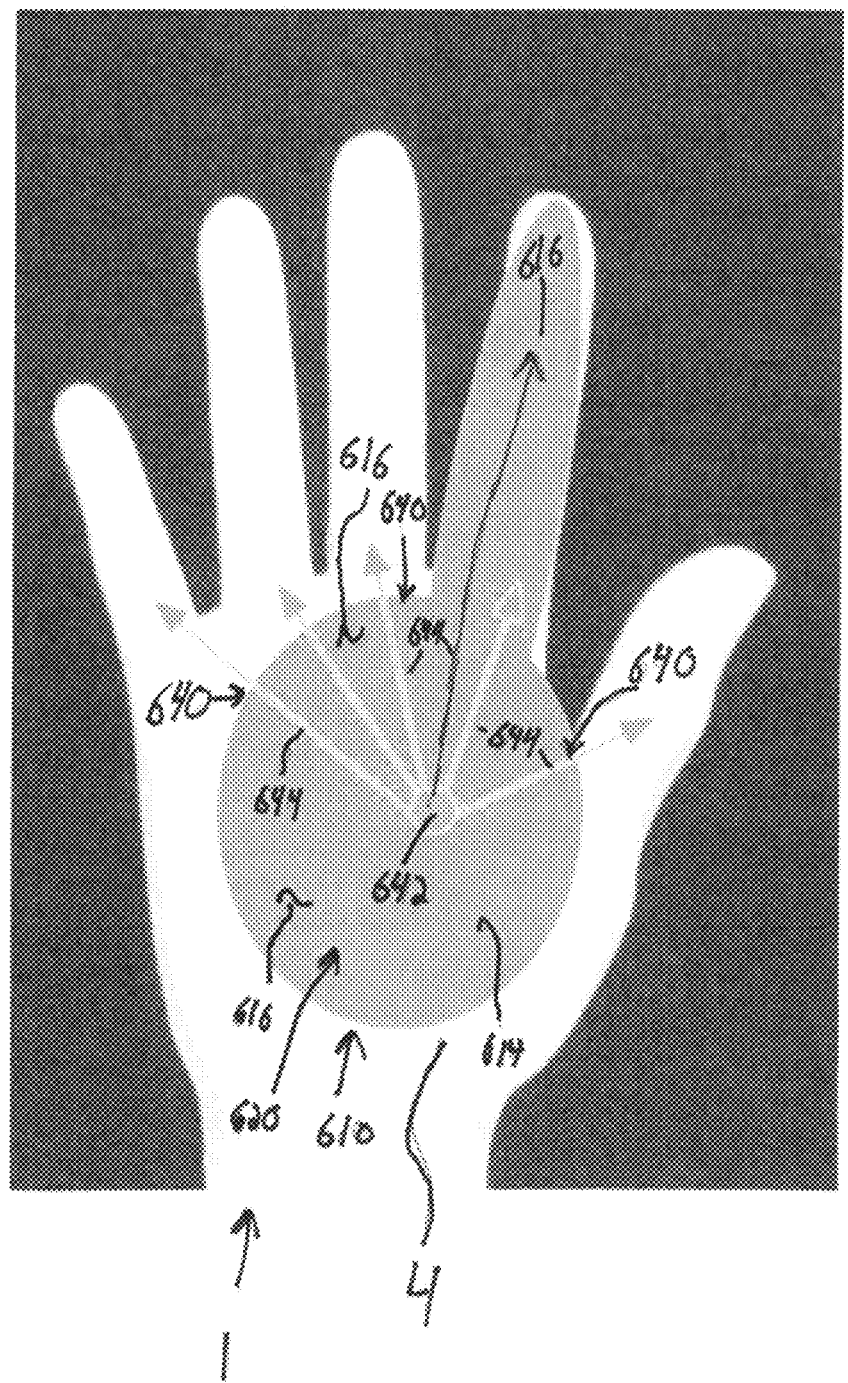
FIG. 16 illustrates a top view of an on-demand disinfectant dispensing device configured to be applied to a user's hand according to one embodiment of the present disclosure.

Another exemplary embodiment of an on-demand dispensing device 610 according to the present disclosure is shown in FIG. 16. The device 510 of FIG. 16 is substantially similar to the device 10 of FIG. 1-7, the device 110 of FIG. 8, the device 210 of FIGS. 9 and 10, the device 310 of FIG. 11, the device 410 of FIG. 12 and the device 510 of FIGS. 13-15, and therefore like reference numerals preceded with "6" are used to indicate like components, aspects, functions, processes or functions, and the description above directed to thereto equally applies, and is not repeated for brevity and clarity purposes.

As shown in FIG. 16, the on-demand disinfectant dispensing device 610 comprises at least one reservoir and pump area 642, at least one dispensing area 640 and at least one defined flowpath/channel 644 for the flow of the disinfectant 620 from the reservoir and pump area 642 to the dispensing area 642 and, ultimately, out of the dispensing surface portion 616. As shown in FIG. 16, the dispensing device 610 differs from the dispensing device 610 as it is configured for an active skin portion 4 of a user 1. The pump area 642 is configured such that closing of the user's 1 hand/palm compresses the internal cavity thereof to compress/pressurize the cavity and thereby force the disinfectant 620 through a plurality of channels 644 to the dispensing area 640. In some embodiments, the dispensing area 640 may comprise a plurality of spaced release points or areas.

The device 610 may be configured such that the disinfectant 620 is dispensed due to movement of the user 1, such as but not limited to a haptic gesture of the user 1. For example, as shown in FIG. 16, the device 610 may be configured such that the reservoir and pump area 642 is positioned in a palm area of the device 610 (i.e., that is positioned on the user's 1 palm when the device 610 is attached to the user's inner hand 4), and include a plurality of channels 644 extending to a plurality of dispensing areas 640 (such as near the user's 1 finger(s)). As shown in FIG. 16, in some embodiments the device 610 may extend over the user's 1 palm and at least one finger when attached to the user's 1 inner hand 4. In this way, a user 1 can selectively apply the disinfectant 20 to their palm and/or at least one finger simply by compressing their hand or making a first (i.e., compressing the internal cavity of the reservoir and pump area 642) (or otherwise compressing the reservoir and pump area 642). In one exemplary embodiment, the device 610 may also extend to at least a portion of the back of the user/s 2 hand 4, such as extending over/around the tip of at least one finger of the user's 1 hand 4.

Figure 17:
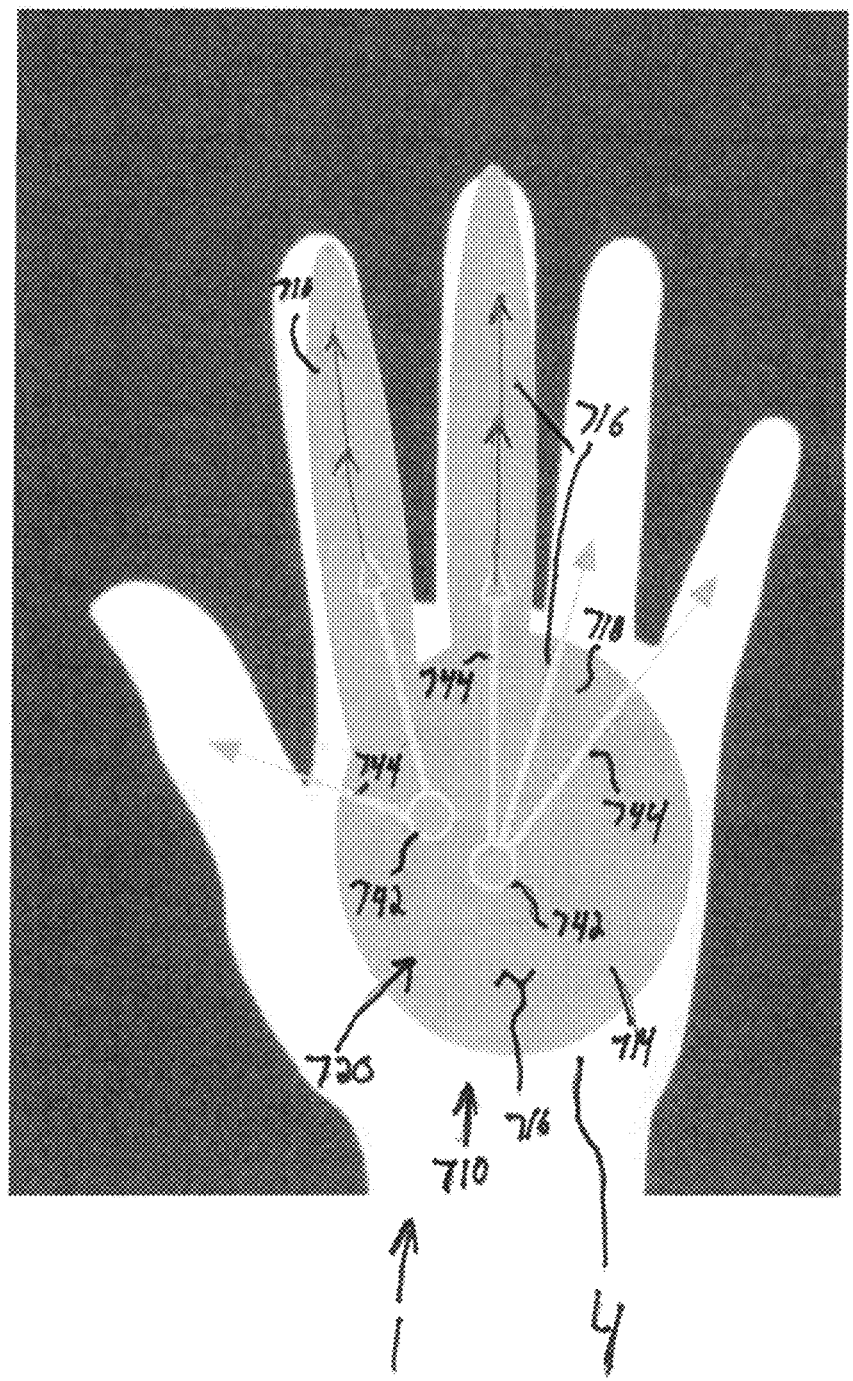
FIG. 17 illustrates a top view of another on-demand disinfectant dispensing device configured to be applied to a user's hand according to one embodiment of the present disclosure.

Another exemplary embodiment of an on-demand dispensing device 710 according to the present disclosure is shown in FIG. 17. The device 610 of FIGS. 13-15 is substantially similar to the device 10 of FIG. 1-7, the device 110 of FIG. 8, the device 210 of FIGS. 9 and 10, the device 310 of FIG. 11, the device 410 of FIG. 12, the device 510 of FIGS. 13-15 and the device 610 of FIG. 16, and therefore like reference numerals preceded with "7" are used to indicate like components, aspects, functions, processes or functions, and the description above directed to thereto equally applies, and is not repeated for brevity and clarity purposes.

The dispensing device 710 is substantially identical to the dispensing device 610 but for the inclusion of a plurality of reservoir and pump areas 742 (or a plurality of internal cavities of a reservoir and pump area 742) and a plurality of portions that extend over a plurality of a user's 1 fingers when the device 710 is coupled to the user's inner hand 4. As shown in FIG. 17, the device 710 is may thereby be configured to suit any wearer (e.g., any body portion or any surface of any inanimate object) and any movement/rearrangement of the device 710 to compress the reservoir and pump areas 742 and cause the disinfectant 720 to be selectively dispensed.

Figure 18:
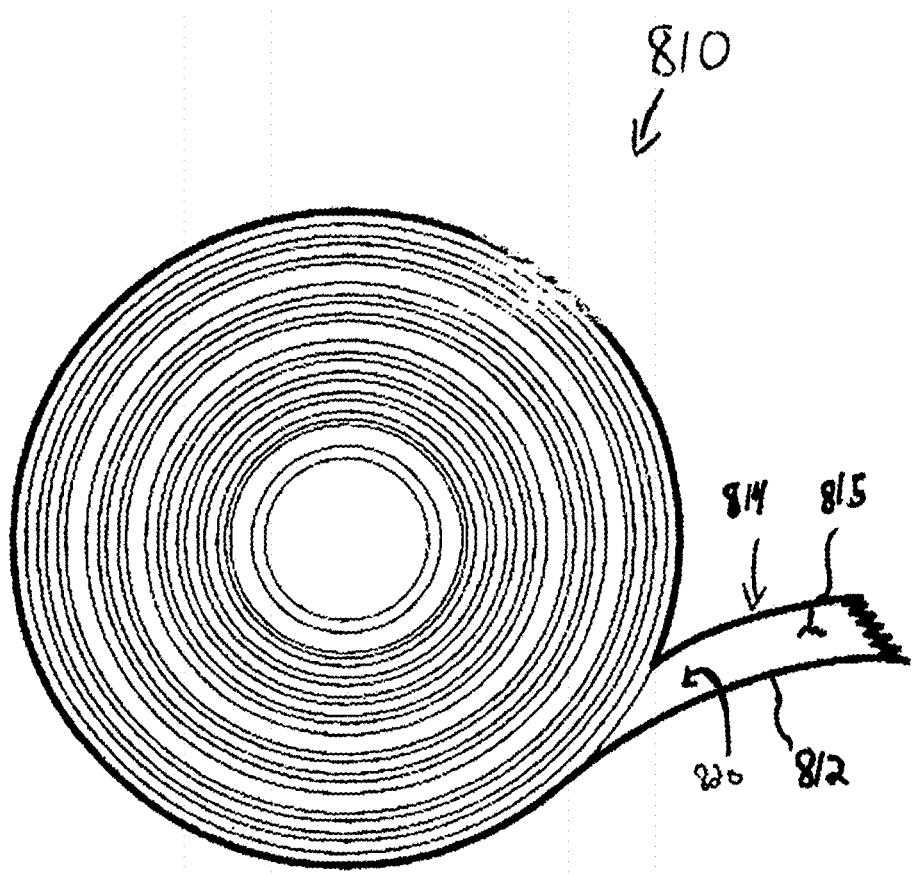
FIG. 18 illustrates a perspective view of an elongated on-demand delivery device configured to in a roll form according to one embodiment of the present disclosure.

Another exemplary embodiment of an on-demand dispensing device 810 according to the present disclosure is shown in FIG. 18. The device 810 of FIG. 18 is substantially similar to the device 10 of FIG. 1-7, the device 110 of FIG. 8, the device 210 of FIGS. 9 and 10, the device 310 of FIG. 11, the device 410 of FIG. 12, the device 510 of FIGS. 13-15, the device 610 of FIG. 16 and the device 710 of FIG. 17, and therefore like reference numerals preceded with "8" are used to indicate like components, aspects, functions, processes or functions, and the description above directed to thereto equally applies, and is not repeated for brevity and clarity purposes.

As shown in FIG. 18, the reservoir and dispenser portion/layer 814 of the on-demand disinfectant dispensing device 810 comprises at least one (manually) flexible and porous polymer member comprising internal voids in communication with the outer dispenser surface portion 816 thereof. The member may be comprised of any flexible porous polymer. For example, the polymer member may be formed of silicone, polyurethane, hydrogel or a combination thereof. The member may form an elongate and/or sheet-like shape, and may be arranged into a roll form (which may facilitate the application of the device 810). The member may be any shape and/or length to suit a particular surface.

Also shown in FIG. 18, the polymer member of the device 810 includes a disinfectant agent 820 contained within the internal voids of the member. The member is configured such that the disinfectant 820 is naturally drawn to the outer dispenser surface portion 816 from within the internal voids, such as due to capillary action (and/or evaporation of the disinfectant 820 at the dispenser surface portion 816).

In some embodiments, the device 810 may include an adhesive or attachment mechanism coupled to a backside of the polymer member configured to attach/affix the device 810 to a surface, as discussed above (and potentially a protective film thereover). In some other embodiments, the device 810 may be void of an adhesive or attachment mechanism coupled to a backside of the polymer member (which may be applied/coupled thereto just prior to being coupled to a surface, for example).

In some embodiments, the member may include perforations, cuts, gaps or the like (not shown) configured to allow a portion(s) of the member to be manually separated. In some embodiments, the device 810 may include a dispenser device that holds the member and allows the member to be dispensed therefrom. In some such embodiments, the dispenser device may include a cutting implement configured to selectively cut the member.

Figure 19:
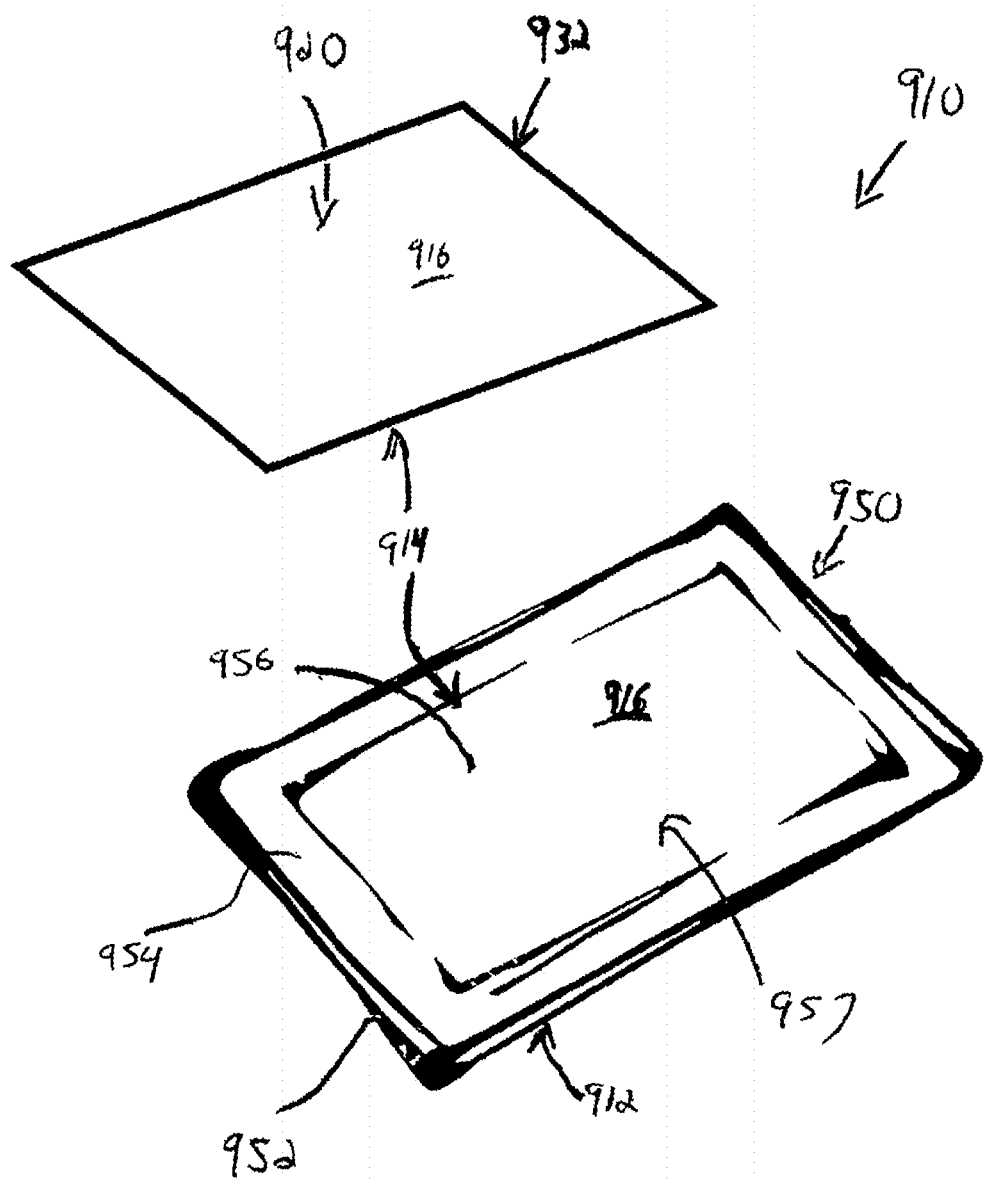
FIG. 19 illustrates an elevational perspective view of an on-demand delivery device configured in a pocket form according to one embodiment of the present disclosure.

Another exemplary embodiment of an on-demand dispensing device 910 according to the present disclosure is shown in FIG. 19. The device 910 of FIG. 19 is substantially similar to the device 10 of FIG. 1-7, the device 110 of FIG. 8, the device 210 of FIGS. 9 and 10, the device 310 of FIG. 11, the device 410 of FIG. 12, the device 510 of FIGS. 13-15, the device 610 of FIG. 16, the device 710 of FIG. 17 and the device 810 of FIG. 18, and therefore like reference numerals preceded with "9" are used to indicate like components, aspects, functions, processes or functions, and the description above directed to thereto equally applies, and is not repeated for brevity and clarity purposes.

As shown in FIG. 19, the device 910 includes a pocket portion 950 with an internal cavity 957 and the reservoir portion 932 that contains a disinfectant 920 therein configured to couple (e.g., removably) within the internal cavity 957. In some embodiments, the pocket portion 950 may be formed of or comprise a backing layer or portion 952 that is configured to prevent the disinfectant 920 from passing therethrough. For example, the backing layer or portion 952 may be waterproof or water resistant, as shown in FIG. 19. As also shown in FIG. 19, the pocket portion 950 may include a front portion 954. The front portion 954 and the backing portion 952 may cooperate to form the internal cavity 957 therebetween, as shown in FIG. 19.

In some embodiments, the front portion 954 may include or define an opening or window such that an outer surface of the reservoir portion 932 is exposed when the reservoir portion 932 is positioned within the pocket portion 950. In such an embodiments, the reservoir portion 932 may comprise the reservoir portion and the dispensing portion 914, as discussed above. In this way, the outer surface of the reservoir portion 932 may define the disinfectant dispensing surface 916.

In some other embodiments (not shown), the front portion 954 may extend over at least a substantial portion of the outer surface of the reservoir portion 932 when the reservoir portion 932 is positioned within the pocket portion 950. In such an embodiment, the reservoir portion 932 may comprise the reservoir portion of the device 910 as discussed above, and the front portion 954 may comprise (and thus be configured as) the dispensing portion 914 of the device 910, as discussed above. In this way, the outer surface of the front portion 954 may define the disinfectant dispensing surface 916.

The backside of the pocket portion 950 may include the attachment layer or portion 912 of the device 910 and be configured to couple (removably or fixedly) to any myriad of surfaces, as discussed above.

Figure 20:
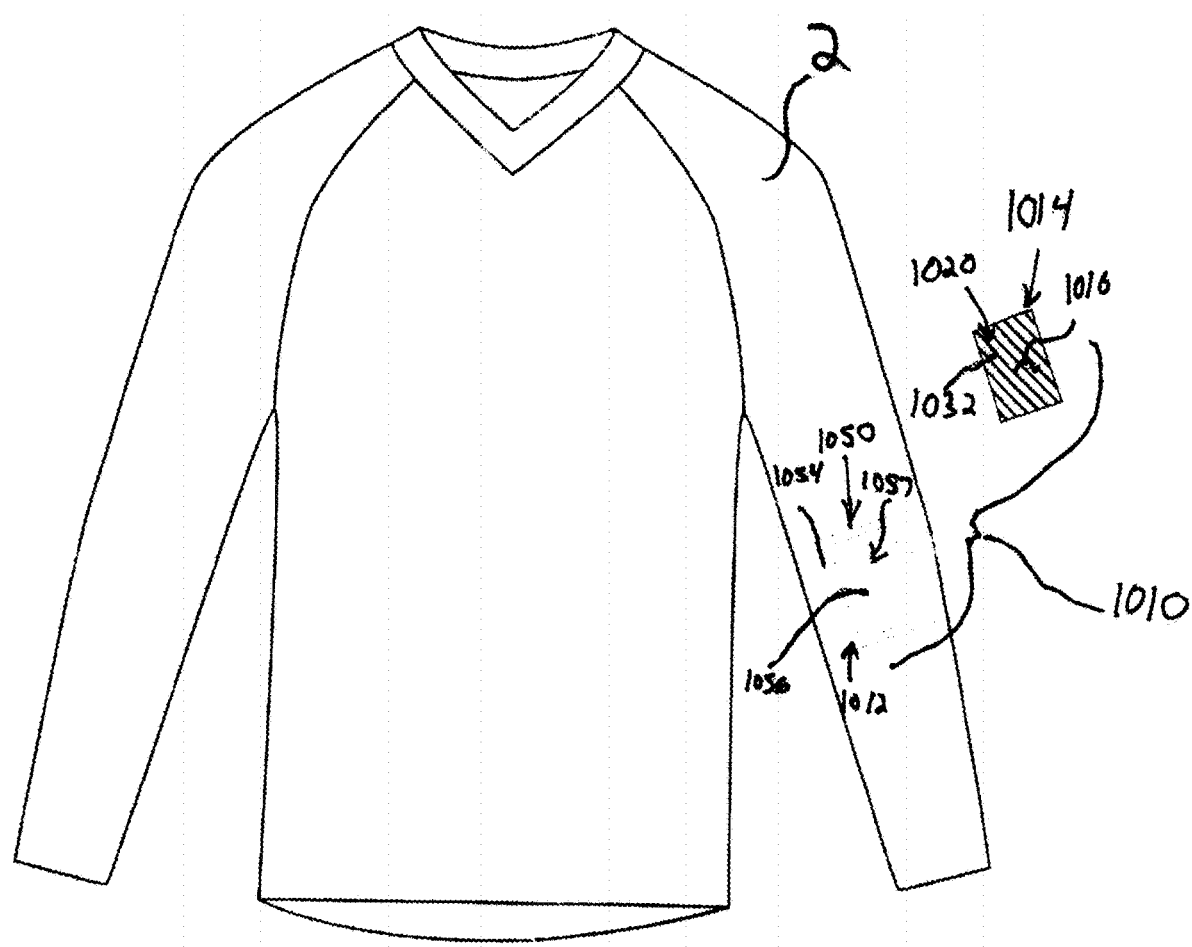
FIG. 20 illustrates a pocket-form on-demand delivery device incorporated into a piece of clothing according to one embodiment of the present disclosure.
Figure 21:
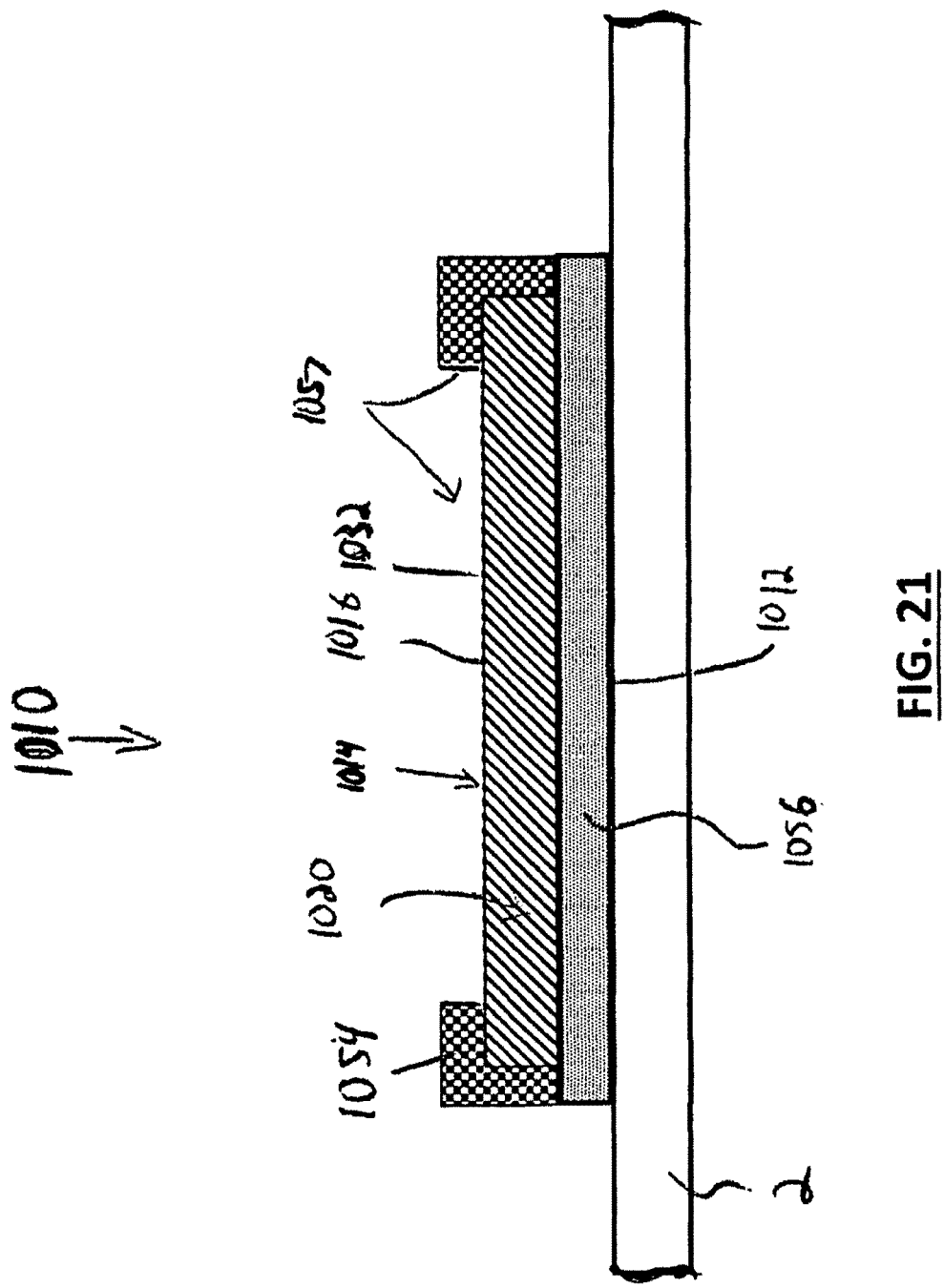
FIG. 21 illustrates a cross-sectional view of the on-demand delivery device of FIG. 20 according to one embodiment of the present disclosure.

Another exemplary embodiment of an on-demand dispensing device 1010 according to the present disclosure is shown in FIGS. 20 and 21. The device 1010 of FIGS. 20 and 21 is substantially similar to the device 10 of FIG. 1-7, the device 110 of FIG. 8, the device 210 of FIGS. 9 and 10, the device 310 of FIG. 11, the device 410 of FIG. 12, the device 510 of FIGS. 13-15, the device 610 of FIG. 16, the device 710 of FIG. 17, the device 810 of FIG. 18 and the device 910 of FIG. 19, and therefore like reference numerals preceded with "10" are used to indicate like components, aspects, functions, processes or functions, and the description above directed to thereto equally applies, and is not repeated for brevity and clarity purposes.

As shown in FIGS. 20 and 21, the device 1010 is substantially similar to the device 910 discussed above with respect to FIG. 19. Device 1010 differs from the device 910 in that the pocket portion 1050 is integrated into another object 2, such as a clothing item or other item that would be worn or carried by a user. As shown in FIGS. 20 and 21, the front portion 1054 of the pocket portion 1050 defines a window or opening 1056 such that the outer surface of the reservoir portion 1032 is exposed when the reservoir portion 1032 is positioned within the internal cavity 1057 of the pocket portion 950. The reservoir portion 1032 thereby comprises the reservoir portion of the device 1010, and the front portion 1054 comprises (and is thus configured as) the dispensing portion 1014 of the device 101. The outer surface of the front portion 1054 also thereby defines the disinfectant dispensing surface 1016, as shown in FIGS. 20 and 21.

Figure 22:
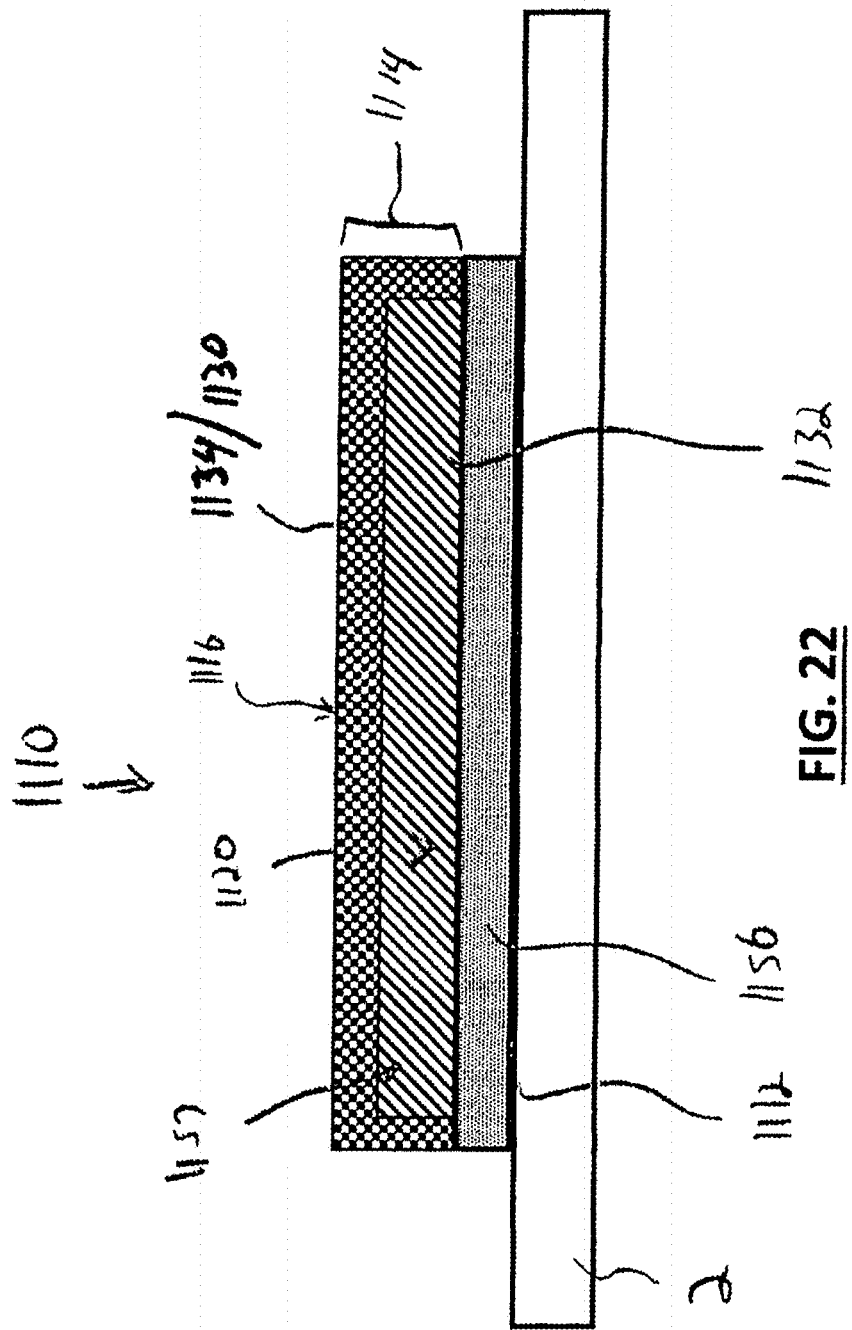
FIG. 22 illustrates a cross-sectional view of another pocket-form on-demand delivery device according to one embodiment of the present disclosure.

Another exemplary embodiment of an on-demand dispensing device 1110 according to the present disclosure is shown in FIG. 22. The device 1110 of FIG. 22 is substantially similar to the device 10 of FIG. 1-7, the device 110 of FIG. 8, the device 210 of FIGS. 9 and 10, the device 310 of FIG. 11, the device 410 of FIG. 12, the device 510 of FIGS. 13-15, the device 610 of FIG. 16, the device 710 of FIG. 17, the device 810 of FIG. 18, the device 910 of FIG. 19 and the device 1010 of FIGS. 20 and 21, and therefore like reference numerals preceded with "11" are used to indicate like components, aspects, functions, processes or functions, and the description above directed to thereto equally applies, and is not repeated for brevity and clarity purposes.

As shown in FIG. 22, the device 1110 is substantially similar to the device 1010 discussed above with respect to FIGS. 20 and 21. Device 1110 differs from the device 1010 in that the front portion 1154 extends over at least a substantial portion of the outer surface of the reservoir portion 1132 when the reservoir portion 1132 is positioned within the internal cavity 1157 of the pocket portion 1150. The reservoir portion 1132 comprises the reservoir portion of the device 1110 as discussed above, and the front portion 1154 comprises (and thus is configured as) the dispensing portion 1114 of the device 1110, as discussed above. In this way, the outer surface of the front portion 1154 defines the disinfectant dispensing surface 1116.

In some exemplary embodiments, the present disclosure provides for on-demand agent (e.g., disinfectant) dispensing devices and kits, and related methods utilizing such device and kits, which can be removably affixed to an object (such as a user or a surface of an inanimate object) that provide easy, available access to a supply of the agent over an extended period of time. The devices are configured as a patch that is configured to efficiently provide the agent on an on-demand basis via a step of apply pressure to or compressing the patch in its thickness direction (and potential along a length of the patch, such as a wiping or swiping motion/pathway).

The on-demand agent dispensing patches provide a simple, cost effective way to dispense the agent. The patches are self-contained, and can be used with any agent that can be applied to a "dry" patch, while providing a no spill dispensing solution that does not necessitate pouring or spraying the agent prior to each application or dispensing. In some embodiments, the patch may be configured to be removably affixed to a user, such as to the user's skin or the user's clothing (or any other inanimate object carried or worn by the user). In such a configuration, the on-demand agent dispensing patch provides a wearable device for dispensing the agent. The on-demand agent dispensing wearable devices may be configured to be removably affixed to a contact of a user or object that would benefit from having the agent thereon or thereat, such as on the inside of a user's hand (e.g., on the palm and/or fingers) with the agent being a disinfectant. In this way, the active on-demand agent dispensing wearable patch can be applied over an "active" portion of the user (e.g., a user's elbow, palm, finger, etc.) or object and replace the portion with the outer surface of the patch.

In some embodiments, the on-demand agent dispensing patch may be configured to be wearable such that it is removably affixed to a passive portion of the user's skin (or an object worn/carried by the user) (or on an inanimate object remote from the user) that is spaced from the point/portion of contact of the user, to allow for selective application of the agent via contact of the outer face of the patch via a user pressing on/compressing the patch. For example, a passive on-demand agent dispensing wearable patch may be removably affixed to the back of a user's hand or on a forearm, or on their clothing, and the user may swipe their finger(s)/hand on/over the exposed outer face of the patch to dispense the agent thereon. In such a passive dispensing embodiment, the on-demand agent dispensing wearable patch provides quick and discrete on-demand access to the agent where swiping/contacting the device causes the agent to be dispensed on/to the person's point/portion of contact (e.g., their hand(s) or other skin surface).

The on-demand agent dispensing patch disclosed herein can thereby be applied to an active or passive surface portion of a user (or an object) to provide the agent thereon/thereat. In this way, when the agent is a disinfectant, the on-demand dispensing patch can provide an amount/level of disinfectant to a user.

FIGS. 23-33 illustrate another exemplary agent dispensing patch device 1210 according to the present disclosure. The device 1210 is substantially similar to the device 10 of FIG. 1-7, the device 110 of FIG. 8, the device 210 of FIGS. 9 and 10, the device 310 of FIG. 11, the device 410 of FIG. 12, the device 510 of FIGS. 13-15, the device 610 of FIG. 16, the device 710 of FIG. 17, the device 810 of FIG. 18, the device 910 of FIG. 19, the device 1010 of FIGS. 20 and 21, and the device 1110 of FIG. 22, and therefore like reference numerals preceded with "12" are used to indicate like components, aspects, functions, processes or functions, and the description above directed to thereto equally applies, and is not repeated for brevity and clarity purposes.

As noted above, the agent may be any liquid or gelatinous agent that would benefit from, or lend itself to, being available on demand over a period of time, and being dispensed in doses or relatively small volumes. For example, the patch device 1210 may be used with a liquid or gelatinous sanitizing/disinfecting agent (i.e., a sanitizer or disinfectant) so that the sanitizing/disinfecting agent is available on demand to a user or an extended period of time, and a volume there can be dispensed for use easily and quickly from the patch device 1210 without having to open or otherwise access a container or package of the sanitizing/disinfecting agent.

Figure 23:
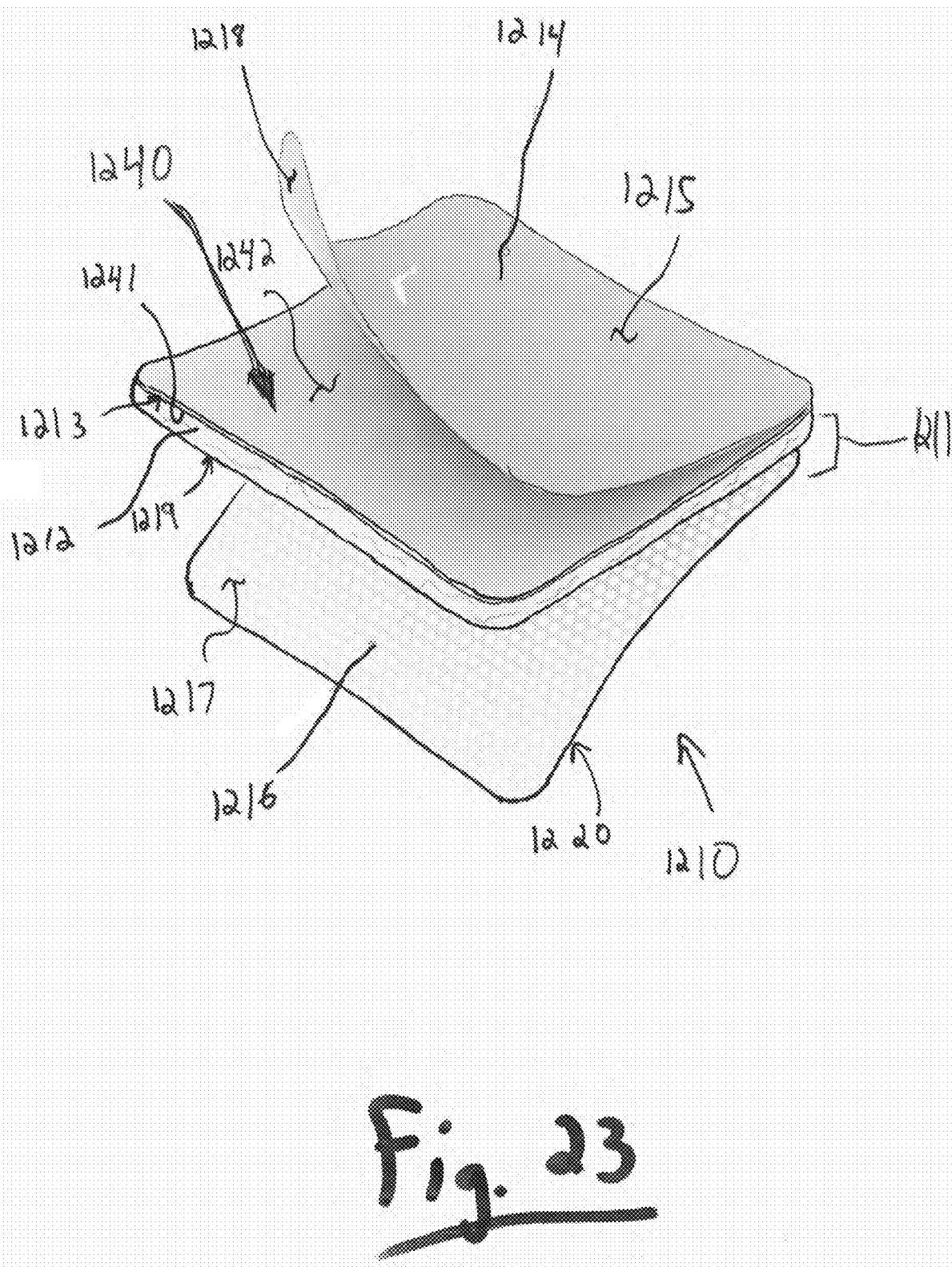
FIG. 23 illustrates a top perspective partial-exploded view of an on-demand agent dispensing patch according to one embodiment of the present disclosure.
Figure 24:
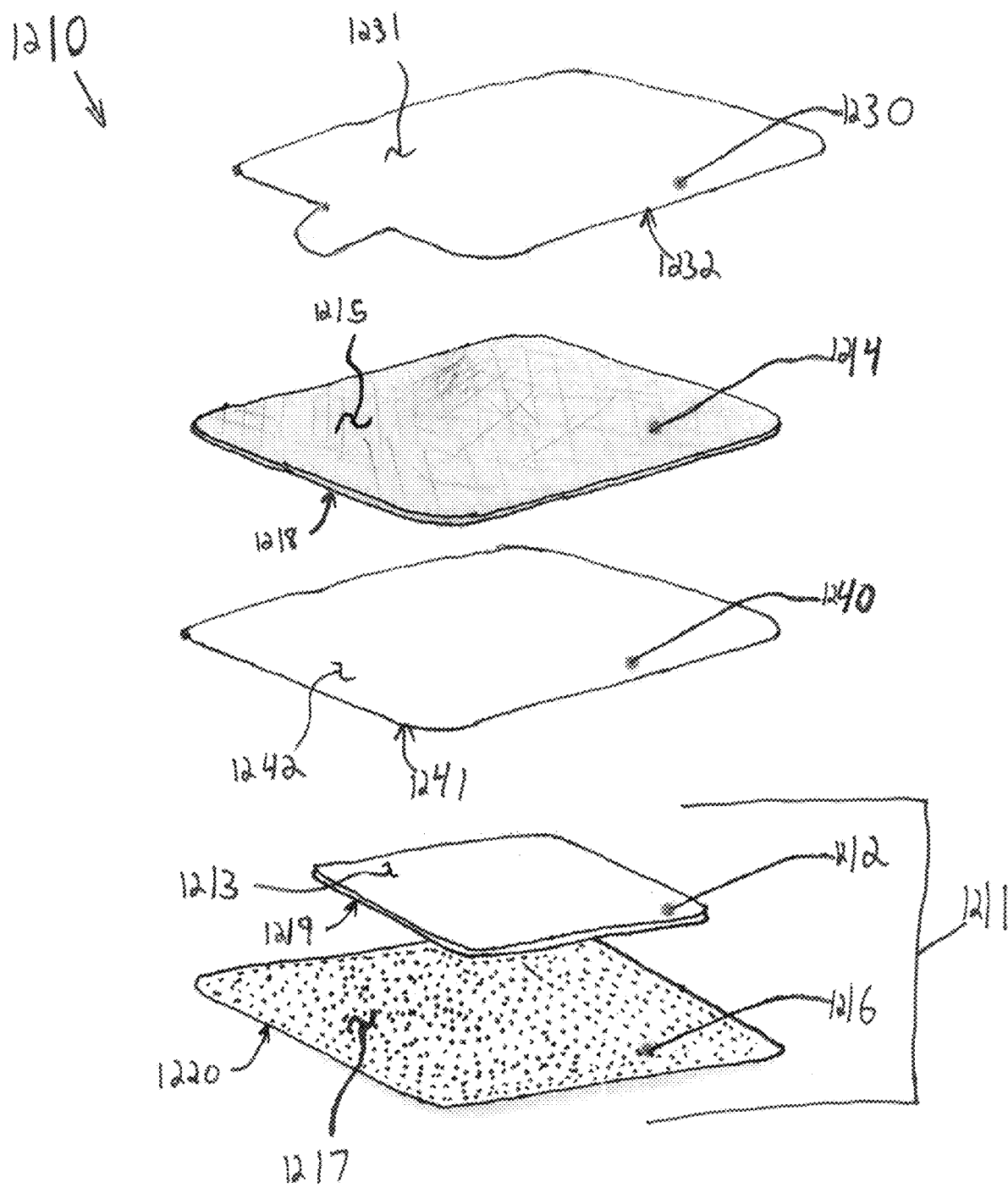
FIG. 24 illustrates a top perspective exploded view of an on-demand agent dispensing patch according to one embodiment of the present disclosure.
Figure 25:
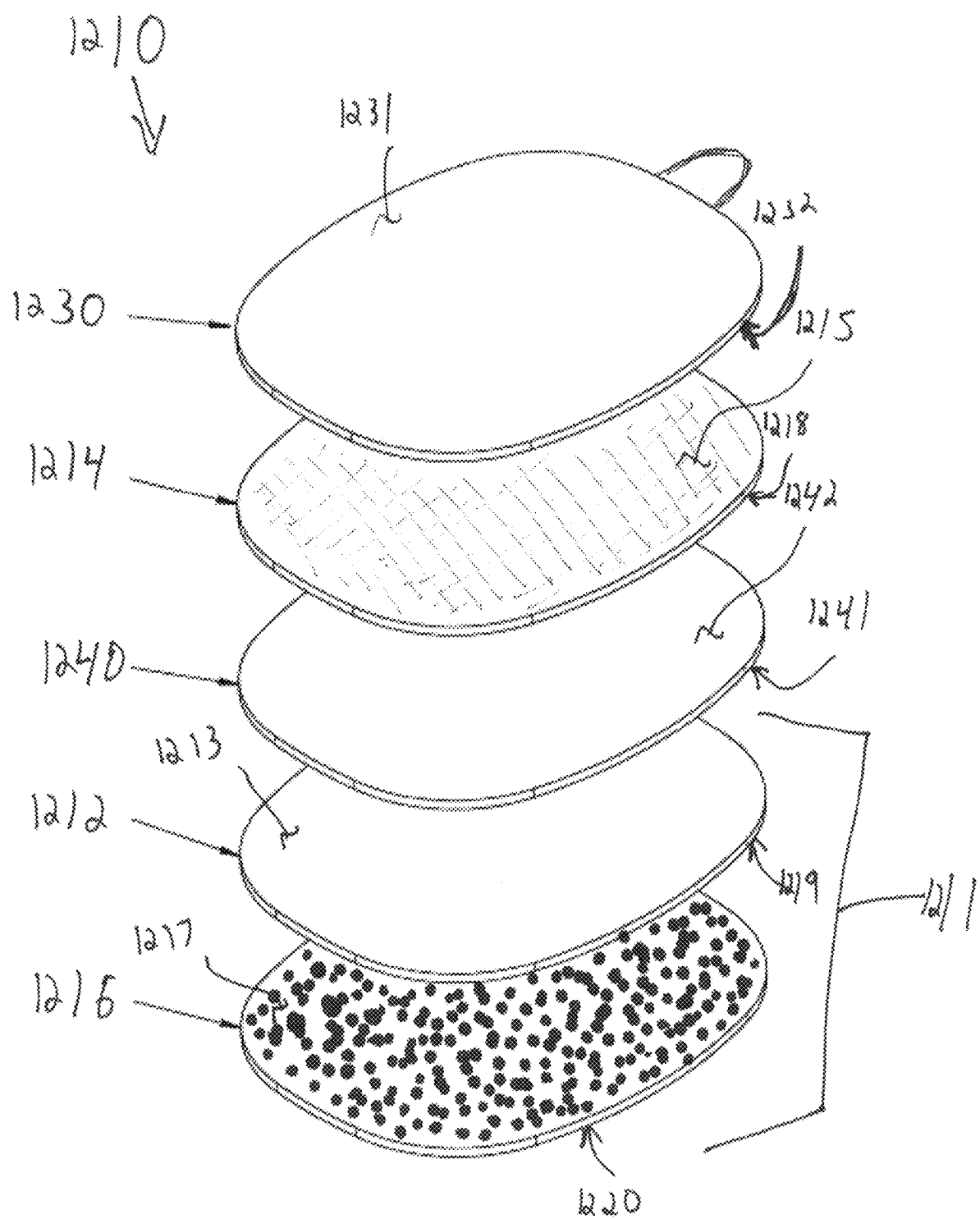
FIG. 25 illustrates another top perspective exploded view of an on-demand agent dispensing patch according to one embodiment of the present disclosure.

As shown in FIGS. 23-25, in some embodiments, the on-demand agent dispensing patch device 1210 may be a flexible patch configured to contain, and provide on-demand dispensing of, the agent via compression of the patch in a thickness direction thereof.

As shown in FIGS. 23-25, in some embodiments, the on-demand agent dispensing patch device 1210 may include at least one reservoir dispenser portion or layer 1211 and at least one attachment portion or layer 1214. The attachment layer 1214 may extend beneath, or underlie, the reservoir dispenser portion 1211. The reservoir dispenser portion 1211 may thereby extend over the attachment layer 1214 in a thickness direction such that a top outer exposed face 1220 of the reservoir dispenser portion or layer 1211 forms the top outer exposed face of the patch device 1210 onto which the agent is applied, and the reservoir dispenser portion 1211 may be configured to absorb, so as to contain, the agent. The on-demand agent dispensing patch device 1210 may further include at least one backer layer 1240 positioned between the attachment layer 1214 and the reservoir dispenser portion 1211 in the thickness direction, as shown in FIGS. 23-25. The backer layer 1240 may be impervious to the agent such that the backer layer 1240 prevents the agent from interacting with the attachment layer 1214. As explained further below, the attachment layer 1214 may comprise an adhesive layer, and the backer layer 1240 may thereby prevent the agent from deteriorating or interfering with the adhesive. Further, the backer layer 1240 may prevent the agent from penetrating through the patch device 1210 in the thickness direction and interacting with the object that the patch device is affixed to, and thereby aid in maintaining or containing the agent in the reservoir dispenser portion 1211. The backer layer 1240 may also provide a consistent solid surface to apply to couple with the attachment layer 1214.

As explained further below, the patch device 1210 may be provided to user "dry" such that the reservoir dispenser portion 1211 (and the other portions of the patch device 1210) is void of the agent absorbed therein. For example, the reservoir dispenser portion 1211 (and the other portions of the patch device 1210) may be completely void of the agent. In such embodiments, the patch device 1210 may form part of a device, system or kit that includes the patch device 1210 and a container of the agent that is separate and distinct from the patch device 1210, as discussed further below with reference to FIGS. 30 and 31.

In some other embodiments, the reservoir dispenser portion 1211 (and the other portions of the patch device 1210) may not have the agent absorbed therein, but the agent may be contained within a manually breakable encapsulation that is provided in, or adjacent to, the reservoir dispenser portion 1211 such that a user can manually break the encapsulation to release the agent and allow the reservoir dispenser portion 1211 to absorb the agent so that the agent is contained within the reservoir dispenser portion 1211. The encapsulation may be a manually breakable shell or envelope. For example, in one exemplary embodiment, the encapsulation may be a foil cover or envelope, a polymer shell or container, or a combination thereof, in whole or in part.

The attachment portion 1214 may comprise an attachment side or surface 1215 that is configured to affix/couple the patch device 1210 to an object (removably or fixedly) (e.g., a user skin or a surface of an inanimate object, as described above and further below). A back side 42 of the backer layer 1240 may be coupled to and overlie at least a portion of a front side 18 of the attachment portion 1214, as shown in FIGS. 23-25. Similarly, a back side 13/17 of the reservoir dispenser portion 1211 may be coupled to and overlie at least a portion of a front side 41 of the backer layer 1240, as shown in FIGS. 23-25. The agent reservoir dispenser portion 1211 is configured to control a dispense rate (i.e., time release) of the volume of an agent to a user at an exposed outer dispensing surface portion 1220 thereof when a user compresses the agent reservoir dispenser portion 1211 in thickness direction. In some embodiments, the agent reservoir dispenser portion 1211 may be refillable after one or more dispensing by applying a volume of the agent to the exposed outer dispensing surface portion 1220 to allow the agent reservoir dispenser portion 1211 to absorb the applied volume of the agent.

The patch device 1210 (e.g., the attachment portion 1214, the backer layer 1240, and the agent reservoir dispenser portion 1211) may be of any size and any shape. In some embodiments, the patch device 1210 may be relatively flat or thin in a thickness direction (e.g., comprise a patch, sheet or like arrangement). In some embodiments, the size and/or shape of the patch device 1210 may correspond to a particular surface/object to which it can be removably coupled to. In this way, the patch device 1210 may be configured to a particular usage (e.g., shaped and sized to removably attach to a particular object or body portion of a user). The patch device 1210 (e.g., the attachment portion 1214 and the agent reservoir dispenser portion 1211) may be relatively flexible, such as easily manually flexible.

The attachment portion 1214 may comprise an adhesive layer configured to removably couple the patch to a surface, the adhesive layer defining the inner or back face/attachment side 1215 of the patch device 1210. As shown in FIGS. 23-25, the attachment side 1215 of the attachment portion 1214 may define the backside or underside of the patch device 1210 when in use, such that the attachment side 1215 defines a backside attachment surface of the patch device 1210 that is configured to abut or overly another surface when the patch device 1210 is coupled thereto. In some embodiments, the attachment portion 1214 may include an adhesive on (or that forms) the attachment surface 1215 that is configured to removably couple the patch device 1210 to a surface.

In some embodiments, the attachment portion 1214 may include an adhesive that is configured to removably couple the patch device 1210 to an inanimate object and/or a user (e.g., skin or clothing of a user). In some such embodiments, the adhesive may comprise a pressure sensitive adhesive (PSA). In some such embodiments, the attachment portion 1214 may be configured to directly removably attach to skin of a user via a biocompatible (and/or medical grade) adhesive, such as a biocompatible PSA, and/or an alcohol resistant adhesive. In some embodiments, the adhesive of the attachment portion 1214 may comprise an acrylic adhesive, an epoxy adhesive, a styrene block co-polymer adhesive or a combination thereof. In some such embodiments, the adhesive of the attachment portion 1214 may comprise an acrylate, such as methacrylates, epoxy diacrylates (i.e., a vinyl resin) or a combination thereof. In some such embodiments, the adhesive attachment portion 1214 may comprise an acrylic-based pressure-sensitive adhesive. In some embodiments, the adhesive of the attachment portion 1214 may comprise spirit gum (mastic), matte spirit gum, liquid latex, thickened latex, flexible collodion or a combination thereof. In some such embodiments, the adhesive may comprise a biodegradable, natural and/or organic adhesive. In some embodiments, the tack, adhesion, shear strength and breathability of the adhesive of the attachment portion 1214 may be configured such that the patch device 1210 is biocompatible with respect to a user's skin.

In some embodiments, the attachment portion 1214 may be formed of an adhesive that covers, surrounds or is otherwise integrated with a scrim layer. The adhesive-scrim construct may form an integrated adhesive-scrim layer that is laid or applied to the backside 1242 of the backer layer 1240 or the back side 1213/1217 of the agent reservoir dispenser portion 1211, and coupled thereto via the adhesive.

In some other embodiments (not shown), the attachment portion 1214 may include a mechanical mechanism and/or physical configuration operative to removably attach the device to a surface or object. For example, the attachment portion 1214 may include and/or comprise a strap, hook-and-loop (or hook-and-hook) fastener, snap fastener, button, strap, elastic, suction cup/member, zipper, threaded post/aperture, magnet or any other fastener mechanism that is configured to removably couple the patch device 1210 to another surface/object. In some embodiments, the attachment portion 1214 comprises a clip or flap member that extends from the back face It is noted that the particular design and configuration can of the attachment portion 1214 can take on any form with respect to a particular surface/object sufficient to removable couple the patch device 1210 to the surface/object.

As shown in FIGS. 24 and 25, in some embodiments, the patch device 1210 may include a removable attachment protective film or liner 1230 extending over the back side 1215 of the attachment layer 1214. An inner side 1232 of the attachment protective liner 1230 may be configured to cover and protect the attachment layer 1214 prior to use (or when otherwise not in use), as shown in FIGS. 24 and 25. As also shown in FIGS. 24 and 25, an outer or back side 1231 of the protective liner 1230 may define the outer back side of the patch device 1210 prior to being affixed to a surface (object/ person). The protective liner 1230 may thereby be configured to be manually removed from the attachment layer 1214 (e.g., peeled off) such that the attachment layer 1214 remains coupled to the patch device 1210 and is effective in coupling the patch device 1210 to a surface. In some embodiments, the protective liner 1230 may comprise a plastic/polymer, coated paper, metallic/metalized layer (e.g., a foil layer or aluminized material layer) or a combination thereof. In some embodiments, the protective liner 1230 may include a tab to aide in manually removing (e.g., peeling) the protective liner 1230 from the attachment surface 1215 of the adhesive layer 1214, as shown in FIGS. 23 and 24.

As noted above, in some embodiments, the patch device 1210 may include at least one at least one backer layer or film 1240 positioned between the attachment layer 1214 and the agent reservoir dispenser portion 1211 in the thickness direction, as shown in FIGS. 23-25. The at least one backer layer 1240 may be substantially impervious to the agent. The backer layer 1240 may support the attachment mechanism 1214 (e.g., an adhesive and/or mechanical fastener) (i.e., the attachment mechanism may be coupled to bottom/back side 1215 of the backer layer). Further, the agent reservoir dispenser portion 1211 may be coupled to and overly (e.g., directly overly) a top/upper side of the backer layer 1240, as shown in FIGS. 23-25.

In some embodiments, the backer layer 1240 comprises at least one layer of a fabric (woven or non-woven), plastic or latex. For example, the backer layer 1240 may comprise a breathable fabric, such as a woven (or non-woven) nylon, polyester or Gore-Tex layer. In some embodiments, the backer layer 1240 may be flexible, and may comprise a water absorbable and/or air permeable fabric layer (particularly in embodiments of the patch device 1210 for use directly on the skin of a user, as described further below). In some other embodiments, the backer layer 1240 may be substantially impervious to the agent and to air. In some embodiments, the backer layer 1240 may comprise a solid sheet of material, such as at least one polymer layer, film or sheet. In some such embodiments, the backer layer 1240 may comprises a polyethylene or polypropylene layer, film or sheet. In some embodiments, the backer layer 1240 may comprise at least one polyethylene layer, polypropylene layer, styrene layer, polyetheretherketone layer, acrylic layer, polyvinyl chloride layer, polyurethane layer, Teflon (Polytetrafluoroethylene) layer, syrlyn layer or a combination thereof. In some embodiments, the backer layer 1240 may comprise a thickness of 0.5-3 mm, such as about 1 mm.

In some embodiments, the patch device 1210 may comprise a dispenser protective liner, film or layer (not shown) extending over the top or outer dispensing surface 1220 of the agent reservoir dispenser portion 1211. An inner side of the dispenser protective liner may be configured to cover and protect the agent reservoir dispenser portion 1211 prior to use (or when otherwise not in use). An outer or top/front side of the protective liner may define the outer front/top side of the patch device 1210 prior to use thereof (e.g., prior to dispensing and/or an application of agent applied to the agent reservoir dispenser portion 1211). The dispenser protective liner may thereby be configured to cover and protect the dispensing surface portion 1220 prior to use (or when otherwise not in use). In some embodiments, the dispenser protective liner may comprise a plastic/polymer or metallic/metalized layer (and potentially an adhesive). Removal of the dispenser protective liner may thereby activate the patch device 1210 for use.

In some embodiments, the dispensing surface portion 1220 (and/or the outer surface of the protective film liner) may include a visual and/or tactile indication (not shown), or be configured such that a visual and/or tactile indication can be drawn or otherwise formed thereon. For example, the dispensing surface portion 1220 (and/or the outer surface of the protective film liner) may include a logo, name, trademark or other visual indication that may enhance the aesthetic look and/or feel of the patch device 1210. As another example, the outer surface of the cover or protective film liner may be configured as a paper, chalkboard or whiteboard type configuration to allow for personalization of the patch device 1210. In some embodiments, the outer surface of the cover or protective liner comprises at least one of a visible light reflective material and an illumination device thereon. In some embodiment the protective liner may include a tab to aide in manually removing (e.g., peeling) the protective liner from the patch device 1210/agent reservoir dispenser portion 1211.

The agent reservoir dispenser portion 1211 may comprise one or more layers and/or more materials. In some embodiments, the agent reservoir dispenser portion 1211 may comprise a single layer comprised of one or more materials. In some other embodiments, as discussed above and further below, the agent reservoir dispenser portion 1211 may comprise one or more reservoir layers or portions 1212 and one or more dispenser layers or portions 1216 that is/are separate and distinct from the one or more agent reservoir layers or portions 1212.

As shown in FIGS. 23-25, in some embodiments, the agent reservoir dispenser portion 1211 of the patch device 1210 may include a dispenser layer 1216 extending over at least one reservoir layer 12. The reservoir layer 1212 is configured to absorb and retain the agent therein, and overlies the attachment layer 1214 in the thickness direction. The dispenser layer 1216 may overly the reservoir layer 1212 in thickness direction, as shown in FIGS. 23-25. The dispenser layer 1216 may comprise a plurality of solid portions and an array of a plurality of openings extending through a thickness thereof, and be configured to inhibit evaporation of the agent, and control a flow of the agent from the agent reservoir dispenser portion 1211 (and in particular the reservoir layer 1212) upon the compression of the patch device 1210 in the thickness direction when the agent is contained within the at least one reservoir layer 1212. The solid portions of the at least one dispenser layer 1216 and portions of the at least one reservoir layer 1212 underlying the plurality of openings of the at least one dispenser layer 1216 may define outer face 1220 of the patch device 1210 (when the protective liner is removed, if provided).

The agent reservoir dispenser portion 1211 is configured to contain the volume of an agent. For example, an agent may be absorbed into the agent reservoir dispenser portion 1211 (e.g., the agent reservoir dispenser portion 1211 may comprise an absorbent pad, layer or portion). As another example, the agent reservoir dispenser portion 1211 may form at least one cavity, opening or cell that contains an agent. The agent reservoir dispenser portion 1211 is also configured to dispense an agent at the dispensing surface portion 1220 to a user who compresses the dice 1210, such as wiping across a portion of the dispensing surface portion 1220. At least a portion of the agent reservoir dispenser portion 1211 thereby automatically controls the speed and duration of the release/flow of the agent at/to the outer dispensing surface portion 1220 (and thereby to a user on an on-demand basis). For example, the agent reservoir dispenser portion 1211 may be configured to draw or otherwise provide a portion of the volume of an agent at or to the dispensing surface portion 1220 such that when a user touches or wipes the dispensing surface portion 1220, some of an agent transfers to the user.

In some embodiments, the reservoir and dispensing functions or processes of the agent reservoir dispenser portion 1211 may be accomplished by a common layer or portion of the agent reservoir dispenser portion 1211. In some other embodiments, the reservoir and dispensing functions or processes of the reservoir and dispensing functions or processes may be accomplished by differing layers or portions of the agent reservoir dispenser portion 1211.

As discussed above and shown in FIGS. 23-25, in some embodiments, the agent reservoir dispenser portion 1211 may comprise at least one reservoir layer or portion 1212 that is configured to absorb and retain the agent therein. In some embodiments, the at least one reservoir layer or portion 1212 may comprise a nonwoven absorbent fabric layer. For example, in one embodiment, the at least one reservoir layer 1212 may be formed of a fabric layer of non-woven polymer fibers, such as non-woven polyethylene and/or polypropylene fibers. In some embodiments, the at least one reservoir layer or portion 1212 may comprise a natural or synthetic non-woven fabric layer. The at least one reservoir layer 1212 may comprise one or more layers of polymer fibers, cotton fibers, silicone fibers, hydrogel or a combination thereof. In some embodiments, the at least one reservoir layer or portion 1212 may comprise one or more layers of a fabric, Gore-Tex, gauze, an absorbing gel, a polymer, paper, a foam or a combination thereof.

In some embodiments, the at least one reservoir layer or portion 1212 may be formed of a (woven or non-woven) cloth or fabric (e.g., a cotton, nylon, polyester or the like layer/portion), Gore-Tex, gauze, absorbing gel (e.g., a hydrogel), flashspun high-density polyethylene (e g, Tyvek), porous/filter paper, plastic film, foam, hydrocolloid, alginate, polysaccharide pastes, granules and/or beads, or a combination thereof. For example, is some embodiments the reservoir portion 1212 may comprise one or more layers of cotton, polyester, silicone, polyurethane, polyamide, polyethylene, hydrogel or a combination thereof. In some such embodiments, the reservoir portion 1212 may include a cotton fabric layer or portion, a nylon fabric layer or portion, a polyester fabric layer or portion, a flashspun high-density polyethylene fiber layer or portion, a hydrogel layer or portion, a flexible polyamide net coated with silicone layer or portion, a hydrogel layer or portion formed of hydrophilic polymers, or a combination thereof.

In some embodiments, the at least one reservoir layer or portion 1212 may be configured to absorb and retain within the range of about 2 grams and about 50 grams of the agent, and/or have a detached agent capacity within the range of about 1,000 g/mm2 and about 2,500 g/mm2. In some embodiments, the at least one reservoir layer 1212 comprises an agent absorbency rate of at least 5 g/sec for at least the first 5 seconds of water contact. The at least one reservoir layer or portion 1212 can be configured such that when the agent is contained/absorbed therein, a compressive force acting in the thickness direction and applied to the outer dispensing surface 1220 of the patch device 1210 of at least 1 gram/mm2 causes the agent to flow through from the at least one reservoir layer or portion 1212 and onto the outer dispensing surface 1220 (potentially trough apertures in an outer dispenser layer 1216, as discussed further below) and/or an onto an object at the outer dispensing surface 1220.

As discussed above and shown in FIGS. 23-25, in some embodiments, the agent reservoir dispenser portion 1211 may comprise at least one dispenser layer or portion 1216 comprising a plurality of solid portions and an array of a plurality of openings or apertures extending through a thickness thereof, the at least one dispenser layer 1216 configured to inhibit evaporation of the agent, and control a flow of the agent from the at least one reservoir layer 12, upon the compression of the patch device 1210 in the thickness direction when the agent is contained within the at least one reservoir layer.

The at least one dispenser layer 1212 may comprise at least one perforated or micro porous film or layer. In some embodiments, the at least one dispenser layer 1212 comprises a sheet or layer of material that is impervious to the agent and/or impervious to air. In some embodiments, the at least one dispenser layer 1212 comprises a polymer layer. In some embodiments, the at least one dispenser layer 1212 comprises at least one polyethylene layer, polypropylene layer, styrene layer, polyetheretherketone layer, acrylic layer, polyvinyl chloride layer, polyurethane layer, Teflon (Polytetrafluoroethylene) layer, syrlyn layer or a combination thereof.

In some embodiments, the solid portions of the at least one dispenser layer 1212 may comprise within the range of about 1210% and about 65% of the total area of the outer dispensing face/side 1220 of the patch device 1210. In some embodiments, the plurality of openings of the at least one dispenser layer 1212 comprise a total area within the range of about 50 mm2 and about 12300 mm2 at the outer dispensing face/side 1220 of the patch device 1210. In some embodiments, each of the plurality of openings of the at least one dispenser layer 1212 comprise a total area within the range of about 0.05 mm2 and about 0.3 mm2 at the outer dispensing face/side 1220 of the patch device 1210.

At least the dispensing portion 1212 of the agent reservoir dispenser portion 1211 may be configured to control the amount and/or rate at which an agent moves or is drawn therethrough (e.g., via capillary action) and to the dispensing surface portion 1220. The agent reservoir dispenser portion 1211 is thereby configured to meter/control the release or dispensing of an agent to/from/at the dispensing surface portion 1220. For example, at least one of the pore/perforation size, pore/perforation count/number, density and thickness of the at least one dispenser layer 12, and capillary action of the agent reservoir dispenser portion 1211, may be configured to control the amount and/or rate at which an agent moves or is drawn to and through the at least one reservoir layer/portion 1212 and the at least one dispenser layer 1216 to the dispensing surface portion 1220. The agent reservoir dispenser portion 1211 may be configured such that a particular dosage of an agent flows through the agent reservoir dispenser portion 1211 and the dispensing surface portion 1220 when a certain pressure (e.g., a certain magnitude, area, direction, etc.) is applied thereto by a user such that the particular dosage of an agent is transferred to the dispensing surface portion 1220 (and thus a user or surface applying the compression/pressure) thereby.

In some embodiments, the patch device 1210 (formed of the agent reservoir dispenser portion 1211 (e.g., comprising the at least one reservoir layer/portion 1212 and the at least one dispenser layer/portion 1216), the at least one backer layer/portion 1240 and at least one attachment layer/portion 1214) being saturated with a liquid or gelatinous agent, such as those disclosed herein, is configured such that the agent is available/dispensable at the dispensing surface portion 1220 via touching or swiping of the dispensing surface portion 1220 by a user for at least 2 hours, at least 3 hours, at least 4 hours, at least 5 hour or at least 6 hours after the dispensing surface portion 1220 is initially exposed to air. In some embodiments, the patch device 1210 is configured such that when a liquid or gelatinous agent, such as those disclosed herein, is absorbed within the at least one reservoir layer 1212, the patch device 1210 is configured such that no more than 5 grams of the agent evaporates over 1.5 hours in an ambient environment of non-moving/stagnant air at 1220 degrees Celsius.

The agent may be any biocompatible disinfectant (i.e., safe and effective for use with humans, such as on human skin), such as any topical disinfectant effective in killing and/or preventing reproduction of disease causing pathogens (such as viruses and bacteria, for example) when an agent and the pathogens physically interact. An agent may be effective on disinfecting a person's skin and in addition to the surface of an inanimate object (such as a surface comprising plastic, metal, glass, paper, cardboard, etc.). For example, an agent may comprise an alcohol sanitizer and/or a non-alcohol sanitizer. In some embodiments, the agent may comprise a disinfectant comprising ethyl, isopropyl, ethanol (ethyl alcohol), triclosan, triclocarban, benzalkonium chloride, benzethonium chloride or a combination thereof. In some embodiments, the agent may comprise a disinfectant comprising ethanol (ethyl alcohol). In some embodiments, the agent may comprise a dynamic viscosity within the range of about 4 (Pa·s)(m2/s) and about 1215 (Pa·s)(m2/s) at 1220 degrees Celsius. In some embodiments, the agent may comprise a medicant or vitamin, insecticide, fragrance, food product, cleaning product, paint and/or oil.

In some embodiments, an agent comprises ethyl, isopropyl, ethanol (ethyl alcohol), triclosan, triclocarban, benzalkonium chloride, benzethonium chloride or a combination thereof. In some embodiments, an agent comprises 1,2-hexanediol, ammonium bicarbonate, ammonium carbonate, benzalkonium chloride, benzalkonium chloride, chlorine dioxide, citric acid, dodecylbenzenesulfonic acid, ethanol, ethyl, glutaraldehyde, glycolic acid, hydrochloric acid, hypochlorous acid, isopropyl, isopropanol, lactic acid, L-lactic acid, octanoic acid, peroxyacetic acid, peroxyoctanoic acid, phenolic, potassium peroxymonosulfate, quaternary ammonium, silver, silver ion, sodium carbonate, sodium carbonate peroxyhydrate, sodium chloride, sodium chlorite, sodium dichloroisocyanurate, sodium dichloroisocyanurate dihydrate, sodium dichloro-S-triazinetrione, sodium hypochlorite, thymol, triethylene glycol, triclosan, triclocarban, alcohol (e.g., at least 60% by volume), aloe gel, vinegar, an essential oil, aromatherapy compound, or a combination thereof, In some embodiments, an agent may comprise at least one essential oil, such as geranium, lavender, sweet marjoram, neroli, palmarosa, peppermint, petitgrain, rose, tea tree, thyme, linalool oil or a combination thereof. In some embodiments, an agent may be in liquid or gel form. In some embodiments, an agent may comprise a solution and/or a suspension, and may include at least solid disinfectants.

It is also specifically disclosed herein that although embodiments of the on-demand dispensing devices (and related methods) of the present disclosure are described with respect to containing and dispensing a disinfectant (i.e., on-demand disinfectant dispensing devices), the devices may equally be employed to dispense any other solid, liquid or gel agent. For example, the devices may contain and be configured to dispense any pleasant or foul odorous and/or tasteful material (e.g., perfume, attractant/detractant-repellant (e.g., bug or insect repellant, etc.). As another example, the devices may contain and be configured to dispense a skin lotion (e.g., moisturizer, sunscreen, etc.), antiperspirant/deodorant, medication/medicine, lubricant, friction-enhancing material (e.g., a sticky or gritty material), any other biocompatible material, biohazard material or a combination thereof. In some such embodiments, the medication/medicine may be a medicant, a vitamin (vitamin C, B12, etc.) or supplement (e.g., caffeine, nicotine, etc.), a cannabinoid (e.g., cannabidiol (CBD)), delta-9-tetrahydrocannabinol (THC) or a food product (e.g., sugar, candy, etc.). As a further example, the devices may contain and be configured to dispense a paint. As another example, the devices may contain and be configured to dispense a cleaning product. As another example, the devices may contain and be configured to dispense a food product or foodstuff.

The layers or portions of the patch device 1210 may be coupled together via any means, such as any mechanical and/or chemical mode or method. In some embodiments, the layers or portions of the patch device 1210 are adhered to each other. In some embodiments, the layers or portions of the patch device 1210 are bonded to each other. In some such embodiments, the layers or portions of the patch device 1210 are bonded to each other via the materials making up the layers or portions. For example, in some embodiments, at least some of the adjacent layers or portions of the patch device 1210 may be bonded to each other via the layers or portions being heated above their melting or softening points and becoming bonded together. In some such embodiments, the at least one reservoir layer 1212 and the at least one dispenser layer 1216, and/or the at least one reservoir layer 1212 and the at least one backer layer 1240, may be heat, radio-frequency and/or ultrasonic welded together. In some embodiments, if the at least one reservoir layer 12, the at least one dispenser layer 1216 and/or the at least one backer layer 1240 are formed of more than one overlapping layers, such layers may be bonded together.

Figure 26:
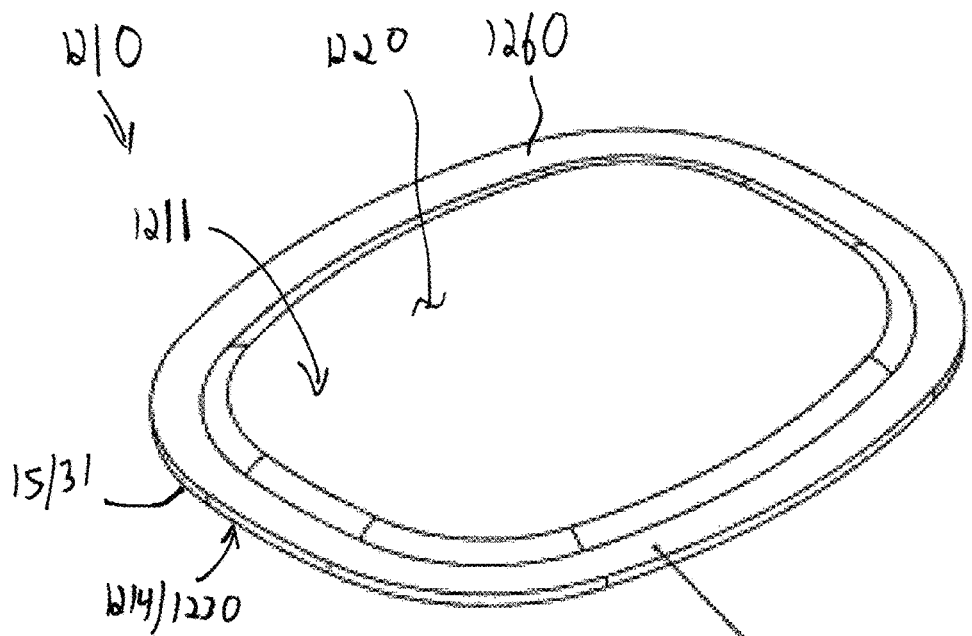
FIG. 26 illustrates a top perspective view of an on-demand agent dispensing patch according to one embodiment of the present disclosure.
Figure 27:
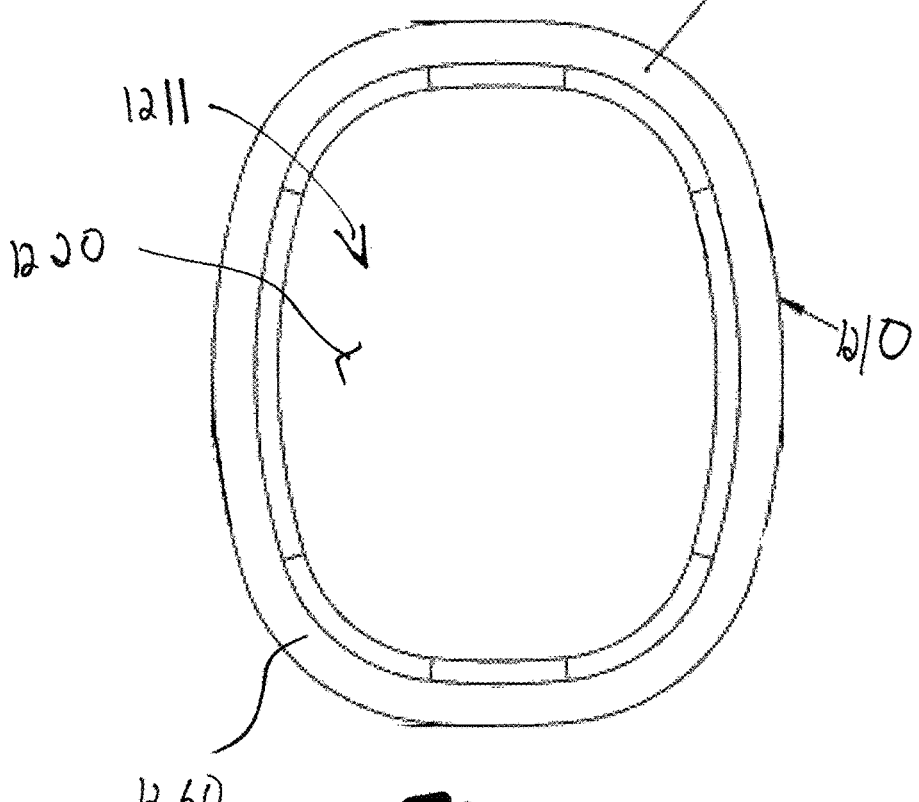
FIG. 27 illustrates a top view of the on-demand agent dispensing patch of FIG. 26 according to one embodiment of the present disclosure.
Figure 28:
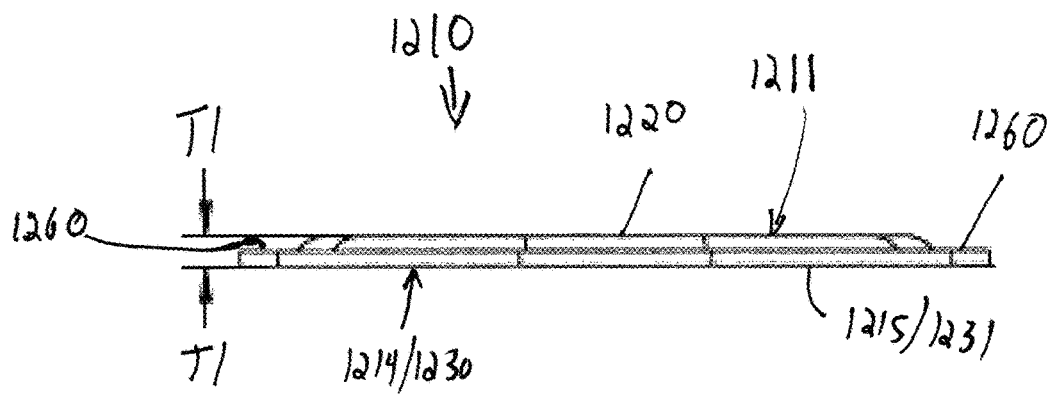
FIG. 28 illustrates a side view of the on-demand agent dispensing patch of FIG. 26 according to one embodiment of the present disclosure.

As shown in FIGS. 26-28, in some embodiments, the patch device 1210 may be bonded or adhered together such that an outer peripheral portion 60 is compressed together as compared to an interior or central portion of the patch device 1210. The outer peripheral portion 60 may thereby define a total/maximum thickness T1 that is less than that of the interior or central portion of the patch device 1210. In some embodiments, the outer peripheral portion 60 may be formed via at least some of the layers/portions of the patch device 1210 being compressed and bonded together, such as via heat, radio-frequency and/or ultrasonic welded together.

In some embodiments, the patch device 1210 may define a total/maximum thickness within the range of about 0.05 mm and about 3 mm. In some embodiments, the outer peripheral portion 60 may thereby define a total/maximum thickness T1 that less than 75%, such as about 50%, that of the interior or central portion of the patch device 1210.

The periphery of the patch device 1210 may define any shape and size. For example, as shown in FIGS. 26 and 27, in one exemplary embodiment the patch device 1210 may define an oval or oblong shape such that a length of the patch device 1210 is greater than a width of the patch device 1210 (such as a width of within the range of 1 inch to 4 inches, and a length of 1.5 to 1210 inches). In some other exemplary embodiments (not shown), the patch device 1210 may define a circular shape (e.g., with a diameter within the range of 1 inch to 4 inches, or within the range of 1 inch to 2.5 inches).

Figure 29:
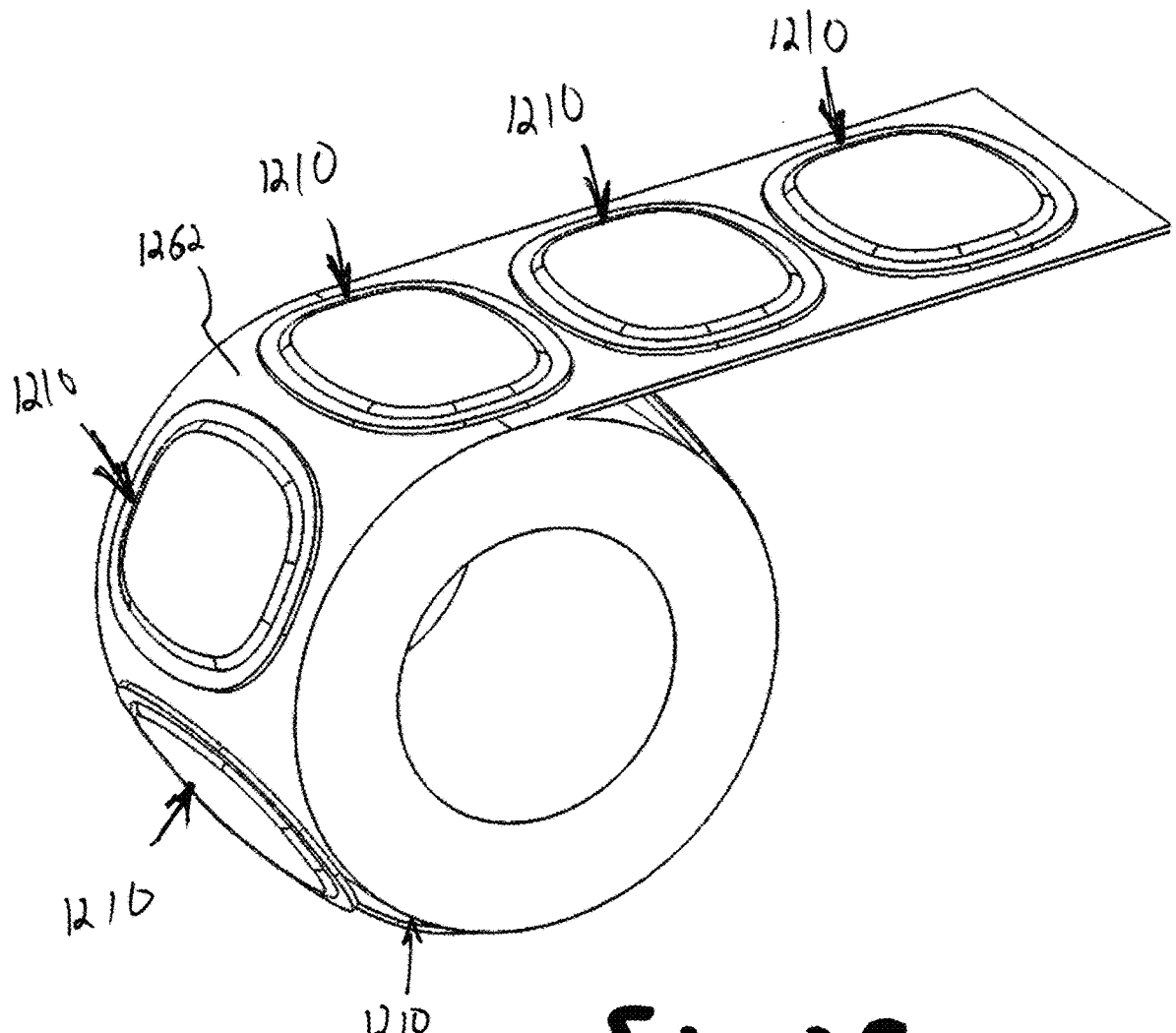
FIG. 29 illustrates a plurality of the on-demand agent dispensing patch of FIG. 26 provided on a support member according to one embodiment of the present disclosure.
Figure 30:
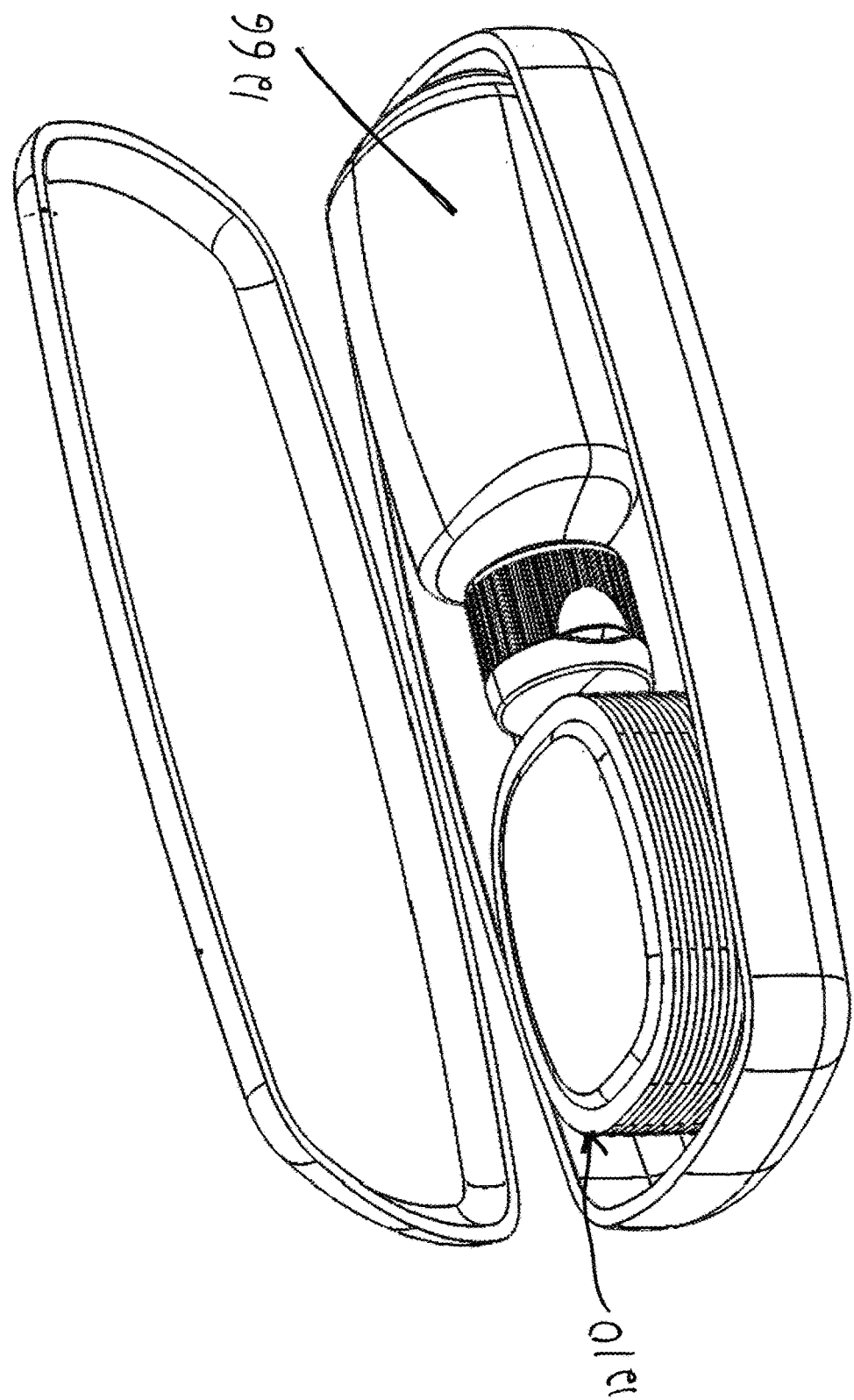
FIG. 30 illustrates a top perspective view of a kit comprising a plurality of on-demand agent dispensing patches and a container of a volume of an agent according to one embodiment of the present disclosure.

As shown in FIGS. 22-28, a kit, system or device according to the present disclosure may include one patch device 1210, or may include a plurality of patch devices 1210 as shown in FIGS. 29 and 30. Further, as noted above, the one or more patch devices 1210 may or may not include an agent incorporated into the patch device 1210. For example, the one or more patch devices 1210 may be entirely void of an agent to be dispensed, or at least void of an agent being absorbed in the reservoir dispenser portion 1211 (e.g., absorbed in the at least one reservoir layer 12).

As shown in FIG. 29, in some embodiments, a kit, system or device a kit, system or device according to the present disclosure may include a plurality of the patch devices 1210 provided or coupled to a substrate or carrier material 1262. In some embodiments, the plurality of the patch devices 1210 may be coupled to the substrate or carrier material 1262 via the attachment portion 1214 thereof (e.g., an adhesive layer). In some other embodiments, the plurality of the patch devices 1210 may be coupled to the substrate or carrier material 1262 via an additional adhesive, member or mechanism.

Figure 31:
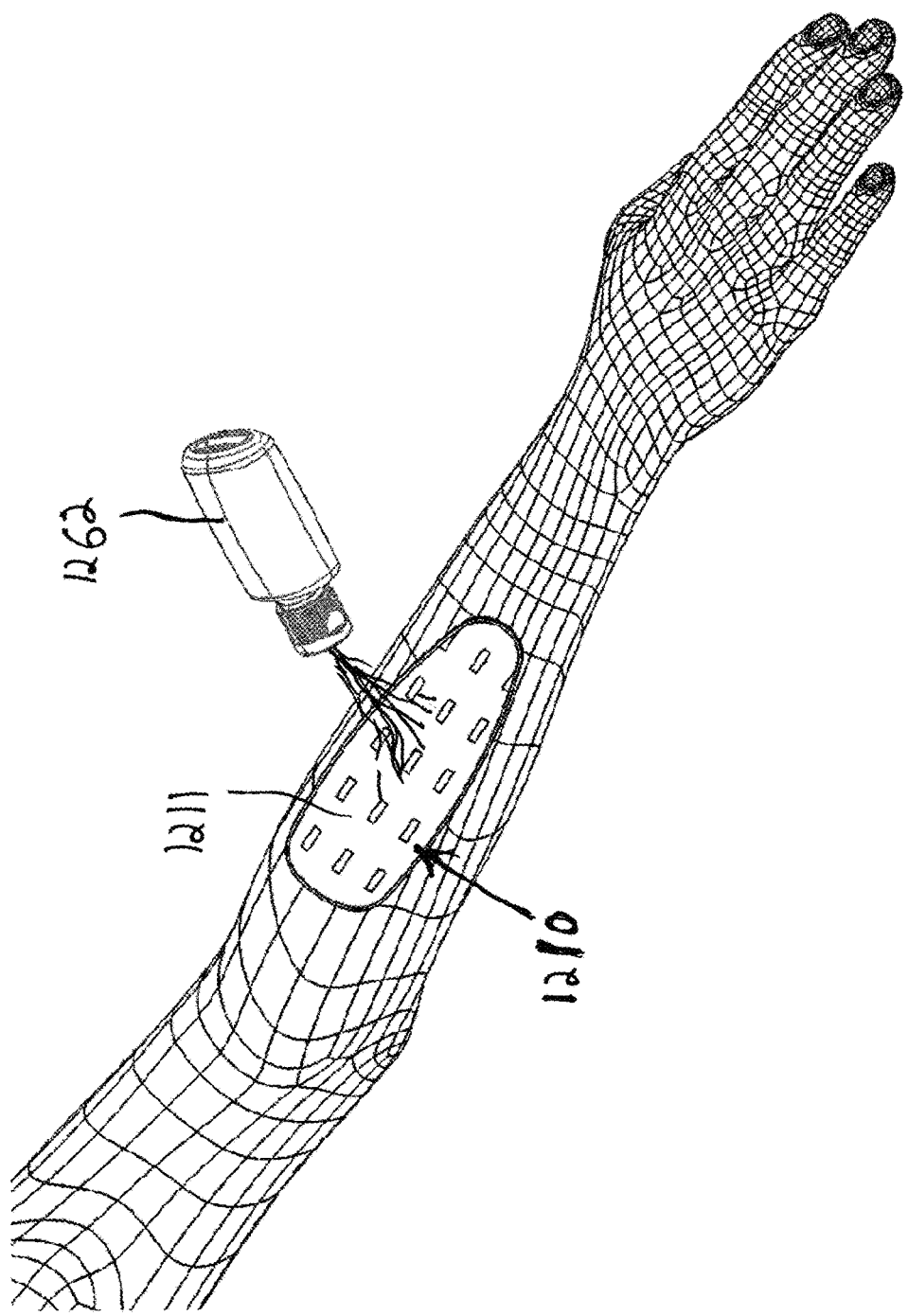
FIG. 31 illustrates a top perspective view of the application of the agent of the container of the kit of FIG. 8 on an on-demand agent dispensing patch of the kit of FIG. 30 coupled to a user according to one embodiment of the present disclosure.

As shown in FIG. 30, in some embodiments a kit, system or device according to the present disclosure may include one or more of the patch devices 1210 (e.g., a plurality of the patch devices 1210) and a container 1266 of an agent to be dispensed by the one or more patch devices 1210. For example, as disclosed above, the agent may be a disinfectant/sanitizer. In such embodiments, the one or more patch devices 1210 can be provided void of the agent, and the agent can be applied to a patch device 1210 when an on-demand dispensing supply of the agent is desired. For example, as shown in FIG. 31, a "dry" patch device 1210 devoid of the agent may be attached or coupled to a surface, such as adhered to a user, and the container 1266 of the agent may be utilized by the user to apply a volume of the agent to the dispensing surface 1220 so that the agent is absorbed into the reservoir dispenser portion 1211 (e.g., absorbed into the at least one reservoir layer 1212).

The container 1266 can thereby be separate and distinct from the one or more patch devices 1210, and the one or more patch devices 1210 can be provided and stored prior to use with the agent reservoir dispenser portion 1211 (and the other portions) of the one or more patch devices 1210 being void of the agent, such as the agent not being absorbed in the at least one reservoir layer 1212 thereof.

In an alternative embodiment, one or more containers 1266 of an agent may be integrated into each of the one or more patch devices 1210 such that the agent is contained and not absorbed in the at least one reservoir layer 12, but configured such that release of the agent form the container causes the agent to flow into/be absorbed by the agent reservoir dispenser portion 1211 (e.g., the at least one reservoir layer 1212). For example, the one or more containers 1266 of an agent may be embedded within, or positioned adjacent or near, the agent reservoir dispenser portion 1211 (e.g., the at least one reservoir layer 1212) of a patch device 1210. As also described above, in such embodiments, the one or more containers 1266 may be manually breakable or openable so that the agent can be selectively manually released from the one or more containers 1266.

Figure 32:
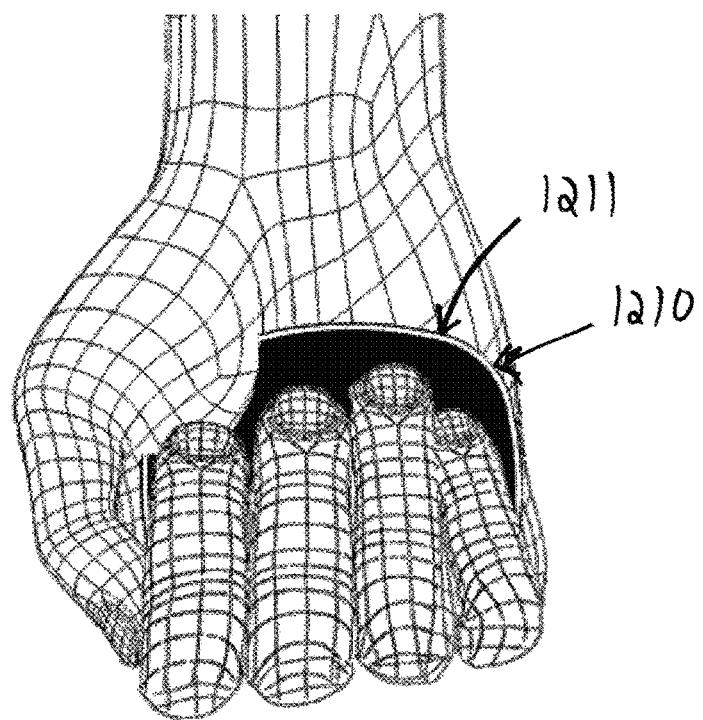
FIG. 32 illustrates a top perspective view of a user compressing an on-demand agent dispensing patch to dispense a volume of agent from an on-demand agent dispensing patch according to one embodiment of the present disclosure.

After a volume of the agent is provided on the patch device 1210 via the container 1266, and the agent (e.g., at least a majority thereof) is absorbed into the agent reservoir dispenser portion 1211 (e.g., into the at least one reservoir layer 1212), a user may compress the patch device 1210 in the thickness direction to force a certain dose or volume of the agent from the agent reservoir dispenser portion 1211 and to the user at the dispensing surface 1220. For example, as shown in FIG. 32, a user may compress and "crunch" a device patch 1210 via a hand that the patch device 1210 is coupled to. It is noted such a motion/method could also break an encapsulated agent contained within/on the patch device 1210 to release the agent into the agent reservoir dispenser portion 1211, and also dispense the agent.

Figure 33:
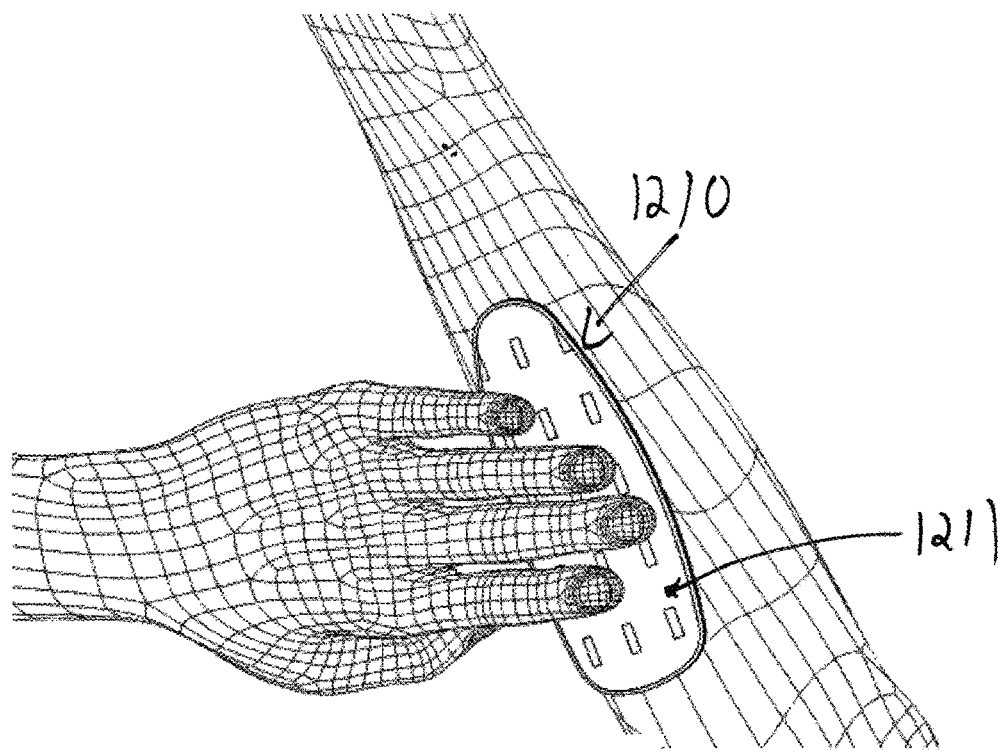
FIG. 33 illustrates another top perspective view of a user compressing an on-demand agent dispensing patch to dispense a volume of agent from an on-demand agent dispensing patch according to one embodiment of the present disclosure.
Figure 34:
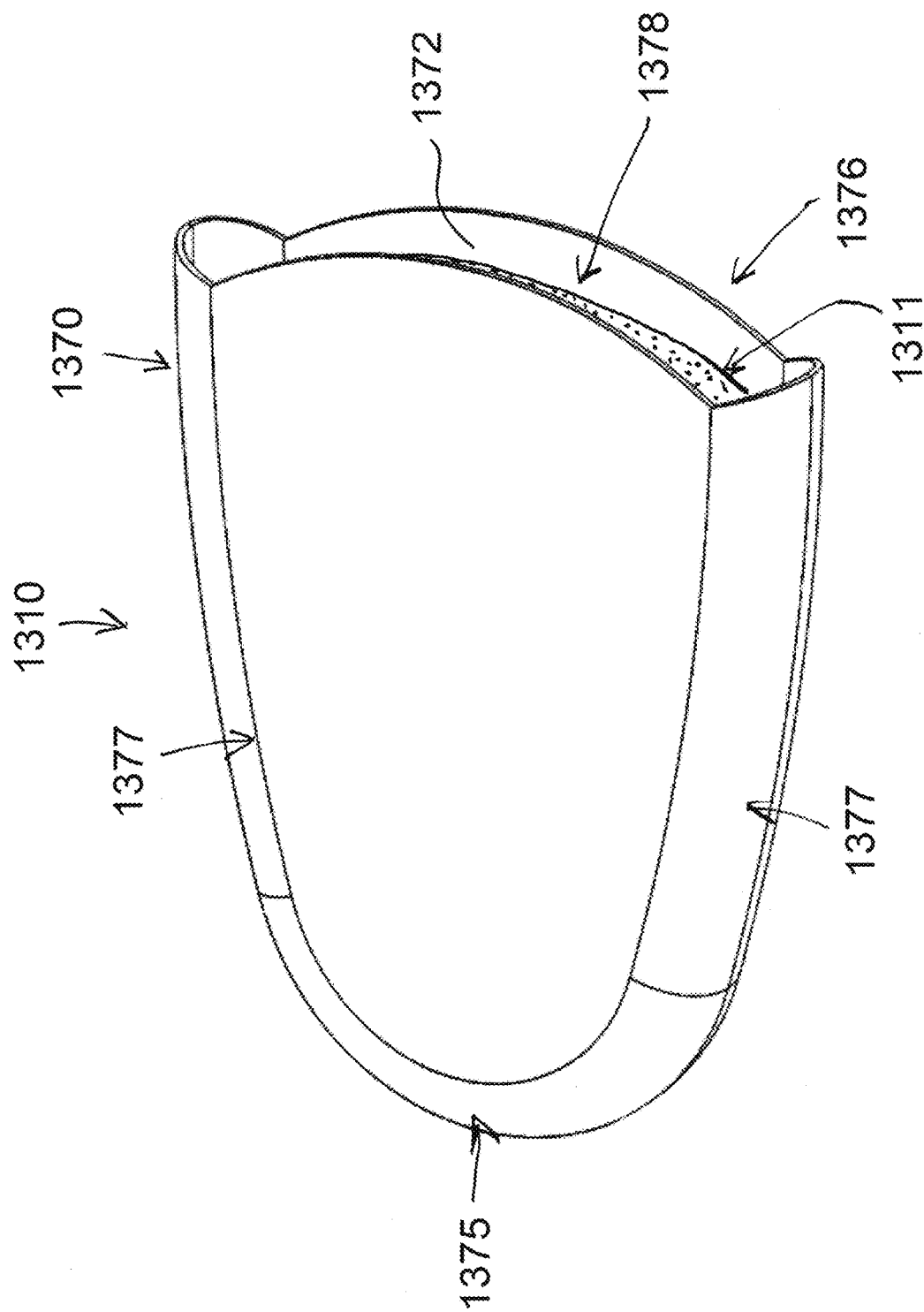
FIG. 34 illustrates a top perspective view of an on-demand agent dispensing pocket patch according to one embodiment of the present disclosure.

As another example, as shown in FIG. 33, a user may swipe the dispensing surface 1220 to compress a length of the patch device 1210 in the thickness direction to force a certain dose or volume of the agent from the agent reservoir dispenser portion 1211 and to the user at the dispensing surface 1220. In such a method, the patch device 1210 may be coupled to a surface (e.g., a portion of a user, such as a user's forearm, as an example) that is remote from a user's hand, and the user may use the hand to swipe the patch device 1210 and dispense a volume of the agent from the patch device 1210.

In some embodiments, the patch device 1210 may be configured such that it can be coupled to a user on a passive piece of clothing (e.g., hat, shirt, coat, pant, belt, shoe, scarf, glove, sock, etc.) or another inanimate object (sweatband, kinesiology/muscle tape, heat/cool pads, helmet, protective pad/brace/splint/cast, headphones, luggage, personal accessories, luggage, wallet, hand bag/purse, athletic equipment, etc.) that is configured to couple to (i.e., be worn or carried by) the user. The patch device 1210 may thereby be removably coupled to a passive portion of the user that is spaced from the point/portion of contact of the user that the user wishes to apply the agent to via touching of the dispensing surface portion 1220. As noted above, the attachment portion 1214 may include and adhesive or mechanical connection mechanism that is configured to attach to a specific or general surface, such as to the clothing or another inanimate object on/coupled to the user. In use, the user can thereby removably couple the patch device 1210 to their clothing or another inanimate object on/coupled to the user on a passive portion of the user (such as but not limited to over the user's forearm, upper arm, chest, waist or thigh), and touch or wipe the dispensing surface portion 1220 with one or more of their hands when the user desires to apply the agent thereto (e.g., disinfect) their one or more of their hands (or another body portion or inanimate object touched by the user's one or more hand). When the user desires, the patch device 1210 can be removed from the clothing or another inanimate object on/coupled to the user (preferably without damaging the surface outer surface thereof).

As also discussed above, in some embodiments, the attachment portion 1212 (and potentially the reservoir dispenser portion 1211) may be configured such that the patch device 1210 is worn by a user directly on their skin. The attachment portion 1214 may thereby be configured to be biocompatible with a person's passive skin, and the patch device 1210 may be breathable or otherwise resistant to causing the user to sweat beneath the device 1210. For example, the patch device 1210 may be configured to have an "invisible" feel when attached to a user's skin. The patch device 1210 may thereby be removably coupled to a user's skin. In use, the user can thereby removably couple the patch device 1210 directly to their skin (such as but not limited to on the user's hand, forearm, upper arm or thigh), and touch or wipe the dispensing surface portion 1220 with one or more of their hands when the user desires to apply the agent (e.g., a disinfectant) to their one or more of their hands (or another body portion or inanimate object touched by the user's one or more hand). When the user desires, the patch device 1210 can be removed from the skin of the user (preferably without hurting, irritating or otherwise damaging the skin).

In some exemplary embodiments, the patch device 1210 may be configured (e.g., shaped and sized) to removably couple to and extend over (e.g., cover) the palm and/or at least a portion of at least one finger of a hand of a user. As another example, in some embodiments, the patch device 1210 may be configured (e.g., shaped and sized) to removably couple to and extend over (e.g., cover) just a portion of the palm of a hand of a user, as shown in FIG. 32. In some other exemplary embodiments, the patch device 1210 may be configured (e.g., shaped and sized) to removably couple to and extend over (e.g., cover) at least a portion of an interior side of a finger of a hand of a user. As another example, in some embodiments, the patch device 1210 may be configured (e.g., shaped and sized) to removably couple to and extend over (e.g., cover) just a portion of the forearm of an arm of a user, as shown in FIGS. 31 and 33, for example. In some other exemplary embodiments, the patch device 1210 may be configured (e.g., shaped and sized) to removably couple to and extend over (e.g., cover) at least a portion of an elbow of an arm of a user.

In yet another embodiment, the patch device 1210, such as at least the attachment portion 1214, may be configured to attach to an inanimate object (not shown) that is not worn or carried by a user. For example, the attachment portion 1214 may be configured to removably (or fixedly) attach to a handle, knob, switch, arm rest, seat, steering wheel, transmission/shift lever, athletic equipment, medical equipment, office equipment, culinary equipment, military/defense equipment, packaging (e.g., a shipping or product packaging), furniture, pet product, or any other item or surface that is communal (i.e., likely to be touched by more than one person) or that is positioned within/near a communal space area, surface or item.

In some embodiments, the patch device 1210 may be configured such that the appearance of a portion of the patch device 1210, such as the dispensing surface portion 1220, changes as the volume of an agent within the reservoir dispenser portion 1211. In this way, the patch device 1210 may automatically visually and/or tactically indicate the particular volume of an agent within the reservoir dispenser portion 1211, and thereby available to the user via the dispensing surface portion 1220, at any particular time. It is noted that the patch device 1210 may be configured to variably change colors as the volume of an agent changes, or may only change colors once when the level of an agent is at least substantially depleted and/or the level available to a user is inadequate (to disinfect, for example). For example, the reservoir dispenser portion 1211 and/or an agent may be configured to change color with changes in the temperature, pH and/or dryness/wetness (e.g., liquid vs. solid form) thereof. As the volume of an agent within the reservoir dispenser portion 1211 decreases (such as from being dispensed via the dispensing surface portion 1220, to a user and/or evaporating (or otherwise changing states), the temperature, pH and/or dryness/wetness (e.g., liquid/solid state) of the reservoir dispenser portion 1211 and/or an agent may change and cause a color change, such as with respect to a material/component/chemical/additive of or within the reservoir dispenser portion 1211 and/or an agent. In some embodiment, the reservoir dispenser portion 1211 and/or an agent may be configured to change color with time, independently of the actual volume of an agent. For example, the reservoir dispenser portion 1211 and/or an agent may include a pigment, ink dye or the like that degrades or absorbs over time such that the color thereof changes over time. In this way, the color of the patch device 1210 can indicate to a user how long the patch device 1210 has been in use, and thereby an indication of the potential state of the volume of an agent (e.g., an agent may evaporate over time).

As another example, the patch device 1210 may be configured such that the size, shape, surface texture and/or other physical dimension/aspect of the patch device 1210 changes as the volume of an agent within the reservoir dispenser portion 1211 decreases to provide a tactile indication of the level thereof. For example, the dispensing surface portion 1220 may include raised bumps or the like that flatten/shorten as the volume of an agent within the reservoir dispenser portion 1211 decreases.

Another exemplary on-demand dispensing device 1310 that is configured as a pocket patch device 1310 is shown in FIGS. 34-37. The device 1310 of FIGS. 34-37 is substantially similar to the device 10 of FIG. 1-7, the device 110 of FIG. 8, the device 210 of FIGS. 9 and 10, the device 310 of FIG. 11, the device 410 of FIG. 12, the device 510 of FIGS. 13-15, the device 610 of FIG. 16, the device 710 of FIG. 17, the device 810 of FIG. 18, the device 910 of FIG. 19, the device 1010 of FIGS. 20 and 21, the device 1110 of FIG. 22 and the device 1210 of FIGS. 23-33, and therefore like reference numerals preceded with "12" are used to indicate like components, aspects, functions, processes or functions, and the description above directed to thereto equally applies, and is not repeated for brevity and clarity purposes.

As shown in FIGS. 34-37, the device 1310 comprises a flexible agent-impervious pocket 1370 comprising a front portion or face 1374, a back portion or face 1376, a bottom portion 1375, a top portion 1376, lateral side portions 1377 that form an agent-impervious interior cavity or pocket 1375 between inner sides of the front and back faces, the lateral side portions 1377 and above the bottom portion 1375. The interior cavity 1375 is thereby closed at the bottom portion 1375 and the lateral side portions 1377 (and at the front and back sides 1374, 172), as shown in FIGS. 34-37. As also shown in FIGS. 34-37 the agent-impervious pocket 1370 is open or openable at a top or upper end portion 1376 on the pocket 1370. The open top end 1376 thereby provides access into the interior cavity 1375.

The pocket 1370 may be impervious to an agent such that the agent (e.g., a liquid or gelatinous agent) contained within the interior cavity 1375 (as explained further below) is unable to flow or otherwise pass through the front portion 1374, the back portion 1376, the bottom portion 1375 and the lateral side portions 1377. In some embodiments, the pocket 1370 may be impervious to air such that air is unable to pass into the interior cavity 1375 (or pass therefrom) through the front portion 1374, the back portion 1376, the bottom portion 1375 and the lateral side portions 1377.

The pocket 1370 may be formed from or comprise the same or similar materials as the backer layer 1340 and/or dispenser layer 1316 as disclosed herein. For example, in some embodiments, the pocket 1370 (e.g., the front portion 1374, the back portion 1376, the bottom portion 1375 and the lateral side portions 1377) may be formed a solid sheet of material. In some embodiments, the pocket 1370 may be formed of or comprise a polymer layer or film. In some embodiments, the pocket 1370 may be formed of or comprise at least one polyethylene layer, polypropylene layer, styrene layer, polyetheretherketone layer, acrylic layer, polyvinyl chloride layer, polyurethane layer, Teflon (Polytetrafluoroethylene) layer, syrlyn layer or a combination thereof.

In some embodiments, the front portion or face 1374 and/or the back portion or face 1376 may be the backer layer 1340 of the device 10 described herein. In such embodiments, an additional backer layer 1340, or the two backer layers 1340, 1340, may be coupled together (e.g., bonded) at their lateral sides and bottom end portions to form the flexible agent-impervious pocket 1370.

As shown in FIGS. 34-37, at least one reservoir dispenser portion or layer 1311 may be coupled within the interior cavity 1375 such that the dispensing surface portion 120 is exposed to the interior of the interior cavity 1375. For example, a reservoir dispenser portion 1311 may be coupled to an inner side of the front portion 1374 within the interior cavity 1375, a reservoir dispenser portion 1311 may be coupled to an inner side of the back portion 1372 within the interior cavity 1375, or a first reservoir dispenser portion 1311 may be coupled to the inner side of the front portion 1374 within the interior cavity 1375 and a second reservoir dispenser portion 1311 may be coupled to the inner side of the back portion 1372 within the interior cavity 1375. It is noted that the reservoir dispenser portion 1311 may be coupled to the back portion 1372 and/or the front portion 1374 via an adhesive, bonded thereto and/or a mechanical attachment. In some embodiments, a backer layer may be positioned/coupled between the reservoir dispenser portion 1311 and a respective one of the back portion 1372 or the front portion 1374.

As discussed in detail above, the reservoir dispenser layer 1311 is configured to absorb and retain a liquid or gelatinous agent therein, and control a flow of the agent therefrom upon/via compression of the reservoir dispenser layer 1311 retained/absorbed therein. As also discussed above, the reservoir dispenser portion 1311 may initially be void of the agent, or at least void of the agent being absorbed therein, and applied from a separate and distinct container. As another example, the reservoir dispenser portion 1311 may not contain an agent absorbed therein, but the pocket patch device 1310 may contain an encapsulated or container of the agent that can be manually broken or otherwise opened to allow the agent to flow to and be absorbed by the reservoir dispenser portion.

Figure 37A:
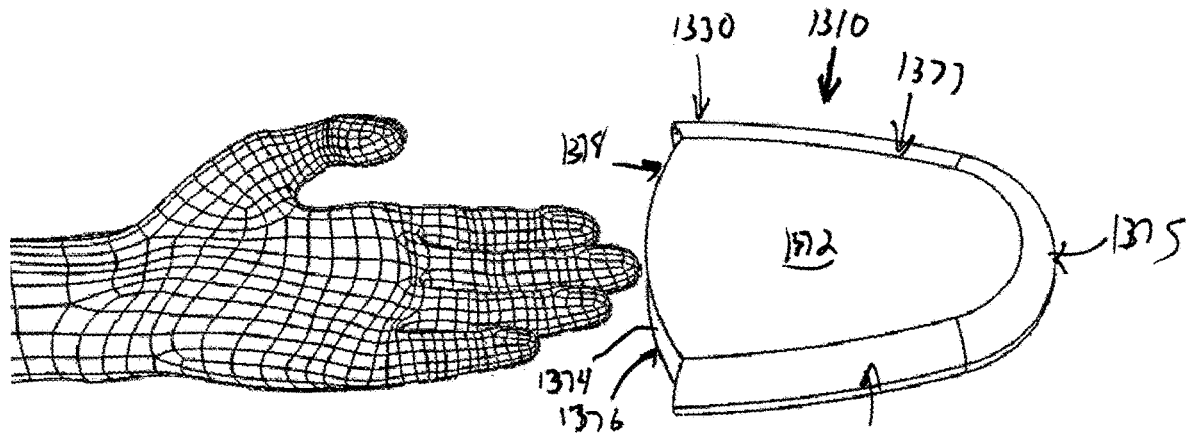
FIG. 37A illustrates a top perspective view of a user inserting their fingers into the on-demand agent dispensing pocket patch of FIG. 34 according to one embodiment of the present disclosure.
Figure 37B:
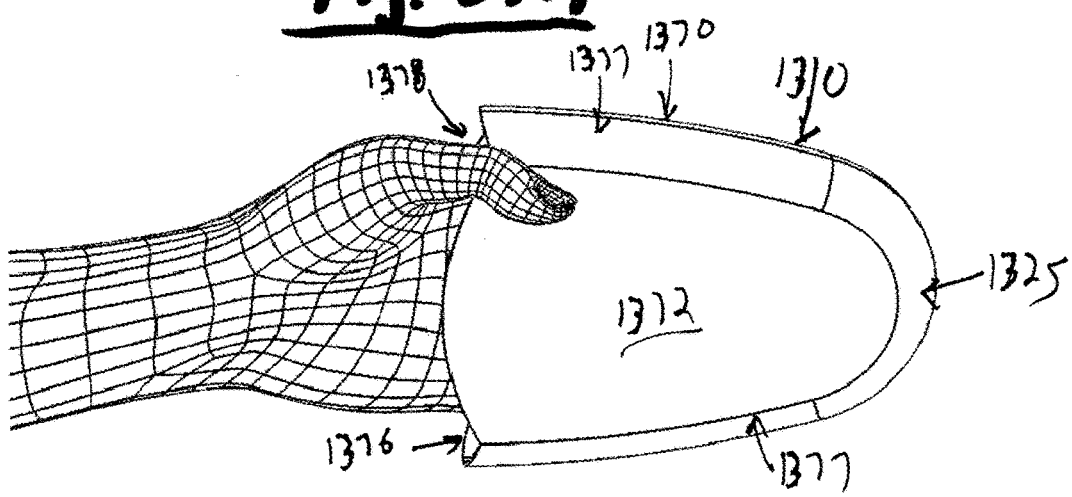
FIG. 37B illustrates a bottom perspective view of the user using the on-demand agent dispensing pocket patch of FIG. 37A to dispense a volume of agent onto their fingers according to one embodiment of the present disclosure.
Figure 37C:
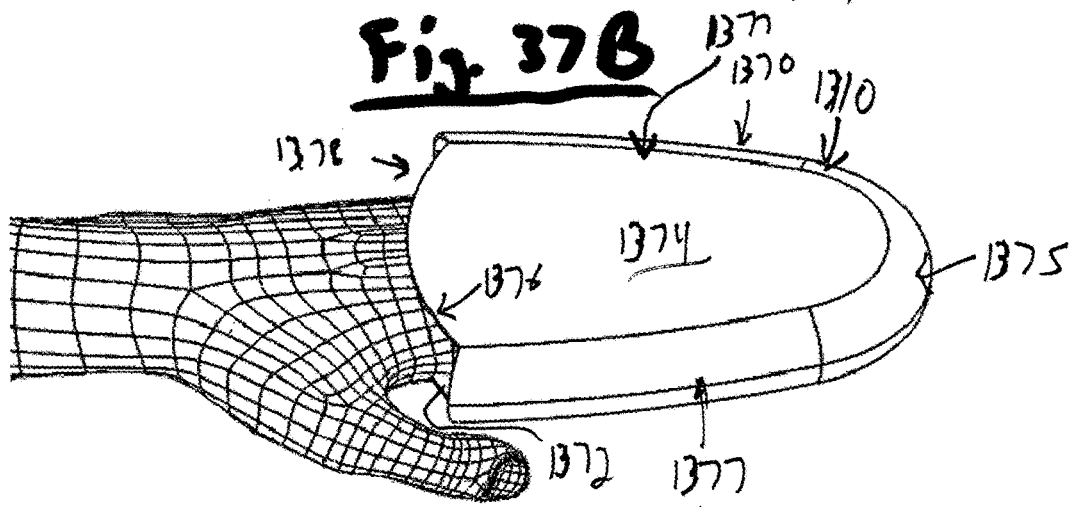
FIG. 37C illustrates a top perspective view of the user using the on-demand agent dispensing pocket patch of FIG. 37A to dispense a volume of agent onto their fingers according to one embodiment of the present disclosure.

The pocket patch device 1310 may be configured such that the interior cavity 1375 is sized and shaped to allow at least one finger of a user to extend into the interior cavity 1375 and engage the dispensing surface portion 1320 to compress the reservoir dispenser layer 1311 and dispense agent therefrom and onto the user, as shown in FIGS. 37A-C. As also shown in FIGS. 37A-C, in some embodiments the pocket patch device 1310 may be configured such that the interior cavity 1375 is sized and shaped to allow multiple fingers, or whole hand, of a user to extend into the interior cavity 1375 and engage the dispensing surface portion 1320 to compress the reservoir dispenser layer 1311 and dispense agent therefrom and onto the user's fingers/ hand.

Figure 35:
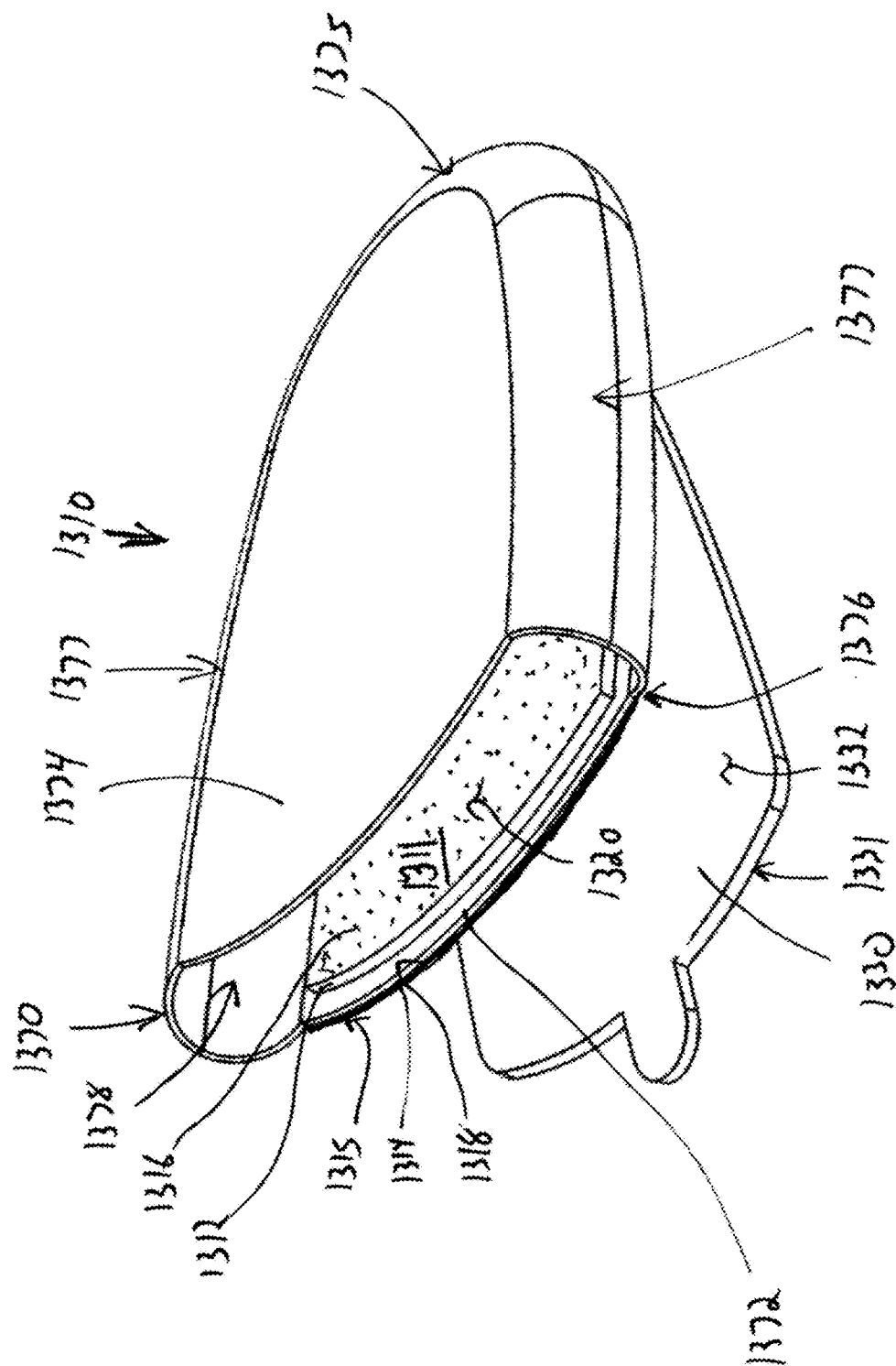
FIG. 35 illustrates another top perspective view of the on-demand agent dispensing pocket patch of FIG. 34 with an adhesive liner layer partially removed according to one embodiment of the present disclosure.
Figure 36:
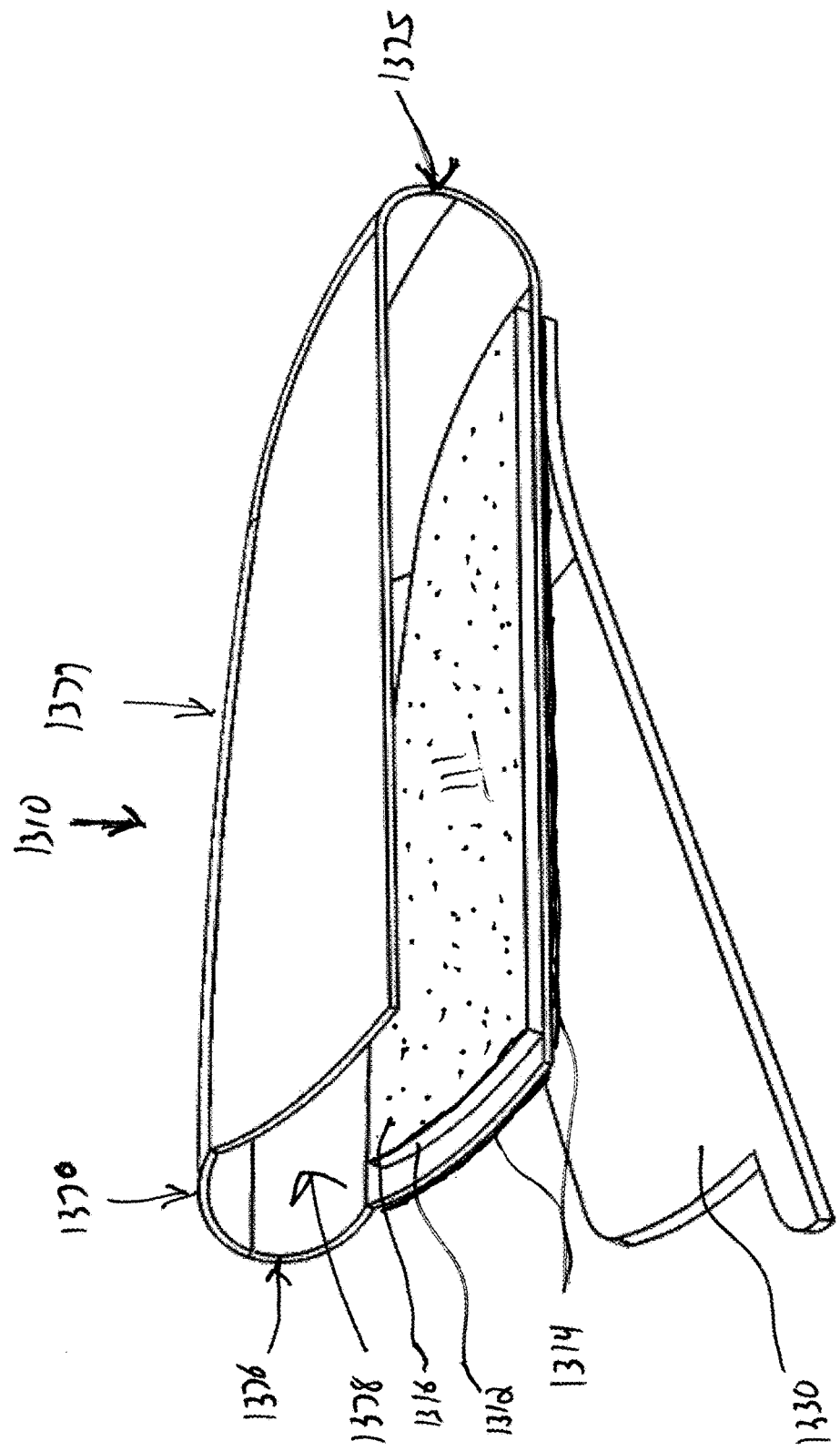
FIG. 36 illustrates a top perspective cross-sectional view of the on-demand agent dispensing pocket patch of FIG. 35 according to one embodiment of the present disclosure.

As shown in FIGS. 35 and 36, the outer side of the pocket 1370 may include the attachment layer or portion 1314 (and potentially a liner layer protecting/covering the attachment layer or portion 114) configured to removably couple the pocket patch device 1310 to a surface, as described above. In some embodiments, the outer side or face of the back portion 1372 may include the attachment portion 1314 coupled thereto, as shown in FIGS. 35 and 36. In some embodiments, the outer side or face of the front portion 1374 may include the attachment portion 114 coupled. In some embodiments, the outer side or face of the back portion 1372 may include a first attachment portion 1314 coupled thereto, and the outer side or face of the front portion 1374 may include a second attachment portion 1314 coupled thereto. As described above, the attachment portion(s) 1314 may be an adhesive or a mechanical mechanism configured to removably couple the pocket patch device 1310 to a surface, for example.

Figure 38:
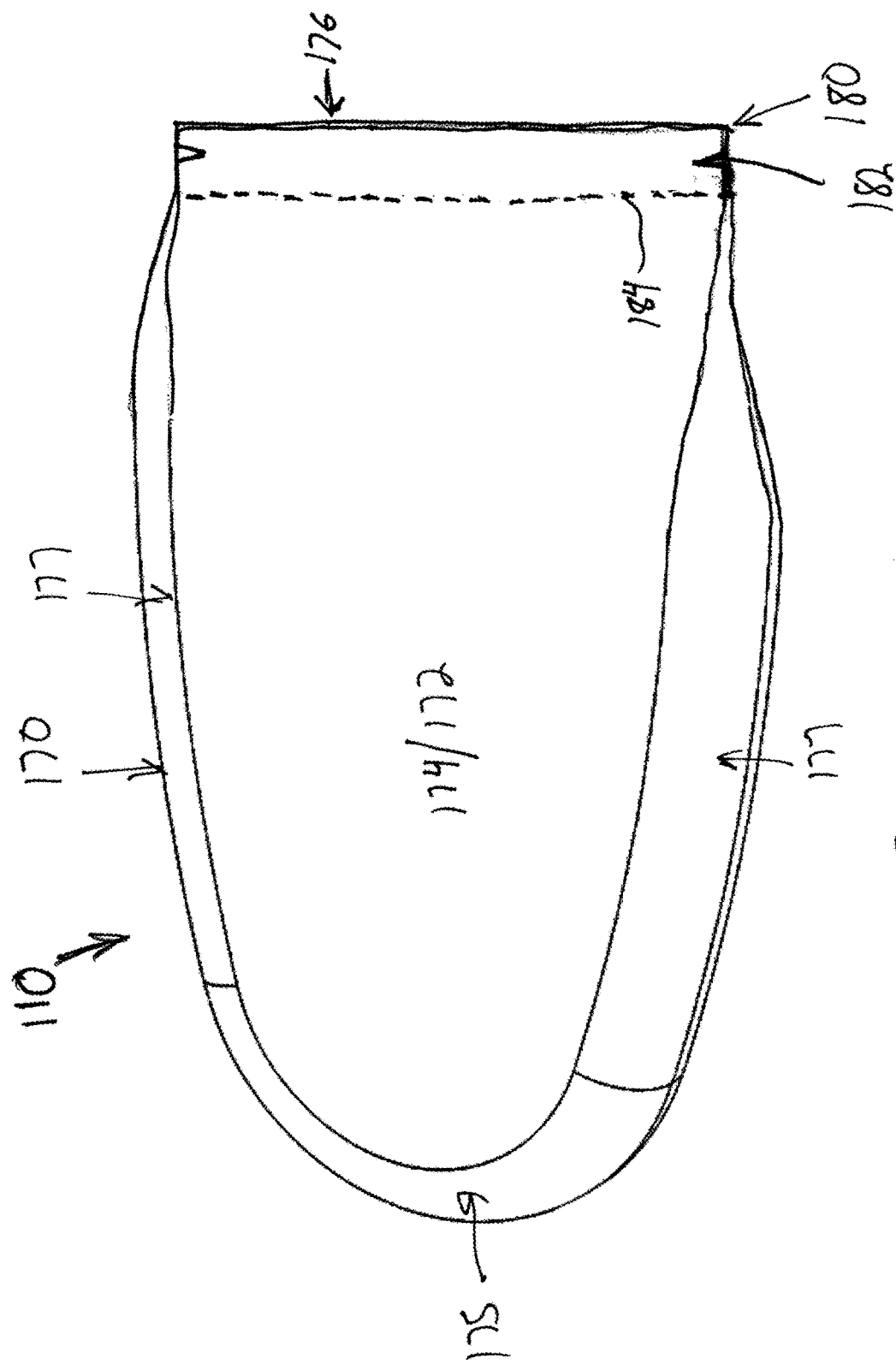
FIG. 38 illustrates a top perspective view of a resealable on-demand agent dispensing pocket patch according to one embodiment of the present disclosure.

In some embodiments, the top or upper end portion 1376 of the pocket 1370 may initially be closed (and potentially sealed), and be configured to be opened or unsealed. For example, as shown in FIG. 38, the top end portion 1376 of the pocket 1370 may include or comprise a closed construct. The closed construct may be sealed, and be configured to be openable and closable, or just openable, such that the top end portion 1376 becomes open to the interior cavity 1375.

As shown in FIG. 38, in some embodiments, the closed construct 1382 may include an openable and closable closure 1384. For example, the closure 1384 may be a peel-and-stick closure or a zipper closure (single or double, for example) that includes mating hooked channels or a mating hooked channel and hooked male member. The closure 1384 may allow for selective manual opening and closing/sealing of the top end portion 1376 for selective access to the interior cavity 1375. The closure 1384 may prevent an agent and/or air from flowing through the top end portion 1376 to/from the interior cavity 1375.

In some embodiments, as shown in FIG. 38, the top end portion 1376 of the pocket 1370 may have a seal 1380 at an end portion thereof that seals off the top end portion 1376 and access to/from the interior cavity 1375. As also shown in FIG. 38, in some such embodiments the top end portion 1376 may further comprise an unsealed portion 1382 positioned between the seal 1380 and the interior cavity 1375. The unsealed portion 1382 may be configured to be cut, broken, torn or otherwise disconnected such that the seal can be selectively separated from the pocket 1370 to open the top end portion 1376 and provide access to/from the interior cavity 1375. It is noted that the closure 1384, the seal 1380 and the unsealed portion 1382 may all be provided at the top end portion 1376.

It is to be understood that the above description is intended to be illustrative, and not restrictive. For example, the above-described examples (and/or aspects thereof) may be used in combination with each other. In addition, many modifications may be made to adapt a particular situation or material to the teachings of the various examples without departing from their scope. While dimensions and types of materials may be described herein, they are intended to define parameters of some of the various examples, and they are by no means limiting to all examples and are merely exemplary. Many other examples will be apparent to those of skill in the art upon reviewing the above description. The scope of the various examples should, therefore, be determined with reference to the claims included herein, along with the full scope of equivalents to which such claims are entitled.

As used herein, the terms "including" and "in which" are used as the plain-English equivalents of the respective terms "comprising" and "wherein." Moreover, as used herein, the terms "first," "second," and "third," etc. are used merely as reference labels, and are not intended to impose numerical, structural or other requirements. Forms of term "based on" herein encompass relationships where an element is partially based on as well as relationships where an element is entirely based on. Forms of the term "defined" encompass relationships where an element is partially defined as well as relationships where an element is entirely defined. Further, the limitations of the claims included herein are not written in means-plus-function format and are not intended to be interpreted based on 35 U.S.C. § 112, sixth paragraph, unless and until such claim limitations expressly use the phrase "means for" followed by a statement of function cavity of further structure. It is to be understood that not necessarily all such objects or advantages described above may be achieved in accordance with any particular example. Thus, for example, those skilled in the art will recognize that the systems and methods described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of examples, it should be readily understood that the disclosure is not limited to such disclosed examples. Rather, this disclosure can be modified to incorporate any number of variations, alterations, substitutions or equivalent arrangements not heretofore described, but which are commensurate with the spirit and scope of the disclosure. Additionally, while various examples have been described, it is to be understood that aspects of the disclosure may include only one example or some of the described examples. Also, while some disclosures are described as having a certain number of elements, it will be understood that the examples can be practiced with less than or greater than the certain number of elements.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

What is claimed is:

1. An on-demand liquid or gelatinous agent dispensing kit, comprising:
   a container containing a volume of a liquid or gelatinous agent; and
   a flexible patch configured to contain, and provide on-demand dispensing of, the agent via compression of the patch in a thickness direction thereof, the patch comprising:
      an adhesive layer configured to removably couple the patch to a surface, the adhesive layer defining an inner face of the patch;
      at least one reservoir layer that is configured to absorb and retain the agent therein, the at least one reservoir layer overlying the adhesive layer in the thickness direction;
      at least one dispenser layer overlying the at least one reservoir layer in the thickness direction comprising a plurality of solid portions and an array of a plurality of openings extending through a thickness thereof, the at least one dispenser layer configured to inhibit evaporation of the agent, and control a flow of the agent from the at least one reservoir layer upon the compression of the patch in the thickness direction, when the agent is contained within the at least one reservoir layer; and
      at least one backer layer positioned between the adhesive layer and the at least one reservoir layer in the thickness direction, the at least one backer layer being substantially impervious to the agent,
   wherein the solid portions of the at least one dispenser layer and portions of the at least one reservoir layer underlying the plurality of openings of the at least one dispenser layer define an outer face of the patch, and
   wherein the at least one reservoir layer is void of the agent absorbed therein.

2. The kit according to claim 1, wherein the adhesive is a biocompatible adhesive.

3. The kit according to claim 1, wherein the patch further comprises an inner protective film layer extending over and removably coupled to the adhesive layer.

4. The kit according to claim 1, wherein the liquid or gelatinous agent is a disinfectant.

5. The kit according to claim 4, wherein the disinfectant comprises ethyl, isopropyl, ethanol (ethyl alcohol), triclosan, triclocarban, benzalkonium chloride, benzethonium chloride or a combination thereof.

6. The kit according to claim 5, wherein the disinfectant comprises a dynamic viscosity within the range of about 4 (Pa·s) (m2/s) and about 15 (Pa·s) (m2/s) at 20 degrees Celsius.

7. The kit according to claim 1, wherein the at least one backer layer is substantially impervious to the agent and to air, and wherein the at least one backer layer comprises a solid sheet of material.

8. The kit according to claim 1, wherein the at least one dispenser layer comprises a sheet of material that is impervious to the agent and air, and wherein the at least one dispenser layer comprises a polymer layer.

9. The kit according to claim 1, wherein the solid portions of the at least one dispenser layer comprise within the range of about 10% and about 65% of the total area of the outer face, wherein the plurality of openings of the at least one dispenser layer comprise an average total area within the range of about 50 mm$^2$ and about 300 mm$^2$ at the outer face, and wherein each of the plurality of openings of the at least one dispenser layer comprise a total area within the range of about 0.05 mm$^2$ and about 0.3 mm$^2$ at the outer face.

10. The kit according to claim 1, wherein the at least one reservoir layer comprises one or more layers of polymer fibers, cotton fibers, silicone fibers, hydrogel or a combination thereof.

11. The kit according to claim 10, wherein the at least one reservoir layer comprises a fabric layer of non-woven polyethylene fibers, polypropylene fibers or a combination thereof.

12. The kit according to claim 1, wherein the at least one reservoir layer is configured to absorb and retain within the range of about 2 grams and about 50 grams of the agent, wherein the at least one reservoir layer comprises a detached agent capacity within the range of about 1,000 g/mm$^2$ and about 2,500 g/mm$^2$, and wherein the at least one reservoir layer comprises an agent absorbency rate of at least 5 g/sec for at least the first 5 seconds of water contact.

13. The kit according to claim 1, wherein, when the agent is contained within the at least one reservoir layer, the patch is configured such that a compressive force acting in the thickness direction and applied to the outer surface thereof of at least 1 gram/mm$^2$ causes the agent to flow through the plurality of apertures and onto the outer face and/or an object at the outer face.

14. The kit according to claim 1, wherein an inner portion of the patch defines a first maximum thickness, and a peripheral edge portion of the patch extending about the inner portion and defining an outer extent of the patch defines a second thickness that is less than the first thickness, wherein the peripheral edge portion of the patch defining the outer extent of the patch comprises the at least one reservoir layer, the at least one dispenser layer and the at least one backer layer being bonded together.

15. The kit according to claim 1, wherein, when the agent is contained within the at least one reservoir layer, the patch is configured such that no more than 5 grams of the agent evaporates over 1.5 hours in an ambient environment of non-moving air at 20 degrees Celsius.

16. The kit according to claim 1, wherein the adhesive layer on the outer side of the front face comprises an acrylic-based pressure-sensitive adhesive.

17. The kit according to claim 1, wherein the container is separate and distinct from the flexible patch.

18. The kit according to claim 1, wherein the container is integrated within, or coupled to, the flexible patch.

19. The kit according to claim 18, wherein the container is a manually breakable shell or envelope that is contained within the flexible patch.

20. The kit according to claim 19, wherein the manually breakable shell or envelope is a manually breakable polymer shell or container.

21. The kit according to claim 19, wherein the agent is a disinfectant.

22. The kit according to claim 21, wherein the disinfectant is a biocompatible disinfectant.

23. The kit according to claim 21, wherein the disinfectant comprises ethyl, isopropyl, ethanol (ethyl alcohol), triclosan, triclocarban, benzalkonium chloride, benzethonium chloride or a combination thereof.

24. The kit according to claim 23, wherein the disinfectant comprises a dynamic viscosity within the range of about 4 (Pa·s) (m2/s) and about 15 (Pa·s) (m2/s) at 20 degrees Celsius.

25. The kit according to claim 23, wherein the at least one backer layer is substantially impervious to the agent, and wherein the at least one backer layer comprises a solid sheet of material.

26. The kit according to claim 25, wherein the at least one reservoir layer comprises one or more layers of polymer fibers, cotton fibers, silicone fibers, hydrogel or a combination thereof.

27. The kit according to claim 25, wherein the at least one reservoir layer comprises a fabric layer of non-woven polyethylene fibers, polypropylene fibers or a combination thereof.

28. The kit according to claim 25, wherein the at least one backer layer is substantially impervious to air.

29. The kit according to claim 19, wherein the manually breakable shell or envelope is positioned adjacent to the at least one reservoir layer.

30. The kit according to claim 19, wherein the agent is a perfume, insect repellant, lotion, antiperspirant, lubricant, medicant, vitamin, cannabinoid or food product.

31. The kit according to claim 1, wherein the inner face and the outer face are substantially opposing faces of the patch in the thickness direction.

32. The kit according to claim 1, wherein the container is positioned within the flexible patch.

33. The kit according to claim 32, wherein the container is a manually breakable.

34. The kit according to claim 1, wherein the agent is a perfume, insect repellant, lotion, antiperspirant, lubricant, medicant, vitamin, cannabinoid or food product.

* * * * *